(12) United States Patent
Bartlett, II et al.

(10) Patent No.: US 9,409,003 B2
(45) Date of Patent: Aug. 9, 2016

(54) SYSTEM FOR REDUCING LOCAL DISCOMFORT

(71) Applicant: Awair, Inc., Stanford, CA (US)

(72) Inventors: Rush L. Bartlett, II, Palo Alto, CA (US); Ryan J. F. Van Wert, Palo Alto, CA (US); Stephen J. Ruoss, Redwood City, CA (US); Amy E. Bartlett, Palo Alto, CA (US)

(73) Assignee: Cook Medical Technologies, LLC, Bloomington, IN (US)

( * ) Notice: Subject to any disclaimer, the term of this patent is extended or adjusted under 35 U.S.C. 154(b) by 0 days.

(21) Appl. No.: 14/099,233

(22) Filed: Dec. 6, 2013

(65) Prior Publication Data

US 2014/0163527 A1 Jun. 12, 2014

Related U.S. Application Data

(60) Provisional application No. 61/823,070, filed on May 14, 2013, provisional application No. 61/808,142, filed on Apr. 3, 2013, provisional application No. 61/734,713, filed on Dec. 7, 2012.

(51) Int. Cl.
*A61M 31/00* (2006.01)
*A61M 19/00* (2006.01)
(Continued)

(52) U.S. Cl.
CPC ........... *A61M 31/00* (2013.01); *A61M 16/0409* (2014.02); *A61M 16/0438* (2014.02);
(Continued)

(58) Field of Classification Search
CPC ..................... A61M 16/0481; A61M 16/0484; A61M 16/0486; A61M 16/0434; A61M 16/0443; A61M 19/00; A61M 35/003; A61M 31/00; A61M 16/0409; A61M 16/0438; A61M 16/0445; A61M 16/0463; A61M 16/0488; A61M 16/0497; A61M 16/209; A61M 16/0461; A61M 2205/0266; A61M 2205/054; A61M 2205/057; A61M 2205/058; A61M 2205/183; A61M 2205/59
USPC ............. 604/258, 275, 264, 514; 128/200.24, 128/204.13
See application file for complete search history.

(56) References Cited

U.S. PATENT DOCUMENTS 1,236,865 A  8/1917  Pittenger
1,856,811 A *  5/1932  Toyojiro Inaki ................ 604/38
(Continued)

FOREIGN PATENT DOCUMENTS

EP  0 458 550 A2  11/1991
WO  WO 95-08305  3/1995
(Continued)

OTHER PUBLICATIONS

International Search Report issued Mar. 20, 2014 in connection with International Patent application No. PCT/US2013/073724. (3 pages).

(Continued)

*Primary Examiner* — Manuel Mendez
(74) *Attorney, Agent, or Firm* — Brinks Gilson & Lione

(57) ABSTRACT

A device for targeted delivery of a substance to an airway may include a conduit and at least two applicators. The

(51) Int. Cl.
   *A61M 16/04* (2006.01)
   *A61M 16/20* (2006.01)

(52) U.S. Cl.
   CPC ....... *A61M16/0445* (2014.02); *A61M 16/0463* (2013.01); *A61M 16/0488* (2013.01); *A61M 16/0497* (2013.01); *A61M 19/00* (2013.01); *A61M 16/0461* (2013.01); *A61M 16/209* (2014.02); *A61M 2205/0266* (2013.01); *A61M 2205/054* (2013.01); *A61M 2205/057* (2013.01); *A61M 2205/058* (2013.01); *A61M 2205/183* (2013.01); *A61M 2205/59* (2013.01)

(56) References Cited

U.S. PATENT DOCUMENTS

| | | |
|---|---|---|
| 3,814,103 A | 6/1974 | Fettel et al. |
| 4,182,326 A | 1/1980 | Ogle |
| 4,309,994 A * | 1/1982 | Grunwald ............... 604/28 |
| 4,693,243 A | 9/1987 | Buras |
| 5,146,916 A | 9/1992 | Catalani |
| 5,313,939 A | 5/1994 | Gonzalez |
| 5,389,074 A | 2/1995 | Parker et al. |
| 5,523,092 A | 6/1996 | Hanson et al. |
| 5,699,787 A | 12/1997 | Thompson |
| 5,707,352 A | 1/1998 | Sekins et al. |
| 5,709,874 A | 1/1998 | Hanson et al. |
| 5,803,078 A | 9/1998 | Brauner |
| 5,819,723 A | 10/1998 | Joseph |
| 5,891,101 A | 4/1999 | Wilcox et al. |
| 5,964,223 A | 10/1999 | Baran |
| 5,985,307 A | 11/1999 | Hanson et al. |
| 6,402,735 B1 | 6/2002 | Langevin |
| 6,487,446 B1 | 11/2002 | Hill et al. |
| 6,526,976 B1 | 3/2003 | Baran |
| 6,551,290 B1 | 4/2003 | Elsberry et al. |
| 6,729,334 B1 | 5/2004 | Baran |
| 6,766,801 B1 | 7/2004 | Wright |
| 7,153,292 B2 | 12/2006 | Morris et al. |
| 7,360,541 B2 | 4/2008 | Dhuper et al. |
| 7,469,700 B2 | 12/2008 | Baran |
| 8,074,649 B2 | 12/2011 | Dhuper et al. |
| 8,424,516 B2 | 4/2013 | Gray et al. |
| 8,556,880 B2 | 10/2013 | Freyman et al. |
| 8,777,927 B2 | 7/2014 | Cheney |
| 8,944,709 B2 | 2/2015 | Ellsworth et al. |
| 2003/0101991 A1 | 6/2003 | Trueba |
| 2004/0236286 A1 | 11/2004 | Klein |
| 2005/0016542 A1 | 1/2005 | Wright |
| 2006/0106350 A1 | 5/2006 | Spitz |
| 2009/0112047 A1 | 4/2009 | Carol et al. |
| 2009/0187238 A1 | 7/2009 | Weber et al. |
| 2009/0235935 A1 | 9/2009 | Pacey |
| 2009/0260632 A1 | 10/2009 | Abnousi et al. |
| 2010/0089393 A1 | 4/2010 | Brain |
| 2010/0179511 A1 * | 7/2010 | Rajan et al. ............. 604/514 |
| 2011/0030680 A1 | 2/2011 | Wood et al. |
| 2012/0184921 A1 | 7/2012 | Brillant |
| 2013/0053636 A1 | 2/2013 | Hayman et al. |
| 2014/0137867 A1 | 5/2014 | Pacey |
| 2014/0311497 A1 | 10/2014 | Daly et al. |
| 2015/0122834 A1 | 5/2015 | Ellsworth et al. |

FOREIGN PATENT DOCUMENTS

| | | |
|---|---|---|
| WO | 2004-101028 A2 | 11/2004 |
| WO | WO 2015/038870 A1 | 3/2015 |

OTHER PUBLICATIONS

Written Opinion of the International Searching Authority mailed on Mar. 20, 2014, for PCT Application No. PCT/US2013/073724, filed on Dec. 6, 2013. (5 pages).

Berra, L. et al., "A Clinical Assessment of the Mucus Shaver, A Device to Keep the Endotracheal Tube Free From Secretions", Crit Care Med. Jan. 2012; 40(1): 119-124. (16 pages).

Chadha, N. et al., "Automated Cuff Pressure Modulation: A Novel Device to Reduce Endotracheal Tube Injury", Arch Otolaryngol Head Neck Surg/vol. 137 (No. 1), Jan. 2011, pp. 30-34. (5 pages).

Elganzouri, A.R. et al., "The use of Air-Q as conduit for fiberoptic endotracheal intubation in adult paralyzed patients", Egyptian Journal of Anaesthesia, vol. 28, Issue 4, Oct. 2012, pp. 249-255. (7 pages).

Mallick, A. et al., "Local anaesthesia to the airway reduces sedation requirements in patients undergoing artificial ventilation", British Journal of Anaesthesia 1996; 77, pp. 731-734. (4 pages).

Moyers, G., "Use of the Cook Airware Exchange Catheter in "Bridging" The Potentially Difficult Extubation: A Case Report", AANA Journal; Aug. 2012; vol. 70, No. 4, pp. 275-278. (4 pages).

\* cited by examiner

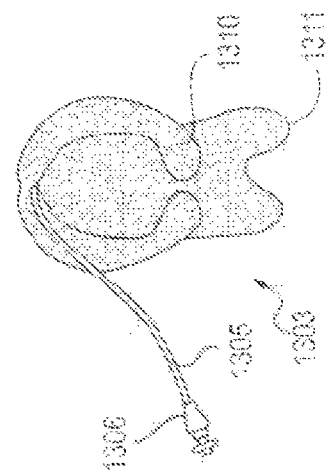
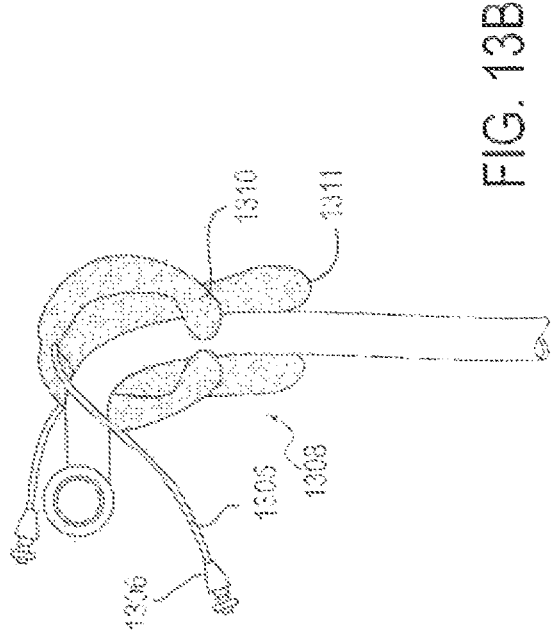
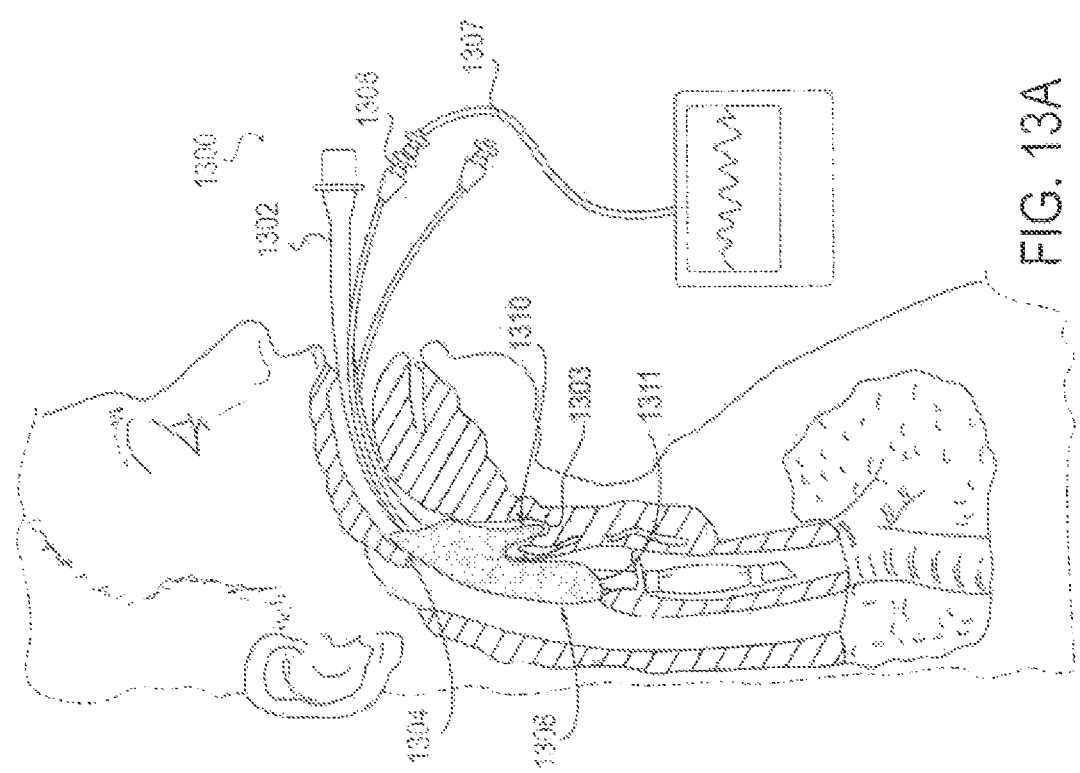

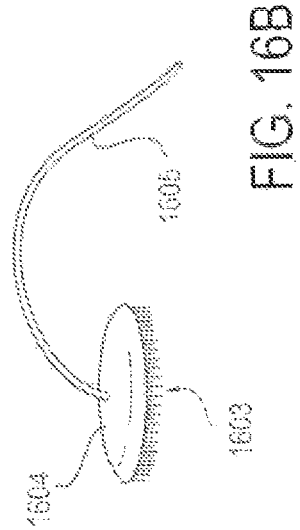
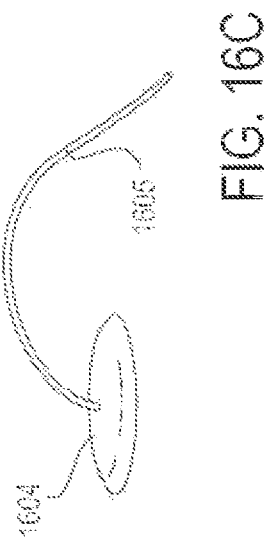
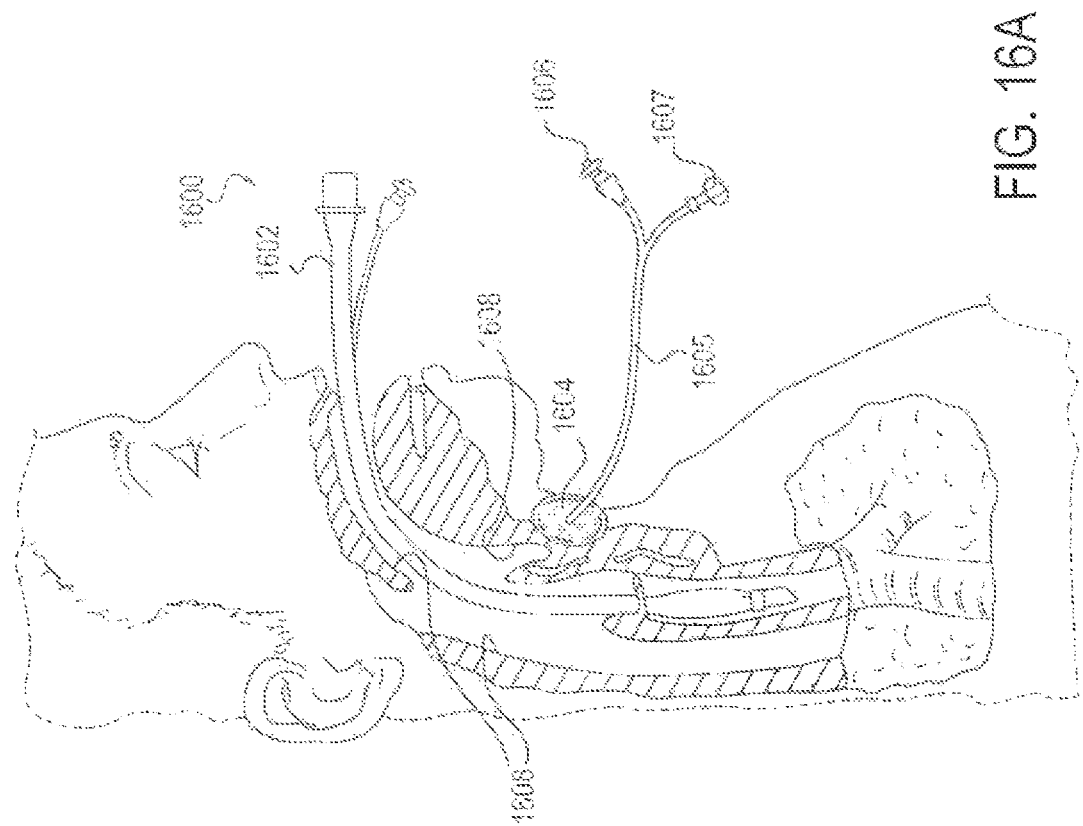

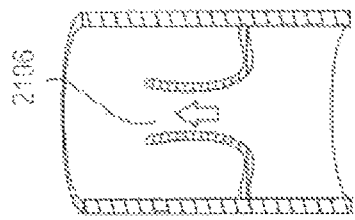
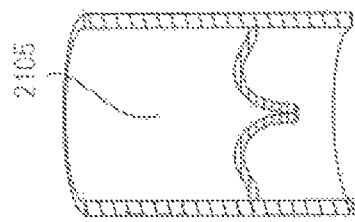
FIG. 20B
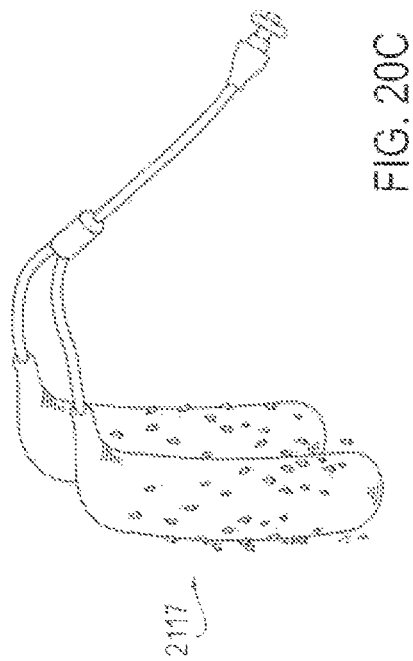
FIG. 20C
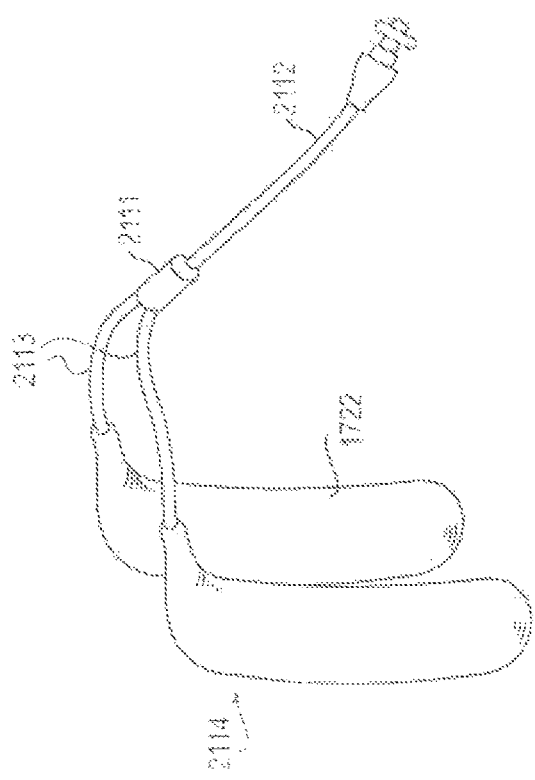
FIG. 20A

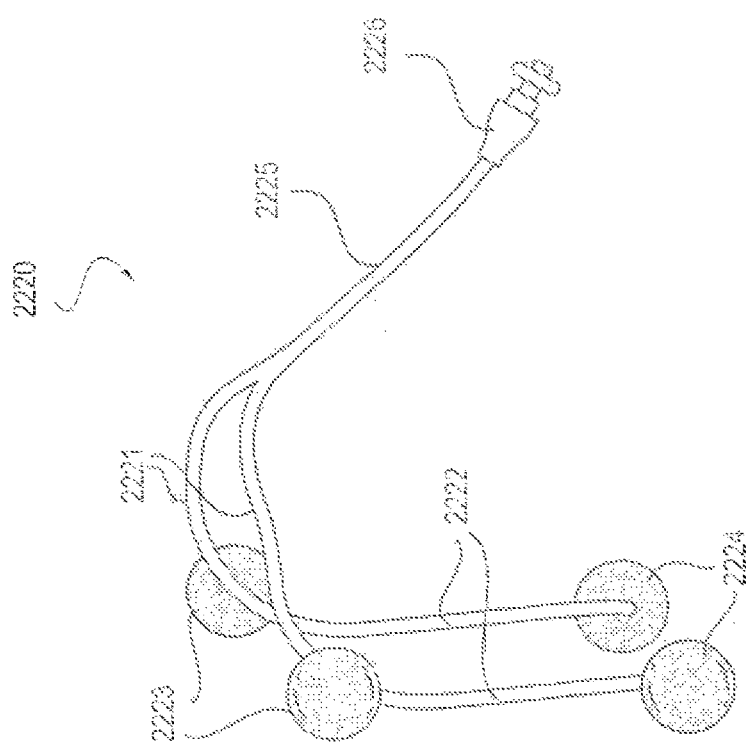

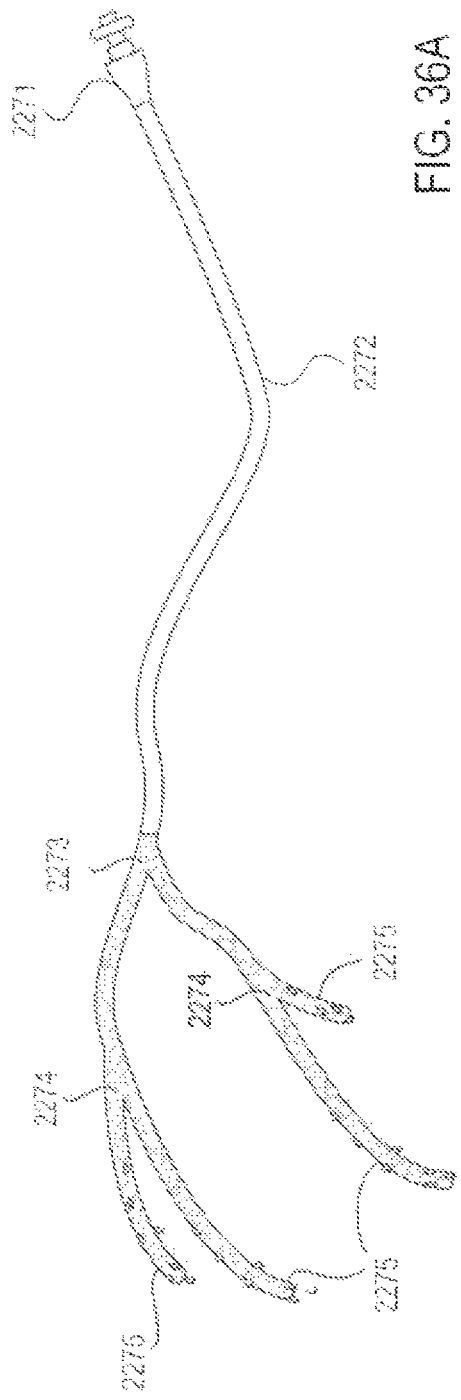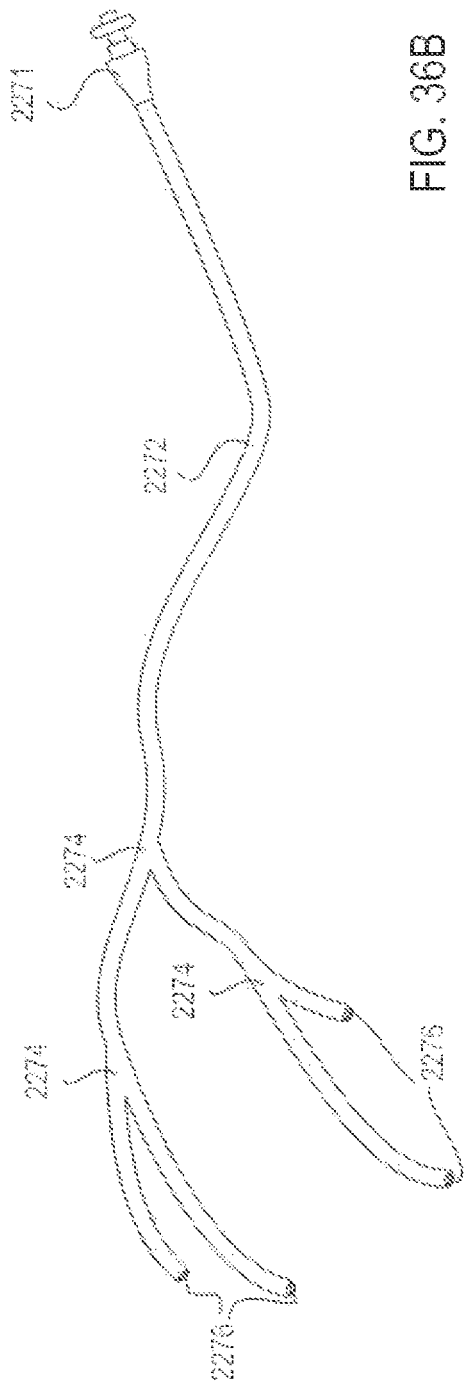

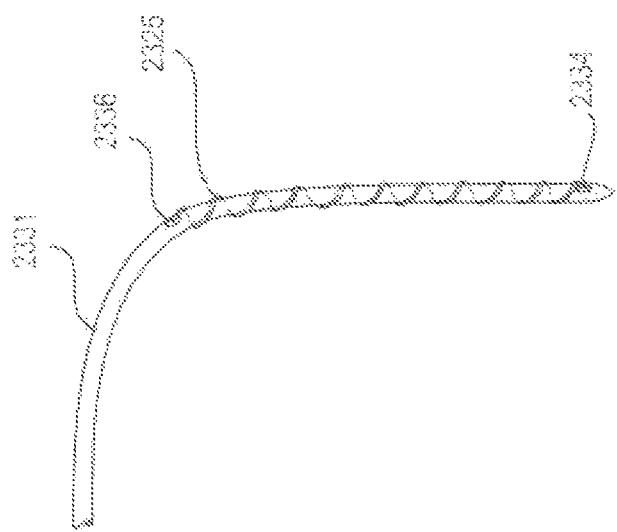

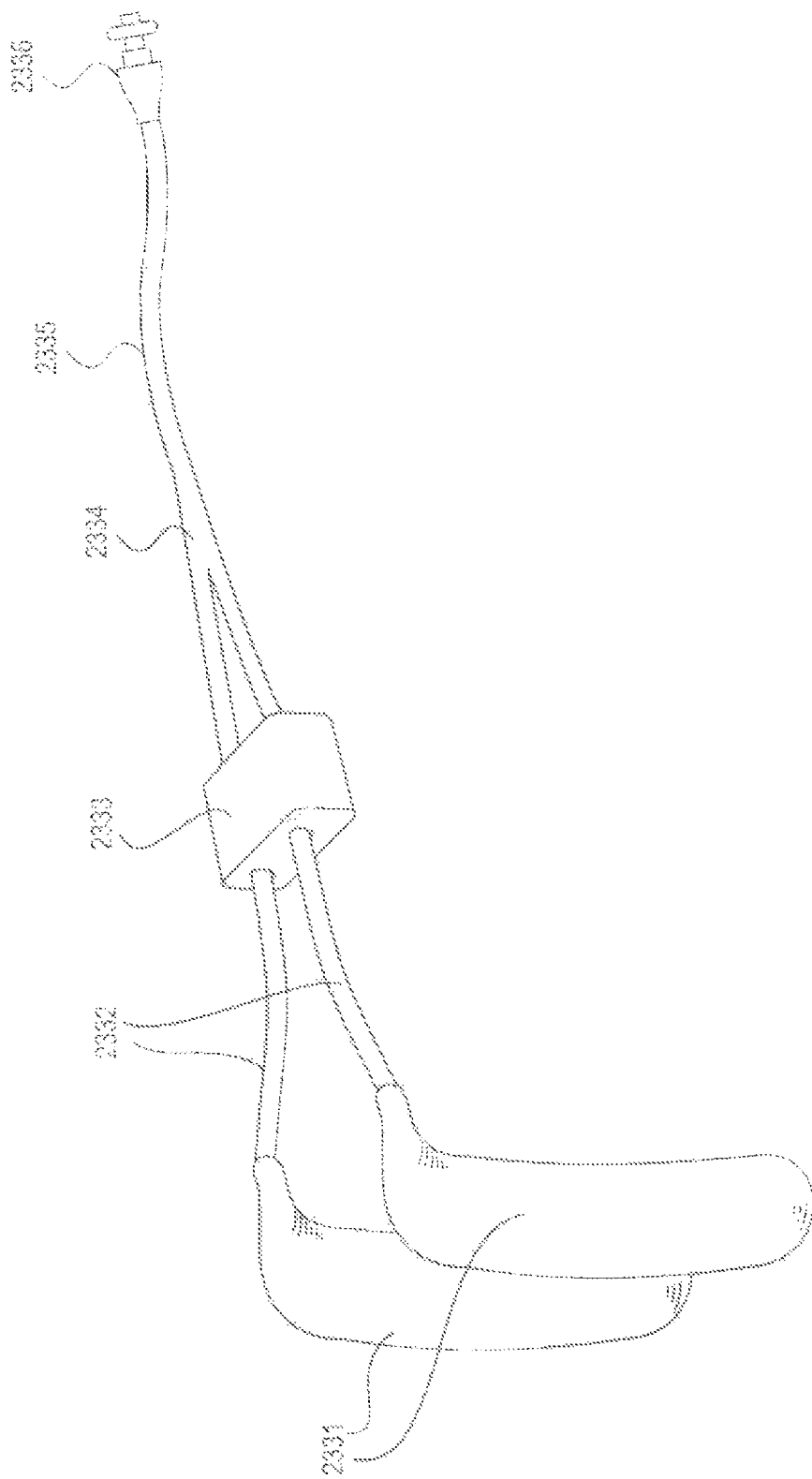

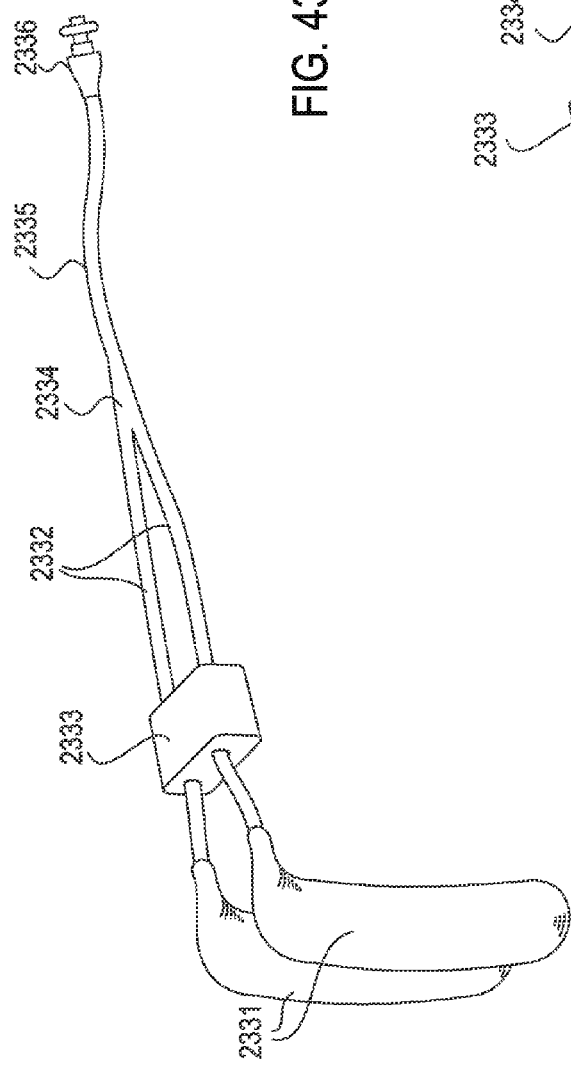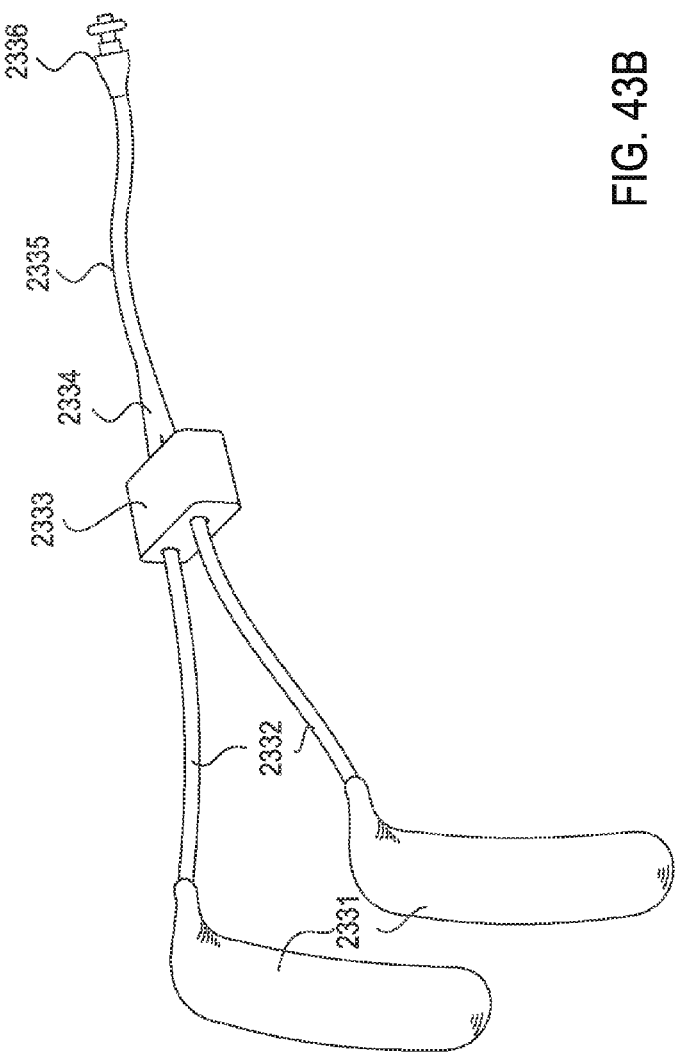

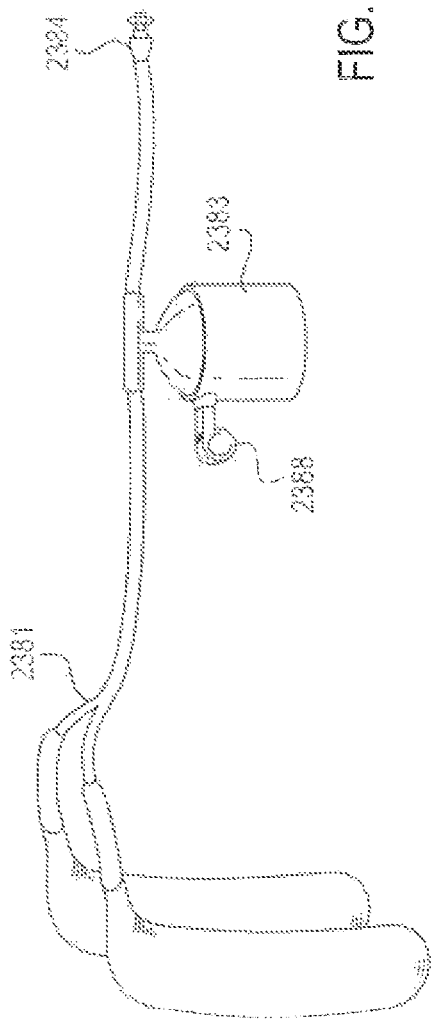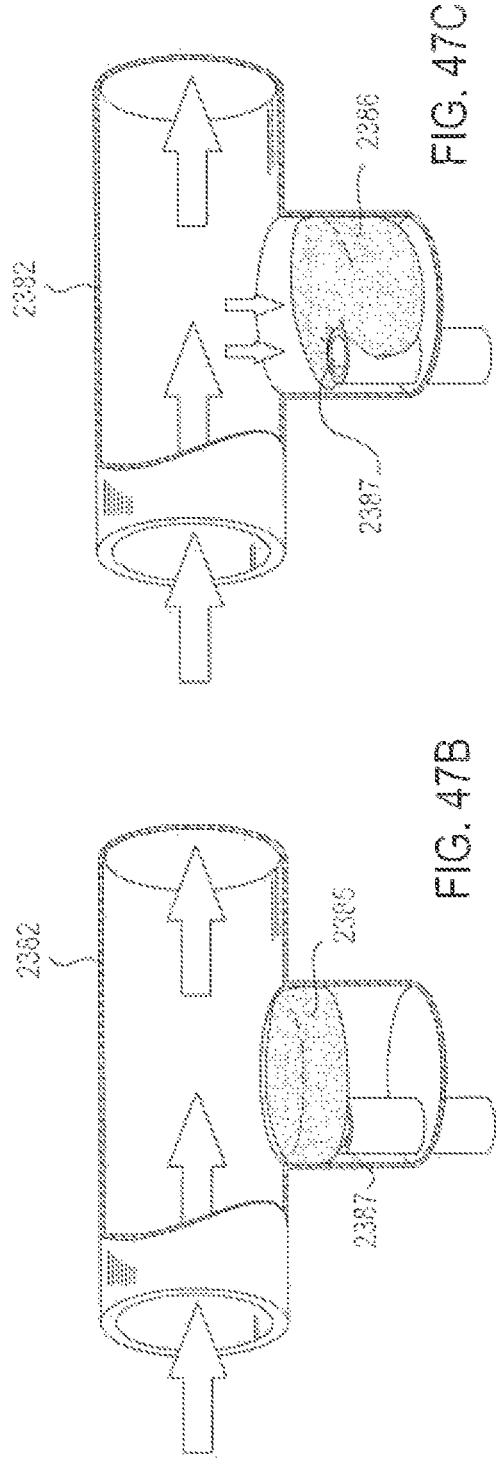

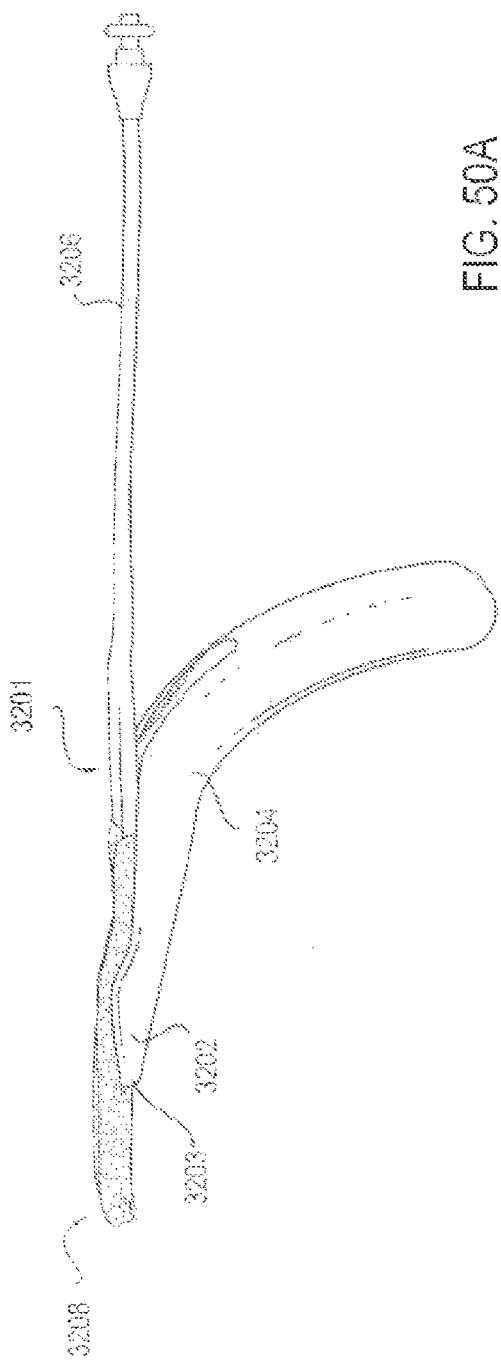
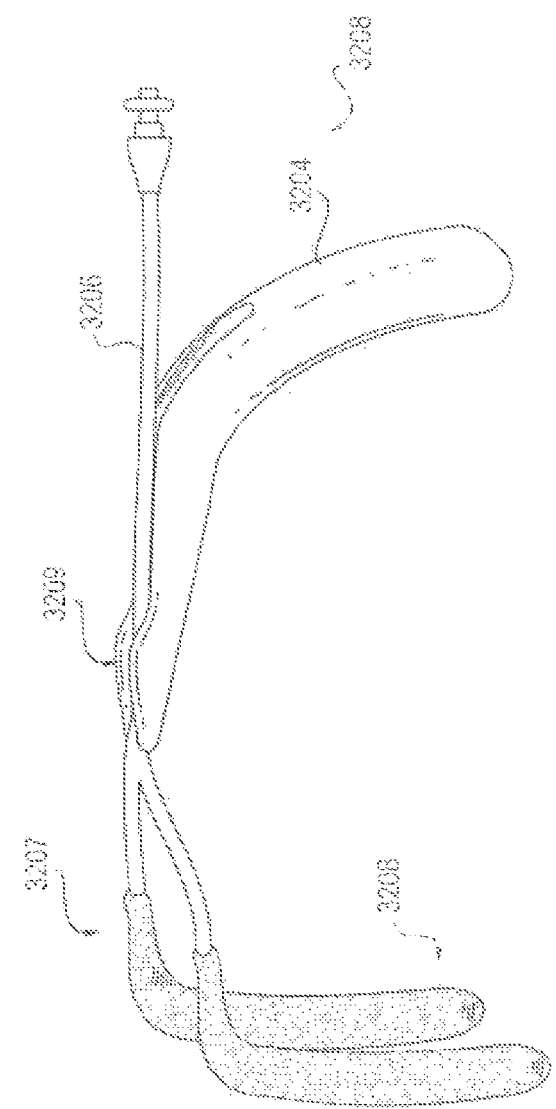
FIG. 50A
FIG. 50B

SYSTEM FOR REDUCING LOCAL DISCOMFORT

CROSS-REFERENCE TO RELATED APPLICATIONS

This application claims the benefit of U.S. Provisional Patent Application No. 61/734,713, entitled "System for Reducing Local Discomfort," as filed on Dec. 7, 2012; U.S. Provisional Patent Application No. 61/808,142, entitled "System to Reduce Discomfort in the Upper Airway," as filed Apr. 3, 2013; and U.S. Provisional Patent Application No. 61/823,070, entitled "System to Reduce Discomfort in the Upper Airway," as filed May 14, 2013. The full disclosures of all the above-referenced applications are hereby incorporated by reference herein.

BACKGROUND

Pain, agitation, gagging and other unpleasant sensations and reactions often accompany many types of medical procedures and/or medical situations in the mouth, nose, upper airway, and/or gastrointestinal tract. For example, patients who require endotracheal or gastrointestinal tube placement often suffer from many of these unpleasant sensations and reactions. Unfortunately, there are few currently available options for dealing with these unpleasant effects. Typically, such sensations are treated by injecting a local nerve block into effected tissues with a needle, a onetime spray of local anesthetic where the foreign object touches tissue, or the use of intravenous sedation. Local, injected nerve blocks and onetime sprays typically are not adequate and do not last long enough. Intravenous sedation is accompanied by many unpleasant side effects, such as contusion, delirium, increased length of intensive care unit stay, increased length of hospital stay, decreased mobility, increased healthcare costs, and increased number of days spent on a ventilator.

While a variety of innovations have been tried, in an effort to reduce sensation, discomfort or pain in the airway, improved systems, devices and methods would still be desirable. Ideally, such improved systems, devices and methods would provide local anesthesia to relevant parts of the airway in order to reduce the pain, discomfort and anxiety induced by the endotracheal tube, particularly on a continuous or long term basis. Also ideally, such systems, devices and methods could be used in a wide variety of settings and patients. Finally, it would be ideal if these systems, devices and methods could be used, or adapted for use, in other body areas, such as the gastrointestinal tract, or for other indications. At least some of these objectives will be met by the embodiments described herein.

BRIEF SUMMARY

Devices, systems and methods for modulating motor, sensory and/or autonomic function, or perception thereof, are described herein. The devices, systems and methods are generally configured to deliver a therapy to the airway (or other bodily tracts, such as the gastrointestinal tract), to relieve discomfort in the airway caused by airway devices, other foreign bodies, tumors, or any other cause of discomfort. The devices may be employed anywhere along the length of the airway, from the nose or month to alveolus. The system may also be applied to other areas of the body, including the gastrointestinal tract. The system may be used to reduce sensation, discomfort or pain in a specific area of interest, on a temporary or permanent basis. For instance, the system may be used in patients with an endotracheal tube in situ in the intensive care unit, operating or procedure room, in order to reduce discomfort associated with the endotracheal tube in the airway. The system may be used on a temporary or permanent basis in patients with a nasogastric or orogastric tube, in order to reduce the discomfort associated with these objects in the airway or esophagus. The system may also be used during procedures in the airway to reduce sensation, discomfort or pain, such as bronchoscopy, upper gastrointestinal endoscopy, transesophageal echocardiography, dental procedures, biopsy procedures, surgical procedures of the head, neck or thorax, or the like. This is not an exhaustive list. Descriptions of specific uses and/or applications of the system are not intended to limit the scope of the invention as described in the claims.

In one aspect, a device for targeted delivery of a substance to an airway may include: a conduit comprising a proximal end and a bifurcated distal portion having two distal ends, where the proximal end is configured to be coupled with a source of the substance; and at lease two applicators, each applicator coupled with one of the distal ends of the conduit, where each applicator is configured to direct the substance out of the applicator toward one of two sides of an airway. In some embodiments, the distal portion of the conduit may be configured to apply laterally directed, opposing force to the two applicators to cause them to move apart from one another to contact the two sides of the airway. In some embodiments, at least the distal portion of the conduit may include a shape memory material that applies the force by returning to an unconstrained configuration from a constrained configuration. Alternatively or additionally, the device may include a separator coupled with the conduit for separating the distal ends of the conduit, and the applicators to cause the applicators to apply the laterally directed force against the airway. In some embodiments, the separator may be configured to bring the distal ends of the conduit and the applicators toward one another for removal of the device from the airway.

In some embodiments, the device may be configured to be advanced into the airway and used for substance delivery without requiring attachment to any other airway device. One embodiment may include two conduits joined together along at least part of the proximal portion and separate from a bifurcation to the distal ends, where one of the at least two applicators is coupled with one of the distal ends of each of the two conduits. In some embodiments, the applicators may have a curved configuration to conform to a curved portion of the airway such that each applicator, when positioned in the airway, contacts the airway near a glossopharyngeal nerve and/or a superior laryngeal nerve on each of the two sides of the airway. In some of these embodiments, each applicator, when positioned in the airway, may contact the airway at or near a posterior tonsillar pillar and/or a piriform sinus.

In some embodiments, the applicators may be made at least partially of a material configured to allow the substance to weep slowly out of the applicators. Optionally, the device may further include an attachment member on the conduit for attaching the device with an endotracheal tube. In alternative embodiments, the conduit may be part of an endotracheal tube.

In some embodiments, the applicators may be configured to remain within the airway over a period of time dining which an endotracheal tube remains within the airway. In various embodiments, the proximal end of the conduit may be configured to attach to a mechanically driven source of the substance, such as but not limited to an IV syringe pump, an IV pump, a balloon pump, an IV bag, or any of a number of other mechanically driven substance reservoirs. In various embodiments, the applicators and/or the source of substance may be configured to control a rate and/or an amount of substance delivered.

In another aspect, a device for targeted delivery of a substance to an airway may include: at least one conduit having a proximal end and a distal end, where the proximal end is configured to be coupled with a source of the substance; and at least one applicator coupled with the distal end of the conduit, where each applicator is configured to direct the substance out of the applicator toward one of two sides of an airway. In some embodiments, the applicator may be a bifurcated applicator configured to apply laterally directed, opposing force to the two sides of the airway. In some embodiments, the bifurcated applicator may include a shape memory material that applies the force by returning to an unconstrained configuration from a constrained configuration. In some embodiments, the device may include two conduits and two applicators, where each applicator is coupled with a distal end of one of the two conduits, and where each applicator/conduit pair is configured to be applied separately to one of the two sides of the airway.

In another aspect, a method for targeted delivery of a substance to an airway may involve: advancing a substance delivery device into the airway; contacting two sides of the airway with at least two applicators of the substance delivery device, such that each applicator contacts the airway near a glossopharyngeal nerve and/or a superior laryngeal nerve on one of the two sides of the airway; and delivering the substance through the applicators to contact the airway along the two sides, in some embodiments, contacting the airway with the applicators may involve applying lateral oppositely directed force to the two sides of the airway with the applicators. For example, contacting the airway may involve releasing the applicators from a constrained configuration to assume an unconstrained configuration. In some embodiments, contacting the airway may involve separating the applicators apart using a separator coupled with the substance delivery device. Optionally, the method may further involve using the separator to bring the applicators closer together and removing the device from the airway with the applicators closer together.

In some embodiments, the substance may be an anesthetic agent. For example, the anesthetic agent may be lidocaine, in some embodiments. In some embodiments, the substance may be delivered in a manner such that the substance has a continuous effect during a period of time lasting at least a few minutes and as long as multiple days. In some embodiments, the substance may be delivered intermittently during at least part of the period of time to provide the continuous effect. Alternatively or additionally, the substance may be delivered continuously during at least part of the period of time to provide the continuous effect.

According to some embodiments, the substance may be delivered at least in part while an additional airway device is in place within the airway. In some embodiments, the substance delivery device may be advanced into the airway simultaneously with advancing an additional airway device into the airway. Alternatively, the substance delivery device may be advanced before or after advancing an additional airway device into the airway. In some embodiments, the method may further involve allowing the substance delivery device to remain in the airway during a period of time of at least a few minutes and as long as multiple days. In some embodiments, an additional airway device may be positioned in the airway during at least part of the period of time. Some embodiments of the method may further involve, before delivering the substance, attaching a conduit of the substance delivery device to a mechanically driven substance delivery reservoir, where delivering the substance then involves automatically delivering the substance from the reservoir through the conduit to the applicators.

In another aspect, a method for targeted delivery of a substance to an airway of a patient may involve: advancing a substance delivery device into the airway; attaching a conduit of the substance delivery device to a mechanically driven substance delivery reservoir; advancing the substance from the reservoir through the conduit and through at least two applicators coupled with the conduit to cause the substance to contact the airway near a glossopharyngeal nerve and/or a superior laryngeal nerve; and leaving the substance delivery device in the airway throughout a duration of a treatment of the patient with the substance delivery device. In this embodiment, the substance may be advanced automatically from the reservoir, without removing the substance delivery device from the airway during the duration of the treatment. In some embodiments, the substance is advanced through the applicators to contact the airway without inserting any needles into the airway.

In another aspect, a system for targeted delivery of a substance to an airway may include: conduit including a proximal end and a bifurcated distal portion having two distal ends; at least two applicators, each applicator coupled with one of the distal ends of the conduit, where each applicator is configured to direct the substance out of the applicator toward one of two sides of an airway, and a mechanically driven reservoir for containing the substance, coupling with the proximal end of the conduit, and delivering the substance into the conduit at least partially automatically.

In some embodiments, the distal portion of the conduit may be configured to apply laterally directed, opposing force to the at least two applicators to cause them to move apart from one another to contact the two sides of the airway. In some embodiments, the applicators may have a curved configuration to conform to a curved portion of the airway such that each applicator, when positioned in the airway, contacts the airway near a glossopharyngeal nerve and/or a superior laryngeal nerve on one of the two sides of the airway. Some embodiments may further include an attachment member on the conduit for attaching the conduit with an endotracheal tube. In various embodiments, the reservoir may includes but is not limited to, an IV syringe pump, an IV pump, a balloon pump, an IV bag, or any of a number of other mechanically driven substance reservoirs.

In some embodiments, the applicators and/or the reservoir may be configured to control at least one of a rate or an amount of substance delivered. In some embodiments, the system may further include the substance itself. For example, in some embodiments, the substance may be lidocaine.

These and other aspects and embodiments are described in further detail below, in reference to the attached drawing figures.

BRIEF DESCRIPTION OF THE DRAWINGS

The present invention will be better understood from the following description of certain examples, in conjunction with the accompanying drawings, in which like reference numerals identify the same elements and in which:

FIG. 13A is a partial cross-sectional view of a patient with an endotracheal tube in place, along with an applicator device for reducing discomfort and pain from the endotracheal tube by delivering energy, according to one embodiment;

FIG. 13B is a perspective view of the applicator device of FIG. 13A, coupled with the endotracheal tube;

FIG. 13C is a perspective view of the applicator device of FIGS. 13A and 13B;

FIG. 16A is a partial cross-sectional view of a patient with an endotracheal tube in place, along with an applicator device for reducing discomfort and pain from the endotracheal tube via energy delivery and/or chemical substance delivery, according to another alternative embodiment;

FIG. 16B is a perspective view of an external applicator for use with the applicator device of FIG. 16A, including micro needles or needles, according to one embodiment;

FIG. 16C is a perspective view of an external applicator for use with the applicator device of FIG. 16A, including adhesive attachment means and a surface application means without needles, according to an alternative embodiment;

FIGS. 17A-17D are partial cross-sectional views of a patient with a sheath-like applicator device in place for reducing discomfort and pain from the endotracheal tube, according to another alternative embodiment;

FIGS. 20A-20C are various views of an applicator system with an alternative valve embodiment that facilitates intermittent pulsatile delivery of active substance, according to an alternative embodiment;

FIG. 31 is a perspective view of an applicator system in which reservoir sponge components are attached to bifurcated tubing in separate places, according to one embodiment;

FIGS. 36A-36B are perspective views of two embodiments of applicator systems with multiple bifurcations and drug applicator capability, according to various alternative embodiments;

FIG. 41 is a side view of an applicator with hydrophilic and/or hydrophobic spiraled flow contours, according to one alternative embodiment;

FIG. 42 is a perspective view of an applicator system with an adjustable feature that slides forward and back along the delivery conduits to adjust their spread, according to one embodiment;

FIGS. 43A and 43B are perspective views of the applicator system of FIG. 42, illustrating sliding of the adjustable feature forward and back along the delivery conduits to adjust their spread and/or the contour curve of the applicators, according to one embodiment;

FIGS. 47A, and 47B and 47C are perspective views of an applicator system with a pressure relief and high flow bypass valve dial may or may not also have an auditory or visual indicator of a high flow state like a whistle, according to one embodiment;

FIGS. 50A and 50B are perspective, diagrammatic views of an introducer means for introducing an applicator device into an airway, according to one embodiment;

Figure 1B:
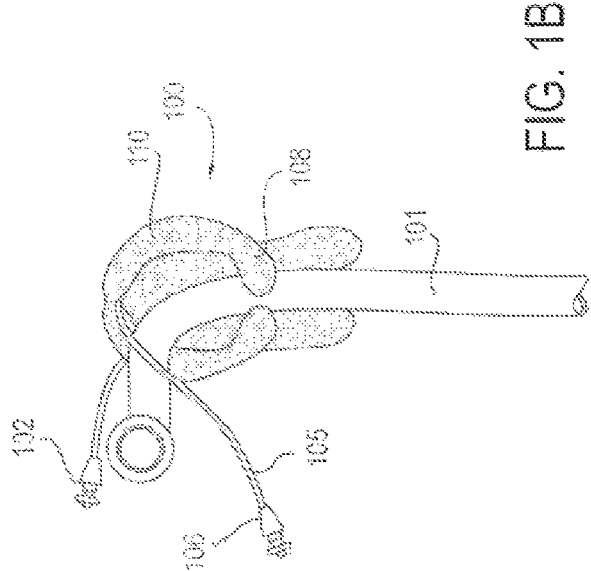
FIG. 1B is a perspective view of the applicator device of FIG. 1A, coupled with the endotracheal tube.

The drawings are not intended to be limiting, and various embodiments of the invention may be carried out in a variety of other ways, including those not necessarily depicted in the drawings. The drawings may not necessarily be drawn to scale. The accompanying drawings incorporated in and forming a part of the specification illustrate several aspects of the present invention, and together with the description serve to explain the principles of the invention. However, this invention is not limited to the precise arrangements shown.

DETAILED DESCRIPTION

The following description of various embodiments should not be interpreted as limiting the scope of the invention described by the claims. Various alternative features, aspects, and changes to described embodiments, some of which may not be described in detail below, may be used with or incorporated into alternative embodiments without departing from the scope of the claims. Accordingly, the drawings and descriptions should be regarded as illustrative in nature and not restrictive.

System for Reducing Local Discomfort in the Upper Airway

Described herein are various embodiments of a system, device and method for delivering one or more substances to an upper airway to reduce and/or modulate sensations of discomfort or pain, gag reflexes and/or other motor and/or autonomic functions, and the like. The systems, devices and methods herein are generally configured to provide targeted delivery of substance(s) to the airway to provide a continuous effect. By "targeted delivery" it is meant that the substance is (or substances are) delivered, at least initially, to only a portion of the upper airway rather than all of it. Although such delivered substance(s) may subsequently flow along other portions of the airway, the initial delivery to the airway is targeted at least to some extent. Providing targeted delivery is thus different than providing a general, systemic anesthetic.

"Continuous effect" means that the delivered substance (or substances) continues to work over a period of time. The substances may be delivered continuously over the time period or intermittently over the time period, but the effect will generally be continuous. The period of time during which the continuous effect is provided may be any suitable time, from minutes to hours or even days, for example in an intensive care unit patient who is continuously incubated for days. Although many embodiments are capable of targeted delivery of substance(s) to provide a continuous effect, the systems, devices and methods described herein are not limited to targeted delivers or continuous effect. For example, some of the substance delivery device embodiments described herein may be used to provide intermittent effect. Furthermore, although the embodiments are generally described, herein for use in the upper airway, many or all embodiments may be altered to address different parts of the body, such as but not limited to the gastrointestinal tract.

Generally, the systems, devices and methods herein may be used to affect a nerve structure (peripheral or central) known to innervate an area of interest. In many embodiments, the system, device and/or method is configured for use in providing continuous anesthetic effect to an airway. However, alternative embodiments may be configured for use in the gastrointestinal tract or other body lumens or tissues.

Although various descriptions herein refer to a "system" or "device," these terms may be used interchangeably and should not be interpreted as limiting any particular embodiment unless such limitation is specifically called out in the description. For example, many of the descriptions herein refer to an "applicator device," which may be used to apply one or more substances to tissues, such as anesthetic substance(s) to upper airways. Since most of the applicator device embodiments herein have multiple component parts, an applicator device may also sometimes be referred to as an "applicator system." Alternatively, these devices or systems may be referred to as "substance delivery devices" or "substance delivery systems." In other words, the nomenclature used for any given embodiment of one of the devices or systems should not be interpreted as limiting that embodiment.

In various embodiments, the system may also be directly applied to a specified tissue, so that a desired neuromodulatory or neurosensory effect is achieved. Application to a tissue may also facilitate transit of pharmaceutical compounds, electrical signals and/or mechanical signals through fluid transport in lymphatic vessels, interstitial fluid and/or blood to nerve structures adjacent to a specified tissue. Such specified tissues may include but are not limited to the following: nasopharynx, oropharynx, hypopharynx, uvula, epiglottis, tonsils and adenoids, tonsillar pillars, piriform sinuses, false and true vocal cords, larynx, hyoid bone, trachea, bronchi, bronchioles, alveoli, skin, neck, or any mucosal surface in the body, including the entire gastrointestinal tract and/or airway.

The system may be independent or integrated with other devices. Including but not limited to an endotracheal tube, nasogastric tube, orogastric tube, endotracheal tube securing/anchoring device, bronchoscope, endoscope, transesophageal echocardiography probe, and/or surgical instrument. The system may be applied on a one-time basis, such as to provide local anesthesia to the desired part of the upper airway, intermittently, or on a continuous basis to provide local anesthetic when instruments rest in situ for prolonged periods of time, such as endotracheal tubes, nasogastric tubes, orogastric tubes, or packing materials in patients admitted to hospital, to the intensive care unit, or who are treated on an outpatient basis. If flow is continuous, it may be uniform flow or oscillatory or pulsatile flow for greater than a few seconds to minutes of time, whereas one-time or intermittent application may describe treatment for less than a few minutes of time.

The system may achieve the desired effect through, but not limited to, delivery of chemicals, drugs, medicines and/or other pharmacological compounds, application of heat or cold, radiofrequency energy, electrical stimulation, sound, ultrasound, any other wavelength of electromagnetic energy, magnetic forces, or electromagnetic forces. Energy may be applied as a shockwave, impulse, or in any other pattern (e.g. sinusoidal, variable or constant frequency) to achieve the desired effect. Various sensory modalities may be applied to the body area in question (e.g. alternating head and cold, vibrations at a given frequency, pain) in order to achieve the desired effect. In addition medicines known to achieve the desired effect may be employed such as topical anesthetics (e.g., lidocaine, procaine, allocaine, benzocaine, tetracaine, cocaine, eutectic mixture of local anesthetics (EMLA), with or without additive medications such as epinephrine or other vasoactive medications, opiate medications (e.g., fentanyl, sufentanil, remifentanyl, dilaudid, morphine), other sedative medications (e.g. midazolam, propofol, phenobarbital, dexmedetomidine), antimicrobial medications including antibiotics, antivirals, antifungals, bactericidal or bacteriostatic substances. Other medications can also be delivered, if an alternate effect is desired (e.g. vasodilator, vasoconstrictor agents, or any other medicine in which direct application to a given area of the body is desired.

The system may be employed on a one-time basis, intermittently, or continuously, ranging from seconds to several days or weeks. The device may be left in situ between uses, or removed and reapplied. The system may be deployed on the skin surface (even if an internal effect is desired), a mucosal surface, or via a transvascular, subcutaneous or submucosal needle or microneedle approach. The system may also be deployed by directly implanting the system around or near the nervous structure or body tissue where the effect is desired.

The system, if applied to a mucosal surface, may be used to deliver anesthetic or other pharmaceutical components to the mucosal surface of the airway or gastrointestinal tract such that nerve structures near, beneath, or adjacent to the mucosal surface are affected by diffusing anesthetic through the mucosal surface into the mucosal tissues and vasculature. The system may be in part or in whole disposable or reusable. The system may also be deployed by directly implanting the system around or near the nervous structure or body tissue where the effect is desired.

The system will compose a device to deliver the substance to a specific area or nerve using one or more appropriate applicator(s). The applicator(s) are capable of applying the substance to the anatomic area of interest in order to achieve the desired effect on the tissue, including nerve tissue. Some embodiments may include a single or plurality of needles or microneedles to infiltrate the substance within the tissue. Other embodiments include applicators designed to topically apply the substance to the surface of a tissue. Such applicators may consist of polymers or other materials designed to release a medicine at a desired rate, the substance being impregnated through a chemical bond to the material such that its characteristics of substance release with respect to concentration, dose and time, are known and manipulated to achieve the desired effect. In other embodiments the applicator may be soaked or otherwise partially or fully saturated with the substance, or serve as a reservoir or partial reservoir for the substance, the applicator being manufactured from cotton or other absorbent organic or inorganic material, hydrogels, ionically cross-linked materials and covalently cross-linked materials, polymers such as nylon, polyether ether ketone (PEEK), polyether block amide (PEBAX), polypropylene, polyethylene, polylactic acid, polylactic co-glycolic acid, urethane, silicone, polycarbonate, PTFE, and/or other thermoplastics and/or thermosets. Said materials may have characteristics of microporous or macroporous flow channels, open or closed cell sponge structure, and/or laser drilled and/or machine drilled holes that are nano scale, micro scale, millimeter, centimeter, or larger in size.

Any of the above-described materials may be further coated with a hydrophilic or hydrophobic coating, depending on the desired manner of application. Hydrophillic coatings and hydrophobic coatings may be used to guide the flow and/or affect the resonance time of fluid containing pharmaceutical components such as anesthetics. The surface contour of the applicator may be manufactured so as to increase the surface area, for example by linear, zigzag, curved or otherwise non-linear structure to serve as retention channels for the substance. Such designs serve the purpose of having a quantity of active substance in direct contact with the mucosal surface such that the resonance time of the substance with the mucosa is sufficient to achieve the desired effect, whether such effect is achieved by diffusion of the substance across the mucosa, through intervening tissue to a nerve structure, such as the glossopharyngeal or superior laryngeal nerves, or directly to the mucosal surface to achieve a topical anesthetic effect. In some embodiments, the applicator may be an inflatable balloon, which may be perforated or porous in part or in whole.

The applicator(s) may be secured to achieve the desired effect in the desired body area via attachment to an adjacent structure or foreign body, including but not limited to an endotracheal tube, endotracheal tube securing device, bite block, nasogastric tube, orogastric tube, teeth, jaw, natural anatomic ridges, folds orifices or hollows including but not limited to the vallecula, piriform sinuses, tonsillar pillars, tonsils, adenoids, uvula, aryepiglottic folds, false or true vocal cords, hyoid bone, trachea, nasal bone, nasal turbinate, or any part of the airway or gastrointestinal mucosa, and any combination of the aforementioned. The system may be attached to said anchoring anatomic or foreign body structure via tape, glue or other adhesive, suction, clips, a pre-formed shape that facilitates attachment to a desired structure, a spring loaded, pre-stressed material or balloon of various shapes to apply pressure to keep in place, or a preformed shape that sits close to the area of action. The system may also be secured to an external body surface using similar methods applied above, even if an internal organ or mucosa surface effect is desired. Multiple attachment points to the body surface may be used. Certain embodiments may utilize a device attaching to both an internal surface. Including but not limited to mucosal surfaces, and an external body surface in order to achieve the desired effect. For instance, in order to apply the device to a cranial or other peripheral nerve in the neck, applicators may be optimally positioned internally on the airway mucosa and externally on the skin with the target nerve located between applicators. The applicator may be a sleeve-like structure surrounding a foreign body partially or entirely, including but not limited to an endotracheal tube, nasogastric tube, orogastric tube, endoscope, bronchoscope, transesophageal echocardiography probe.

The system and/or applicator(s) may be deployed into the appropriate anatomic position in various ways, including manipulation manually or with an introducer device, for instance, under direct visualization, direct laryngoscopy, fiberoptic tools to visualize the relevant area, or the like. Deployment may also occur by advancing the system and/or applicator(s) along known anatomic structures, including but not limited to the contour of the tongue to the vallecula, nasal passages, or foreign bodies with a known position within the body, including but not limited to an endotracheal tube, nasogastric tube or orogastric tube. The system and/or applicator(s) may also be placed using inflatable balloon structures, which may or may not have a pre-determined shape when inflated in order to situate the system and/or applicator(s) in the desired position. The deployment process may involve a manipulation in shape of the system or applicator(s) including but not limited to an inflatable balloon, a pre-stressed material assuming a desired shape, such as, but not limited to Nitinol, other metal alloys, polymeric materials and hydrogels, once it is deemed to be in the appropriate position. The aforementioned may be facilitated by an introducer device that allows for placement of the system and/or applicator(s) in the desired location.

In some embodiments, the applicator device or system is configured to reduce the discomfort associated with an endotracheal tube by achieving sensory, nociceptive and reflex are blockade of the glossopharyngeal and superior laryngeal nerves unilaterally or bilaterally and/or the mucosal surfaces they innervate. The applicator may be applied to the posterior tonsillar pillar and piriform sinuses as the nearest adjacent mucosal surface to the glossopharyngeal and superior laryngeal nerves, respectively. In some embodiments, the system may be additionally applied to the recurrent laryngeal nerves and/or the internal surface of the trachea in order to reduce the discomfort associated with an endotracheal tube balloon, and/or contact with the endotracheal tube itself. Blockade of the glossopharyngeal and superior laryngeal nerves, unilaterally or bilaterally, may be done to minimize sensation, nociceptive and reflex arcs associated with contact of the endotracheal tube with the airway or upper gastrointestinal tract.

The applicator(s) may be composed in part or in whole of the above-described materials, or may use a combination of such materials. The applicators may be divided into sections by insertion of a non-porous layer, so that the active substance reservoir is restricted to certain portion(s) of the applicator, while maintaining an overall shape of the applicator for correct application.

The resonance features of the system that allow a reservoir of substance(s) to be delivered by the applicator(s) of the system include but are not limited to sponge types, hydrophobic and hydrophilic channels or features, porous structures, absorptive materials, and/or capillary action. In systems with two or more applicators that branch or bifurcate from a single or multiple inflowing tubes, these features may serve the added benefit of allowing for somewhat uneven flow from the branched tubing supplying the applicators with compounds but still allow for the applicators to have a relatively even, delivery of substance to the desired area such as the mucosa of the airway. This uneven flow may occur as a result of patient's heads moving side-to-side and/or tilting, which may create a height difference at the outlets of the applicators. Additionally, including a resonance feature within the applicator segments will allow for few and/or very tiny inlet holes or pores from the bifurcated tubing segment to the applicator resonance areas. This design feature of small pores on the tubes will allow a pressure head to be built within the system that will facilitate a more equalized and even flow between two or more applicators due to a flow constricted scenario at the tiny flow outlets given the positive pressure head within the system.

In some embodiments, a solution containing topical anesthetic may be modified by a substance to alter the solution's pH, in order to alter its efficacy or to target its effect to particular nerve cell, axon type or particular tissue. Such substance may be premixed or added at the point of care through an additional reservoir or pump. Substances used in this way to modify pH may include but are not limited to sodium, bicarbonate, sodium carbonate, sodium, hydroxide, potassium hydroxide, hydrochloric acid, sulfuric acid, ammonia, and any other pH modulating reagent. This pH altering effect may increase the therapeutic activity of a pharmaceutical agent like lidocaine by creating a more basic environment that is different from the environment in which it is stored. Additional pH modulating strategies may include using electrophoresis, ionophoresis, electroporation, or other mechanisms in which an electric charge is used to increase the therapeutic activity of a substance by modulating pH of a solution containing pharmaceutical compounds and/or creating a gradient and/or pores in tissue that allows for a higher therapeutic activity of the pharmaceutical ingredient.

A conduit and/or multiple conduits with or without a bifurcation could be used to deliver pharmaceutical components to tissue in the upper airway to achieve numbing, anesthesia, or other desired therapeutic effect. A weep hole, orifice plate, restrictor orifice, restrictor valve, break away valve, pressure relief valve, flow restrictor, and/or any other means to modulate or optimize flow may be used to adjust the flow such that the device will have inbuilt operational flow patterns. Those flow patterns could allow the device to operate best in a regime of pressure and flow where a desired therapeutic effect is achieved for a dosage volume. This flow pattern modulated by a flow optimization or restriction valve may serve to restrict too much flow from going through that may cause toxic effects and/or may cause an adverse physical event, such as too much fluid in the airway and/or lungs. In the case of a low flow scenario, the device may indicate to the operator that a dose below the desired dose is being delivered. In this low flow or in a high flow scenario, a noise or other signal from cavitation, air stream or bubbles, and/or low fluid flow stream through a restricted segment of the conduit may serve to alert the operator that the device is operating outside desired parameters.

In the case of application of pharmaceutical components from the drug delivery conduit to the applicators in the device, the system may be made to operate with an off the shelf pump and/or a custom pump. Pressure ranges of operation may be in some embodiments, between about 0 psi and about 1.0 psi from the applied pump pressure. Alternative embodiments may operate at different pressure ranges, however. Additionally, in order to achieve safe effects, it may be desired to achieve a flow of less than about 20 ml per hour. Ideally for lidocaine, a topical anesthetic, a flow between about 0.5 ml and about 4 ml per hour may be achieved, depending on lidocaine concentration between 0.5% and 2%, where higher concentrations of lidocaine may demand a lower flow volume. Low concentrations of less than 1% lidocaine may be used with higher flow rates than 2 ml per hour, so long as they are not flow rates that are so high that the airway becomes flooded. To achieve a flow regime of 2-4 ml per hour of 1% lidocaine a drug delivery conduit should have an internal diameter of between about 0.02' and about 0.15". This range of delivery conduit diameters may be adjusted, depending on the size of the weep holes at different sections of the drug delivery conduit applicator sections. Ideal internal diameter may be between about 0.02" and about 0.06" for the drug delivery conduit, for example, in order to maintain a low pressure drop and also a suitable flow and maximum restricted flow. Orifice plates, restriction points, choke points, weep holes, right angles, kinks, and other design features may be included to allow for larger tubing diameters but with a series of restrictions that modulate and/or choke flow within optimal operating conditions. It may also be desired to allow for a period of high flow initially to prime the system but then break, or make impossible to re-engage, that high flow priming ability once the device is hooked up to the flow pump. This one time priming feature will allow healthcare physicians to prime the device easily with a high amount of fluid while also blocking the device from being inappropriately used, if an infusion or syringe pump is incorrectly dialed to a higher flow rate.

In most embodiments, one or more conduits supply the active substance to part or all of the applicator(s). There may be a central tubular component serving a distributive rather than reservoir function. Said tubular core may be perforated by virtue of its innate structure, for example, a microporous or macroporous structure, drilled holes or other shapes. Such perforations allow the substance to be delivered to the outer reservoir material along part or all of the applicator to target the desired anatomic areas. The tubular core may be composed of a polyether block amide polymer (PEBAX), polyether ether ketone (PEEK), polytetrafluoroethylene (PTFE), nylon, polyvinylchloride (PVC) or offer material, and may consist of a plurality of layers in order to achieve the desired properties of shape, rigidity and biocompatibility. The system may achieve action on a nerve structure via diffusion of a medication applied to an adjacent mucosal surface through the intervening tissue. Medicines may be directly impregnated onto the applicator, continuously or intermittently provided from an external source such as a controlled-rate infusion pump, syringe pump, or balloon pump reservoir. Medicines may be delivered from a reservoir, which may be part of the system or external to the system, and which is capable of delivering the medicine in a controlled continuous or bolus fashion. The device may be fitted with pressure-release valve, duck bill valve and/or other valve (or multiple valves) to achieve an intermittent effect. A pressure release valve may be connected to the system between the applicators and the pump or reservoir. In order to relieve flow and/or block flow in a scenario when the pump is malfunctioning or has been operated incorrectly such that its flow rate would be unsafe, toxic, and/or cause too much fluid to be delivered to the airway.

One of the advantages of embodiments of the systems described herein is that substance delivery may be achieved without requiring manual control of the delivery. In other words, many of the embodiments of the applicator device may be attached, via a proximal end of the conduit(s), to a mechanically driven (or "automatic") substance container or reservoir. The substance reservoir may be designed to automatically pump the substance(s) into the conduit(s) and thus into the applicator(s), thereby alleviating the need for manual advancement of the substance(s). For example, the substance delivery system described herein may include a primary central substance delivery conduit, which may be connected to a syringe, IV syringe pump, IV pump, balloon pump, IV bag, or other reservoir. In some embodiments, the reservoir may be mechanically driven (or "powered"), while in alternative embodiments, the reservoir may be manually driven. Optionally, in the mechanically driven embodiments, the reservoir portion of the system may help control the rate at which the substance(s) is delivered and/or the amount of substance(s) delivered. Alternatively, or additionally, the applicator(s) and/or the conduit(s) may control the rate and/or the amount.

In various embodiments, the primary substance delivery conduit bifurcates into two secondary conduits, at a certain angle with respect to each other to achieve the desired anatomic position. The bifurcation may be constructed in such a way as to have certain elasticity to accommodate differences in airway dimensions from individual to individual. This elasticity will spring and/or press outwardly such that direct contact and/or apposition of at least a part of the applicator in appropriate anatomical locations are achieved in the airway, especially with respect to the piriform, sinus area and/or the tonsillar pillars. The elasticity and outward springing of a two-applicator system will allow each applicator to press on the wall and correspondingly transmit a mechanical force between the two such that it helps equalize the position of the two secondary conduits and/or applicators within the upper airway.

Each secondary conduit is of an appropriate length to horizontally reach the tonsillar pillars. In the region of the tonsillar pillars, each secondary conduit may have a curve or hook shape in order to achieve apposition with the tonsillar pillars on each side. Thereafter, the secondary conduits are curved in a downward direction in order to follow the natural anatomic contours to the piriform sinuses. The applicators may be one size fits all and/or may have break away and/or adjustable portions to enable fitting in various types of airway anatomy. In addition, the applicators may or may not be configured to touch the base of the piriform sinuses or they may be free floating above the base of the piriform sinus but still in direct contact with the wall of the throat and/or tonsillar pillars. The delivery conduits may in part be inflatable balloons (which could also serve a function as an applicator) in order to account for variations in airway dimensions from individual to individual. Balloons, sponges, or other design features or applicator designs may curve or hook backwards around anatomical features like the tonsillar pillars in order to better hold the device in position from falling forward out of the mouth, unless the delivery conduits are compressed together to unhook the applicator portions from the anatomical features of the upper airway.

The applicators may be fixed at key points to the delivery conduits so as to target key anatomic areas, such as the tonsillar pillars, which are anatomically adjacent to the glossopharyngeal nerve, and the piriform sinuses, which are anatomically adjacent to the superior laryngeal nerves. The applicator-conduit construct may consist of a single, continuous material or of separate components fixed together by heat sealing, glue, adhesive tape, or other adhesive. Multiple applicators may be fixed to each of the secondary conduits, for example, one that targets the piriform sinuses, and another that targets the tonsillar pillars. The applicator may also extend beyond the dimension of the conduits. This could, for example, allow for one-size-fits-all functionality by having a compressible applicator extend beyond the terminus of the secondary conduit. This accounts for variations in the anatomic dimensions of the upper airway by virtue of its compressibility, while maintaining contact of the applicator with both the tonsillar pillar and piriform sinus.

The system and/or applicator(s) may be deployed into the appropriate anatomic position in various ways, including manipulation manually or with an introducer device under, for instance, direct visualization, direct laryngoscopy, and fiberoptic tools to visualise the relevant area. Deployment may also occur by advancing the system and/or applicator(s) along known anatomic structures, including but not limited to the contour of the tongue to the vallecula, nasal passages, or foreign bodies with a known position within the body, including but not limited to an endotracheal tube, nasogastric or orogastric tube. The system and/or applicator(s) may also be placed using inflatable balloon structures, which may or may not have a pre-determined shape when inflated in order to situate the system and/or applicator(s) in the desired position. The deployment process may involve a manipulation in shape of the system or applicator(s) including but not limited to an inflatable balloon, a pre-stressed material assuming a desired shape, such as, but not limited to Nitinol, other metal alloys, polymeric materials and hydrogels, once it is deemed to be in the appropriate position. The aforementioned may be facilitated by an introducer device that allows for placement of the system and/or applicator(s) in the desired location.

In the case of an applicator using a syringe and/or infusion pump, alternative failsafe features may or may not be added. These failsafe features include but are not limited to, a pressure relief valve, a visual cue of unacceptable flow, a flow restrictor plate or choke point, a flow restrictor small segment of tubing to limit the flow, a bypass break away valve, an audible whistle or signal cue, a light activated when bypassed fluid damps into a secondary holding container, and/or a variety of other means to alert one of improper high flow and/or halt or at least partially divert that unacceptably high flow from reaching the airway.

An exemplary device to reduce the discomfort associated with an endotracheal tube, bronchoscope or endoscope, may be used to achieve sensory, nociceptive and reflex are blockade of the glossopharyngeal and superior laryngeal nerves unilaterally or bilaterally, and/or the mucosal surfaces they innervate. The applicator may be applied to the posterior tonsillar pillar and piriform sinuses as the nearest adjacent mucosal surface to the glossopharyngeal and superior laryngeal nerves, respectively. In another instance, the device may be additionally applied to the recurrent laryngeal nerves and/or the internal surface of the trachea, to reduce the discomfort associated with an endotracheal tube balloon, and/or contact with the endotracheal tube itself. Blockade of the glossopharyngeal and superior laryngeal nerves, unilaterally or bilaterally, may be performed to minimize sensation, nociceptive and reflex arcs associated with contact of the endotracheal tube with the airway or upper gastrointestinal tract.

Figure 1C:
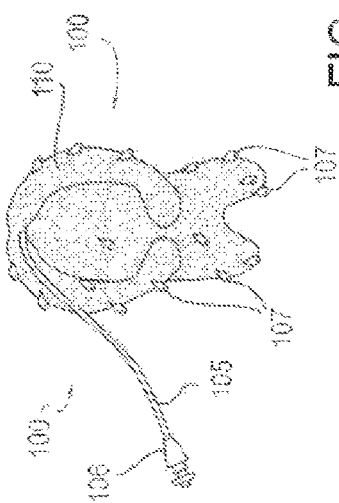
FIG. 1C is a perspective view of the applicator device of FIGS. 1A and 1B.
Figure 1A:
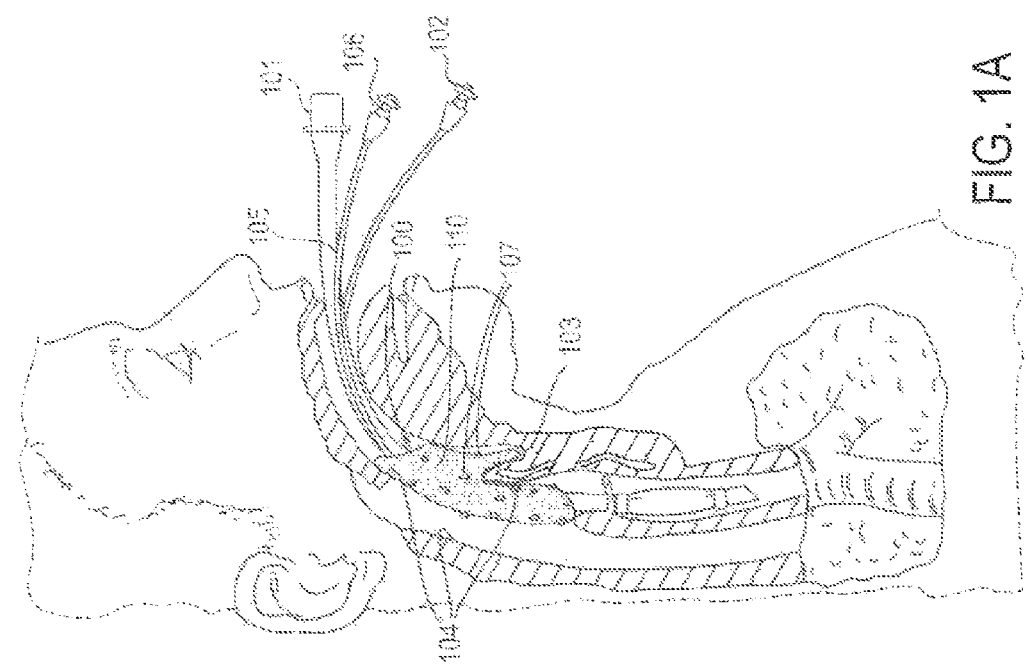
FIG. 1A is a partial cross-sectional view of a patient with an endotracheal tube in place, along with an applicator device for reducing discomfort and pain from the endotracheal tube, according to one embodiment.

FIG. 1A depicts one embodiment of an applicator device (100) deployed to decreased discomfort and pain from an endotracheal tube (101) with its cuff inflation tube (102) in situ. The applicator (110), flexible in nature, is shaped in such a contour to be seated in the vallecula (103). This facilitates anchoring in a position such that the applicator (110) is in direct or intermittent contact with key mucosal areas (104) in which discomfort from an endotracheal tube may be perceived. A conduit tube (105) is connected to the applicator (110), which is capable of delivering a substance or medicine, including but not limited to lidocaine, to achieve the desired effect. It may be connected to a drug infusion pump or other reservoir using a connector (106). The surface of the applicator (110) contains a material through which the substance or medication (107) is wept out from the posterior and lateral surfaces.

FIG. 1B illustrates the applicator device (100) coupled with the endotracheal tube (101). The applicator device (100) may include the applicator (110), the conduit (105) and the connector (106). (Alternatively, the "applicator device (100)" may be referred to as an "applicator system," "substance delivery device" or "substance delivery system.") A contoured portion (108) of the applicator (110) may facilitate loose attachment around the endotracheal tube (101) to facilitate accurate deployment and maintenance of position to obtain the desired clinical effect.

FIG. 1C illustrates the applicator (100), composed of a material capable of weeping out medication (107, arrows) delivered from a medication source via the delivery conduit (105) and connector (106).

Figure 2A:
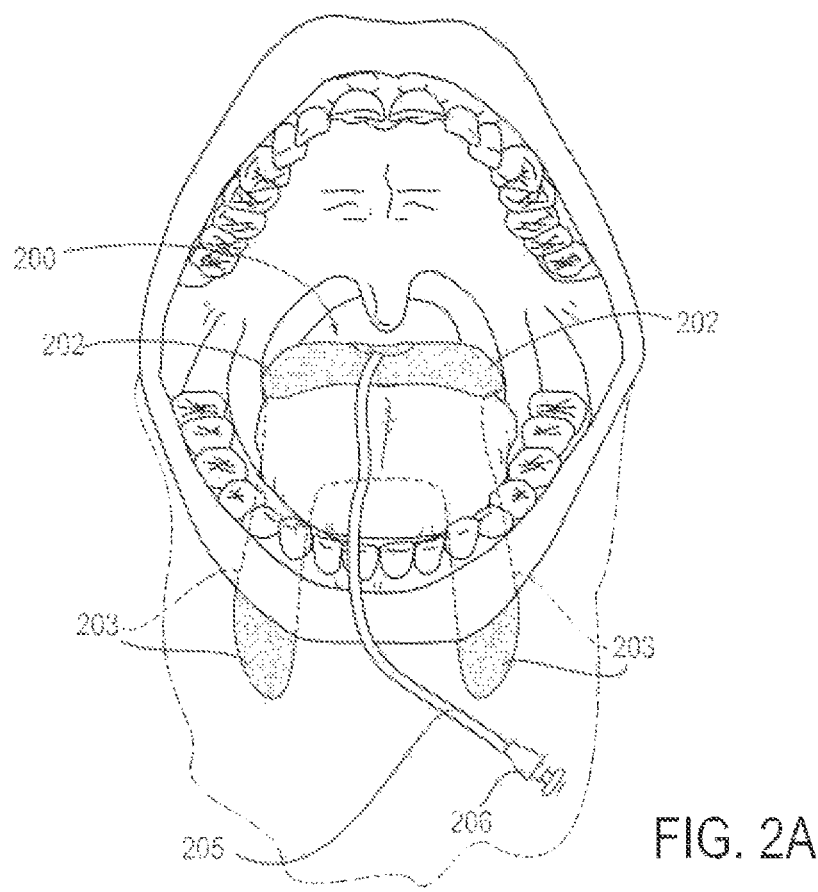
FIG. 2A is a front view diagrammatic representation of a patient's mouth and upper airway, with an applicator device in position to achieve neurosensory blockade of the glossopharyngeal and superior laryngeal nerves, bilaterally, according to an alternative embodiment.

FIG. 2A illustrates an alternative embodiment of an applicator device (200), with applicators (201) situated in the oropharynx and hypopharynx, such that it is in contact with the posterior tonsillar pillars (202) bilaterally, and the piriform sinuses (203) bilaterally. A substance or medication, including but not limited to lidocaine, may be delivered via a conduit (205), which can be attached to an infusion pump or other reservoir via a connector (206). The surface (204) of the applicators (201) is designed such that the delivered substance or medicine can be made to weep through the entire surface (204).

Figure 2B:
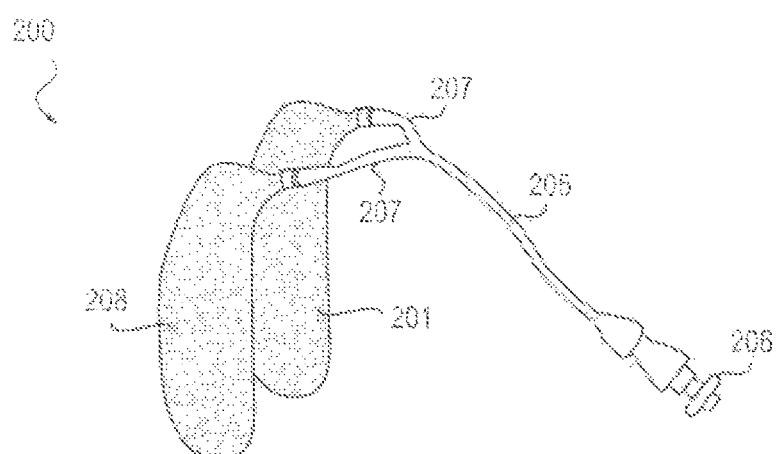
FIG. 2B is a perspective view of the applicator device from FIG. 2A, including a delivery conduit.

FIG. 2B shows the applicator device (200) outside of the mouth, including the applicators (201) attached to the delivery conduit (205) and connector (206). The strut structure (207) is sized in such a way that the applicator touches the desired submucosal tissue. The angled contour (208) of the applicator (201) is designed to facilitate placement of the applicator (201) in the oropharynx and hypopharynx, and facilitate a natural resting position for the applicator (201) once deployed. The strut structure (207) may also provide an outwardly directed force, to push the applicators (201) laterally outward to contact opposed, lateral surfaces of the inner wall of the airway, approximately 180 degrees apart from each other.

Figure 3A:
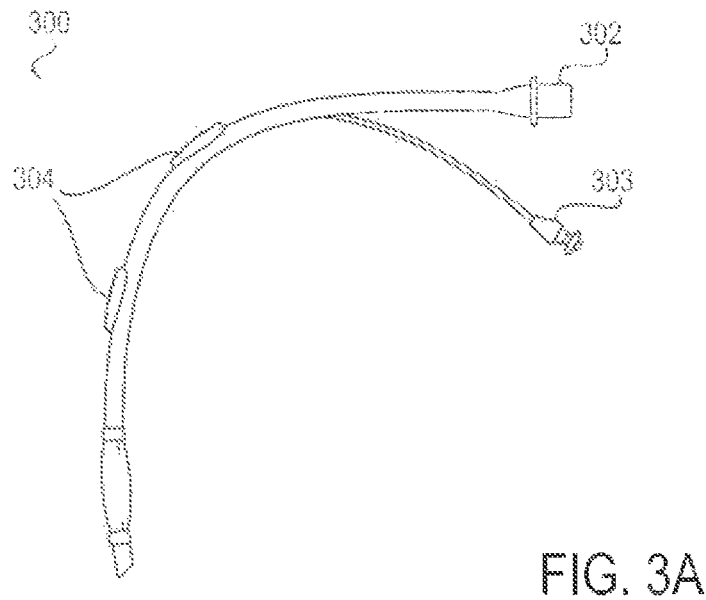
FIG. 3A is a side view of an endotracheal tube fitted with components to facilitate attachment of an applicator device, according to one embodiment.
Figure 3B:
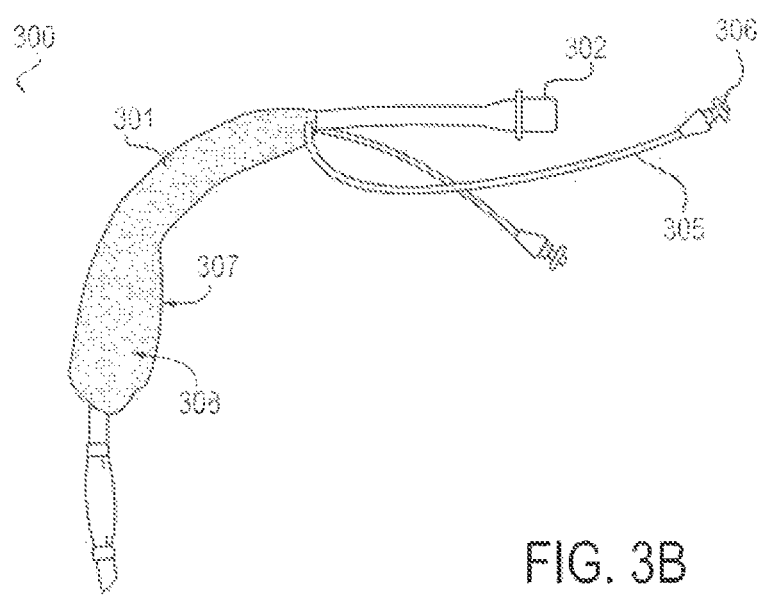
FIG. 3B is a side view of the endotracheal tube of FIG. 3A, with the applicator device attached, according to one embodiment.

FIGS. 3A and 3B illustrate another embodiment of an applicator device (300), which is configured to fit over an endotracheal tube (302) in a sleeve-like fashion. FIG. 3A depicts the endotracheal tube (302) and cuff inflation tube (303), which has been fitted with components (304) (or "surface features") to facilitate attachment of the applicator device (300).

FIG. 3B depicts the applicator device (300) advanced over the endotracheal tube (302) and secured to it using the aforementioned attaching components (304). The applicator device (300) includes a sleeve-like applicator (301), a conduit (305) fluidly attached to the applicator (301), and a connector (306) at the proximal end of the conduit (305). The applicator device (300) also includes a contour (307) that facilitates its seating in the vallecula, in order to maintain the device (300) in a desired position in the airway. The applicator surface (308) encloses a portion of the endotracheal tube (302) that may be in constant or intermittent contact with structures of the airway. The surface (308) may be composed of a material that allows weeping of a medicine or substance, including but not limited to lidocaine, designed to reduce sensation and discomfort in the airway. The medicine or substance is delivered via the conduit (305) connected to an infusion pump or other reservoir via the connector (306).

Figure 4:
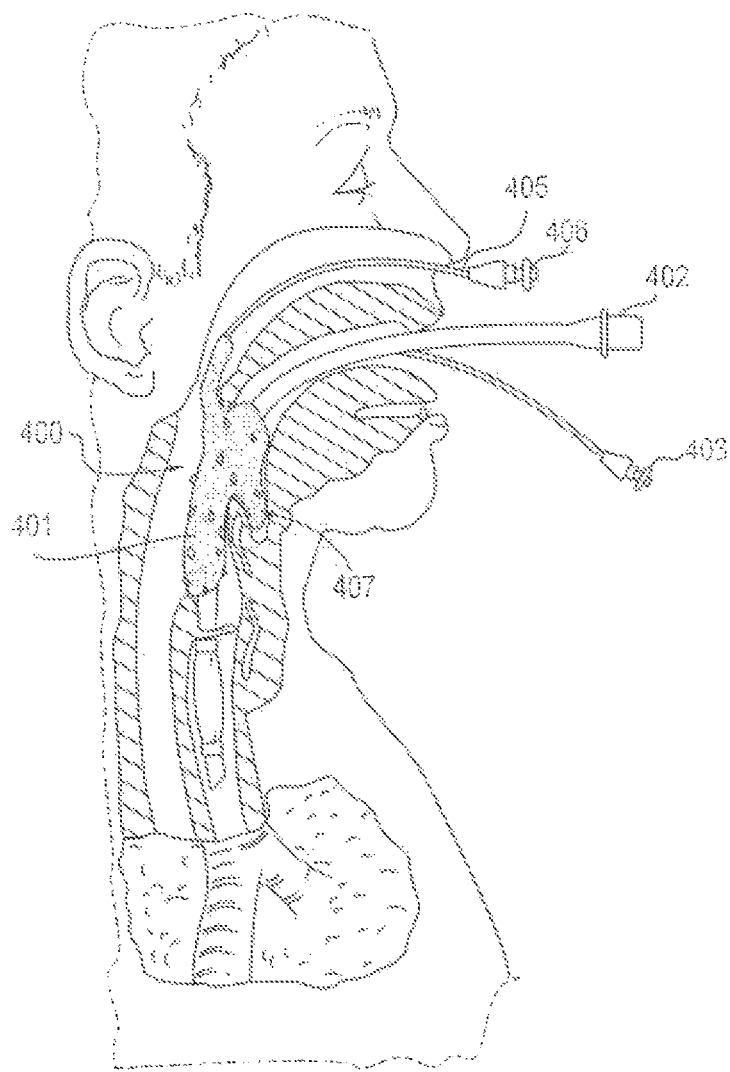
FIG. 4 is a partial cross-sectional view of a patient with an endotracheal tube in place, along with an applicator device for reducing discomfort and pain from the endotracheal tube, according to one embodiment in which the applicator device is delivered transnasally.

FIG. 4 illustrates another embodiment of an applicator device (400), in which the applicator (401) is deployed into the airway transnasally. The delivery conduit (405) and connector (406) traverse the nasal passage and exit through the nose. The applicator (401) is composed of a flexible and/or expandable material, such mat it may traverse the nasal passages during deployment and then resume its desired shape. The contour (407) of the applicator (401) allows for it to be seated in the vallecula. The surface of the applicator (401) is composed of a material capable of weeping a medicine or other substance delivered from the conduit (405) onto areas of the oropharynx and hypopharynx, where discomfort from the endotracheal tube (402), with its cuff inflation tube (406), may be perceived.

Figure 5:
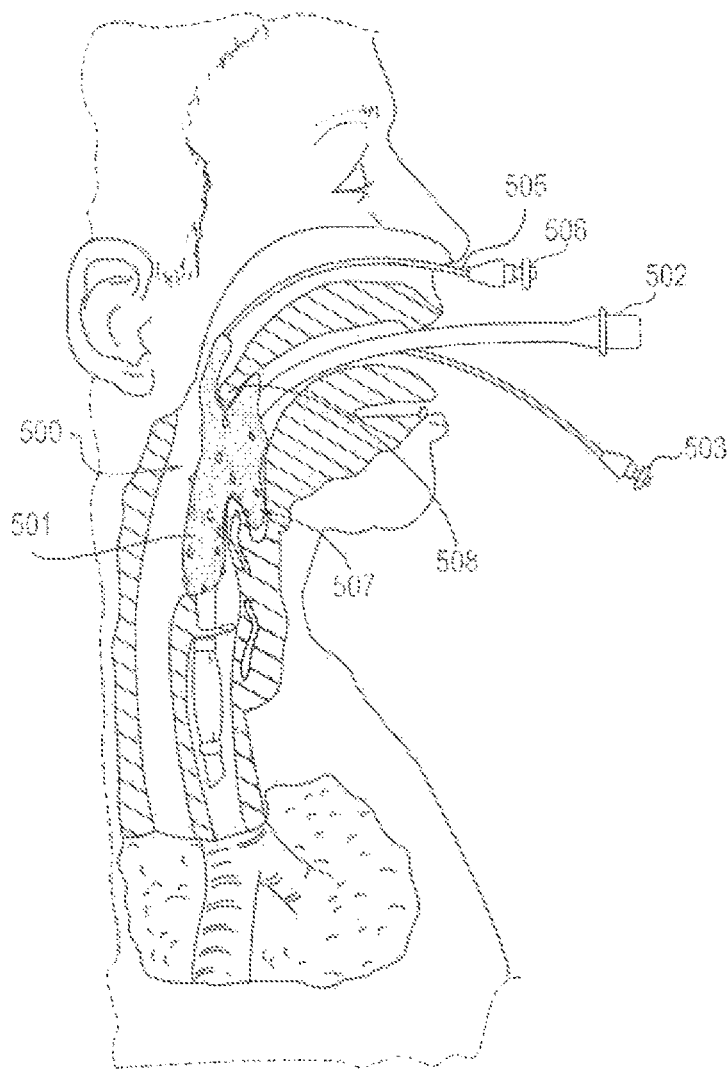
FIG. 5 is a partial cross-sectional view of a patient with an endotracheal tube in place, along with an applicator device for reducing discomfort and pain from the endotracheal tube, according to an alternative embodiment in which the applicator device is delivered transnasally.

FIG. 5 illustrates another embodiment of an applicator device (500), in which the applicator (501) is deployed transnasally. The delivery conduit (505) and connector (506) traverse the nasal passage and exit through the nose. The applicator (501) is composed of a flexible and/or expandable material such that it may traverse the nasal passages during deployment and then resume its desired shape. The contour (507) of the applicator (501) allows for it to be seated in the vallecula. The surface of the applicator (501) is composed of a material capable of weeping a medicine or other substance delivered from the conduit (505) onto areas of the oropharynx and hypopharynx where discomfort from the endotracheal tube (502), with its cuff inflation tube (506), may be perceived, including the soft palate (508).

Figure 6A:
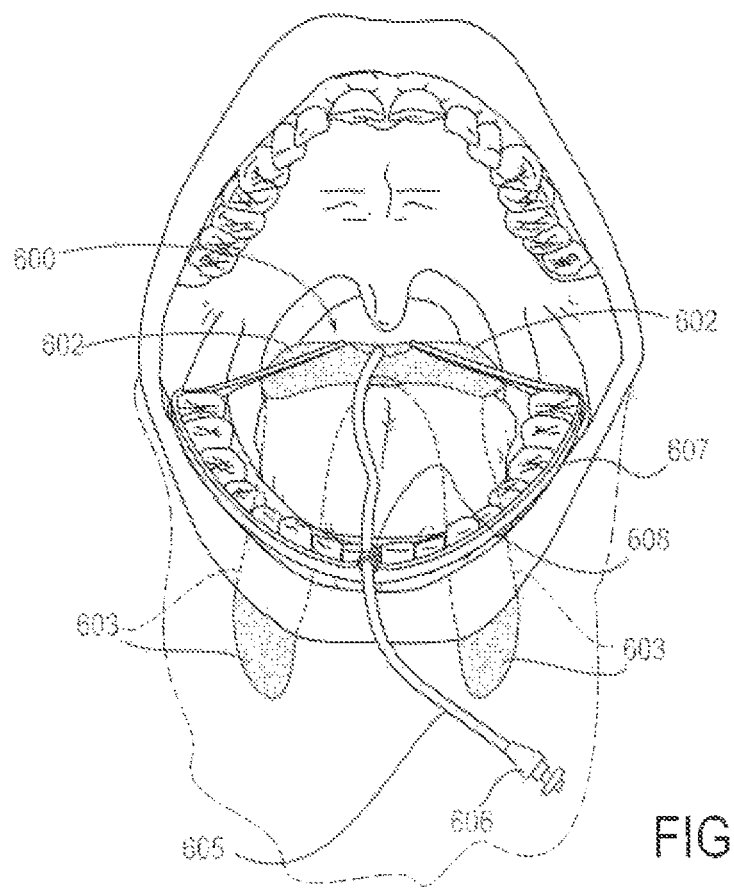
FIG. 6A is a front view diagrammatic representation of a patient's mouth and upper airway, with an applicator device including a retaining device in position to deliver a medicine or substance to the posterior tonsillar pillars and piriform sinuses bilaterally, and thus effect neurosensory blockade of the glossopharyngeal and superior laryngeal nerves bilaterally, according to an alternative embodiment.
Figure 6B:
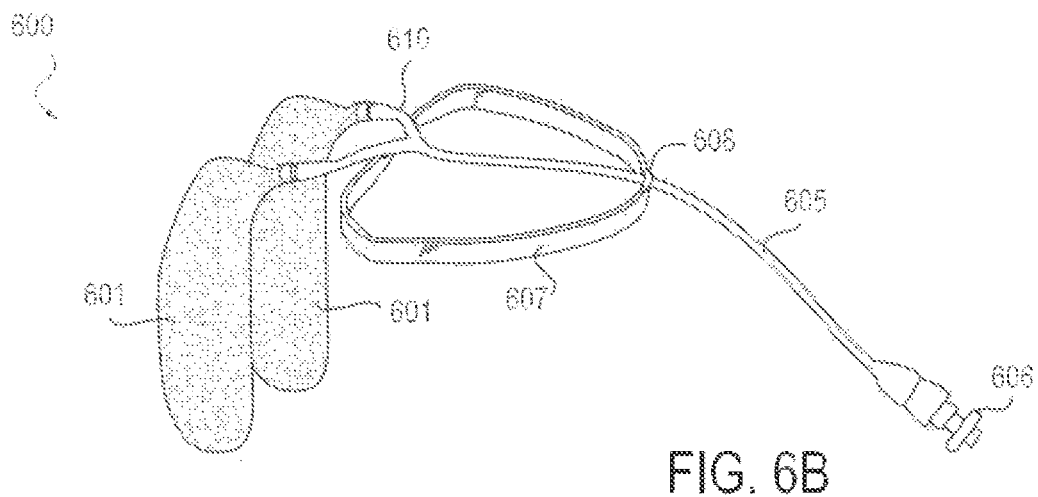
FIG. 6B is a perspective view of the applicator device of FIG. 6A.

FIGS. 6A and 6B illustrate another embodiment of an applicator device (600), including bilateral applicators (601), situated in the oropharynx and hypopharynx, such that they are in contact with the posterior tonsillar pillars (602) bilaterally and the piriform sinuses (603) bilaterally. A substance or medication, including but not limited to lidocaine, is delivered to the applicators (601) via a conduit (605), which can be attached to an infusion pump or other reservoir via a connector (606). The surface (604) of the applicators (601) is designed such that the delivered substance or medicine can be wept through its entire surface (604). A retaining device (607) wraps around the lower dental plate in order to secure the applicator in the desired position. The delivery conduit (605) is also secured (608) to the retaining device (607)

FIG. 6B depicts the applicator device (600) outside of the mouth, including the applicators (601) attached to the delivery conduit (605) and connector (606). The strut structure (610) is sized in such a way that the applicators (601) touch the desired submucosal tissue. The angled contour (609) of the applicators (601) is designed to facilitate placement of the applicators (601) in the oropharynx and hypopharynx, and facilitate a natural resting position for the applicators (601) once deployed. The retaining device (607), which also secures the delivery conduit (608) is attached to the applicators (601).

Figure 7A:
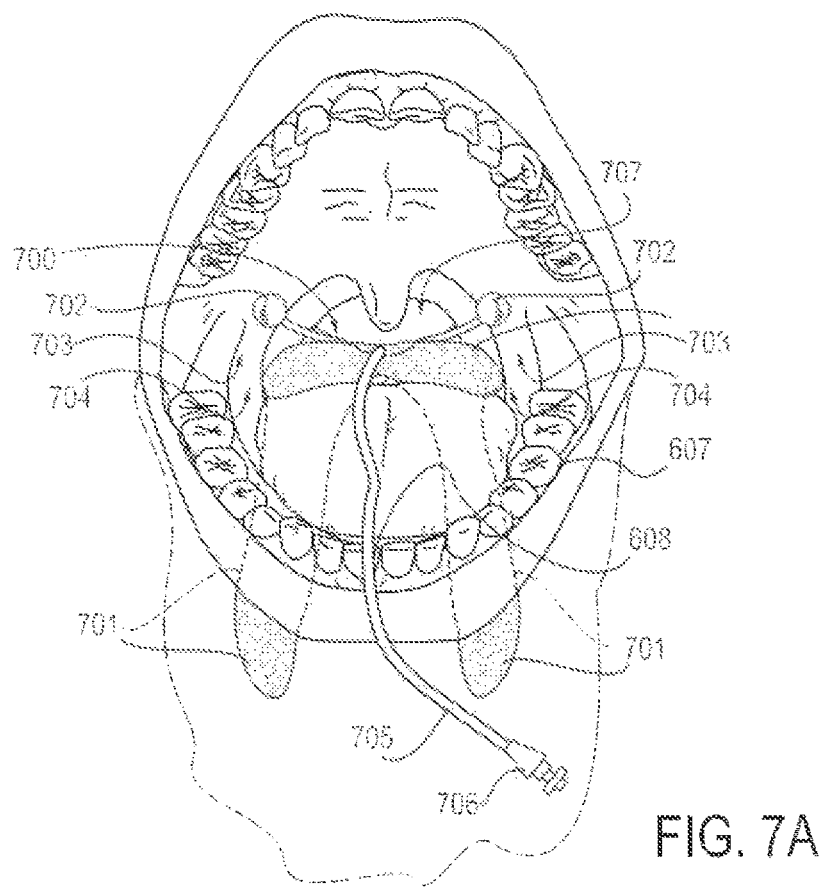
FIG. 7A is a front view diagrammatic representation of a patient's mouth and upper airway, with an applicator device including a clamp in position, according to an alternative embodiment.
Figure 7B:
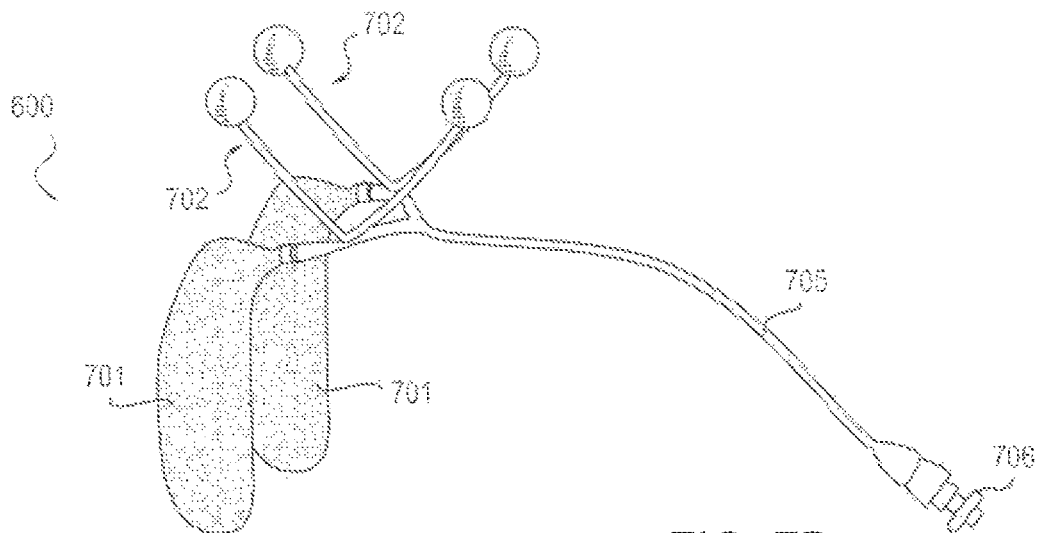
FIG. 7B is a perspective view of the applicator device of FIG. 7A.

FIGS. 7A and 7B illustrate another embodiment of an applicator device (700), including two applicators (701) for reducing discomfort in the throat and/or airway. Applicators (701) are inserted into the throat such that they will contact the tonsilar pillars and/or surrounding anatomical structures of the throat (704). Pharmacological compounds and/or energy can be applied through any contact of the applicators (701) or a surrounding medium such as air or mucus that makes contact with the applicators (701) also makes contact with the tissue wall of the airway or throat (707). The pharmacological compounds and/or energy are delivered to the applicators (701) through a connector (706) and a delivery conduit (705). The applicators (701) may be anchored in place by clamps (702), which are attached to folds or other anatomical features (703) which facilitate such attachment. The pictured embodiment is merely one exemplary embodiment, with two applicators (701) that are separate and contacting in the tonsilar pillar region (704). Alternative embodiments may be configured so that there is one continuous applicator (701) along the entire region of the epiglottis and/or tonsilar pillar (704). Also, the clamps (702) may not be the only such means to connect the device to an anatomical tissue structure. Other connection means, such as but not limited to glue, adhesive, pins, needles, Velcro, hooks, static charge, opposing side pressure, springs, inflated balloons, screws, and the like, may facilitate proper placement within anatomical structures. Additional means for inserting and applying a sensory altering effect could be facilitated by simple changes in geometry of the device, according to various alternative embodiments.

Figure 8:
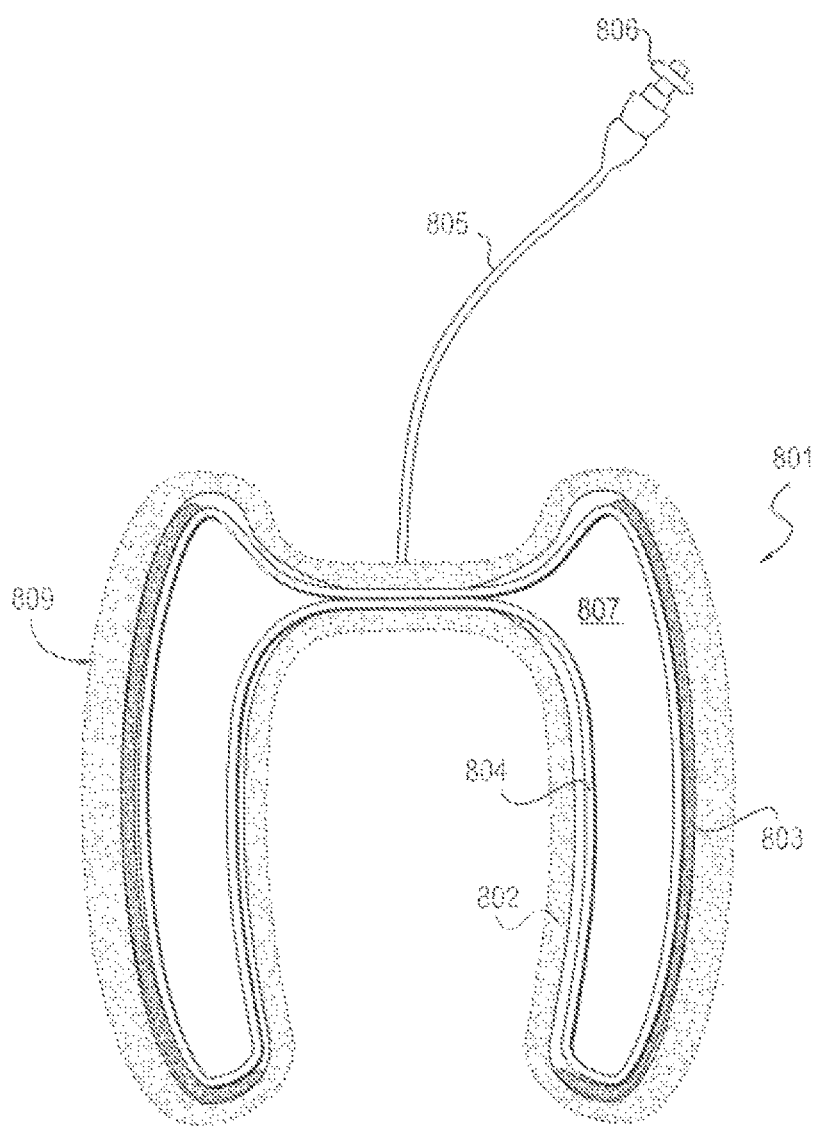
FIG. 8 is a front view of an applicator device for reducing sensation in the throat or airway, according to another embodiment.

FIG. 8 illustrates another embodiment of an applicator device (801) for reducing discomfort in the airway. Pharmacological compounds are delivered to the applicator (801) through a connector (806) and a delivery conduit (805). The pharmacological compounds diffuse throughout the device into the applicator portions (802) of the device (801), such that they are applied through the surface pores (809) of the applicator portions (802) to the surrounding tissue. In this exemplary version of the system, a flexible ring component with shape memory (804) is used to form the applicator (801) to the correct shape. An internal segment (807) of the device (801) may be filled with air or other medium in order to allow for flexible movement of the applicator (801). In order to keep the shape memory component (804) from interacting with a pharmacological compound in the applicator portions (802), a barrier component (803) may be used. This barrier component (803) may facilitate flow of the pharmacological agents around the applicator (801). Using a memory shape component (804) may also be useful for an applicator (801) that applies an electric energy or other force. In various alternative embodiments, alternative versions of sensory suppression or improving agents for treatment of discomfort may be used.

Figure 9:
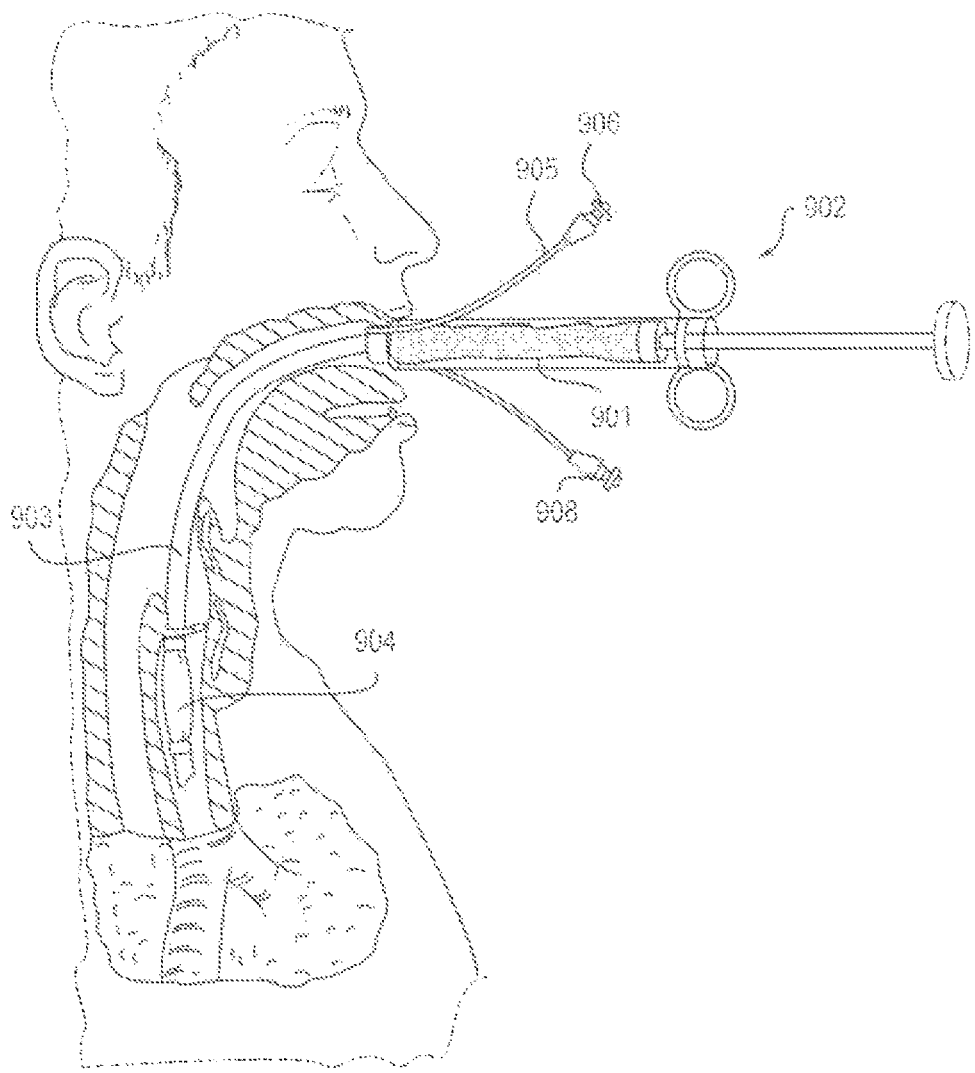
FIG. 9 is a partial cross-sectional view of a patient with an endotracheal tube in place, illustrating a device for facilitating placement of an applicator device in a desired position in the airway, according to one embodiment.

FIG. 9 illustrates one embodiment of a delivery device (902) for delivering an applicator device (901) to the appropriate position in the airway (903). Such a delivery device (902) will facilitate delivery while an endotracheal tube (904) is already inserted. The endotracheal tube (004) may also have a balloon inflation attachment (908). A delivery conduit (905) and a delivery connector (906) will facilitate delivery of the pharmacological component, electronic component and/or other force necessary to create an anesthetic effect on the airway and/or throat. This delivery takes place through a direct or indirect contact of the applicator (901) with the airway or throat.

Figure 10:
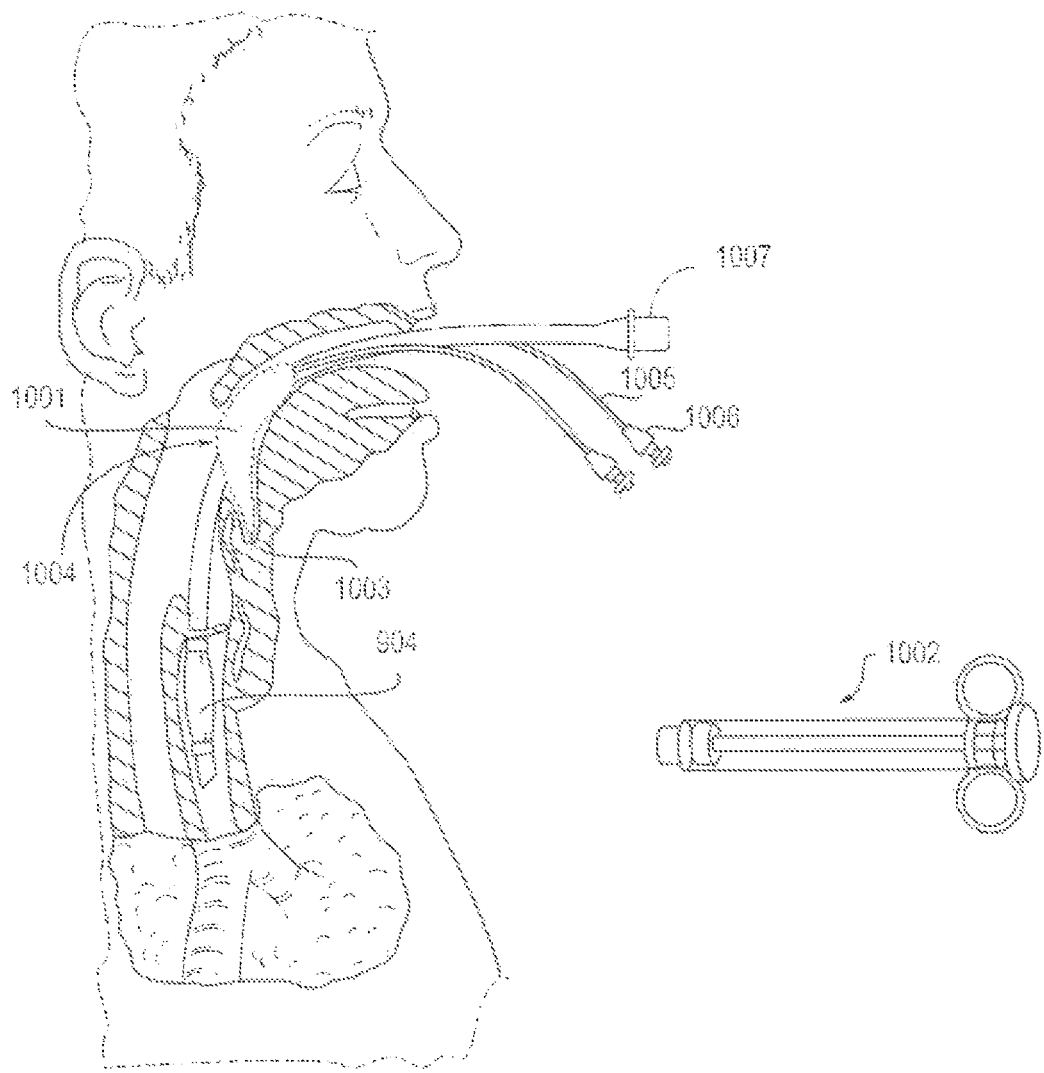
FIG. 10 illustrates the placement device of FIG. 9 removed from the patient and the applicator device in place within the patient.

FIG. 10 shows a delivery device (1002) having deployed the system and applicator (1004) into the airway or throat. An applicator device (1004) is positioned to fit around an endotracheal tube (1007), such that it can help reduce the discomfort associated with having an endotracheal tube (1007) inserted through the airway. Some key features of the airway that may be anesthetized in whole or in part are the soft pallet (1001), base of tongue (1008) and vallecula (1003). The system may include a delivery conduit (1005) and a connector (1006) that delivers a pharmacological substance to the applicator (1004).

Figure 11:
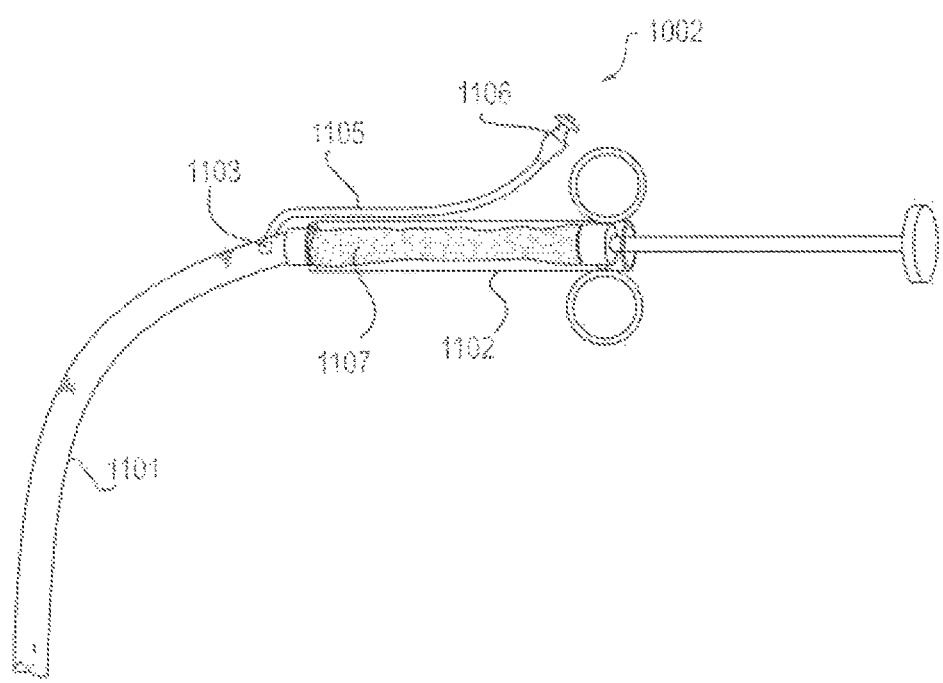
FIG. 11 is a side view of a device for facilitating placement of an applicator device with a curved insertion port that enables better access to deep airways features, according to one embodiment.

FIG. 11 illustrates an alternative embodiment of a delivery device (1102), with an extended and curved guide conduit (1101). The system and applicator (1107) is configured to be delivered into the airway while the delivery conduit (1105) and connector (1106) are positioned such that they are not inserted into the airway when the applicator (1107) is inserted into the airway. One such way that this may be accomplished is through a hole or slot (1103) that holds the delivery conduit (1105).

Figure 12A:
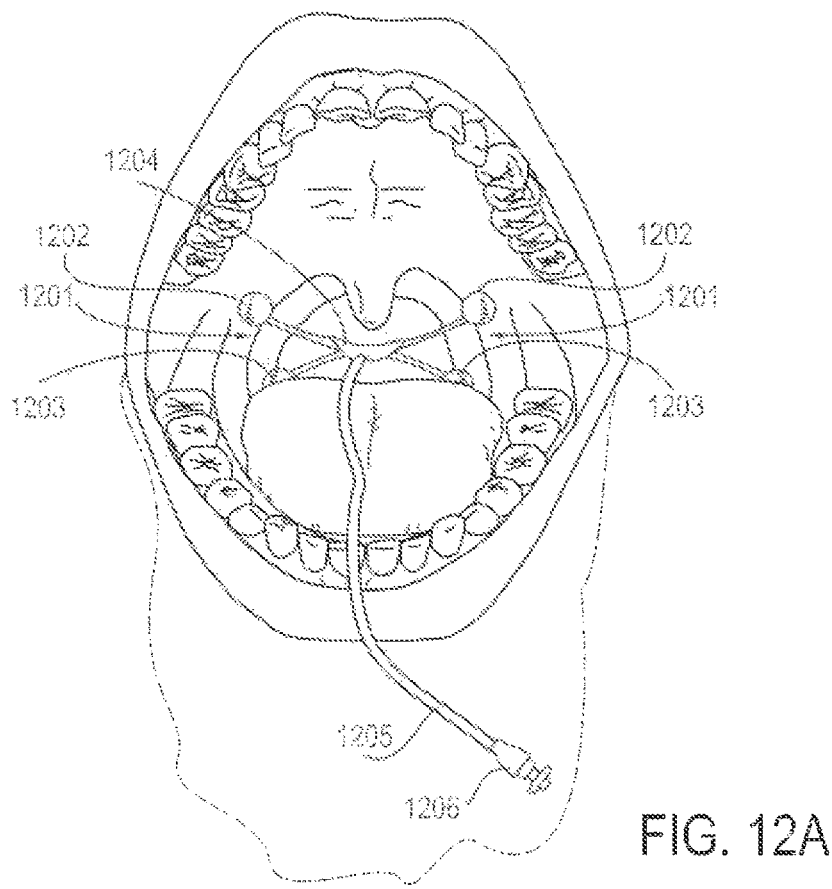
FIG. 12A is a front view diagrammatic representation of a patient's mouth and upper airway, with an applicator device including attachment means in the mouth and airway for delivery of an energy to reduce discomfort, according to one embodiment.

FIG. 12A depicts another exemplary system. The applicator device (1204) is shaped such that it has two, symmetrically shaped clip structures, each with an anterior arm (1202) and a posterior arm (1203), their positions being relative to the tonsil and tonsillar pillars bilaterally (1201). The posterior arm (1203) terminates with a sphere resting at the base of the posterior tonsillar. The terminus contains an orifice through which a substance or medicine may be delivered to the adjacent mucosal tissue, and subsequently absorbed into the region of the glossopharyngeal nerve bilaterally by virtue of the nerve's proximity to the posterior tonsillar pillar, in order to achieve sensory nervous blockade in the distribution of the glossopharyngeal nerves bilaterally. The medicine or substance is delivered via a conduit (1205) connected to an infusion pump or other reservoir via a connector (1206).

Figure 12B:
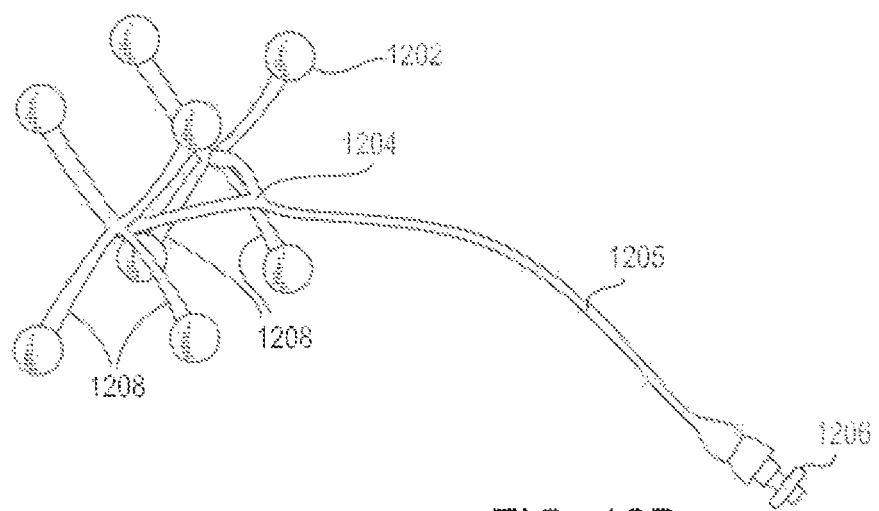
FIG. 12B is a perspective view of the applicator device of FIG. 12A.

FIG. 12B depicts an alternate exemplary applicator (1204), containing four, symmetrically shaped clip structures, each with two arms, for instance an anterior, superior arm (1202) and a posterior, inferior arm (1208). The posterior, inferior arms (1208) are designed to rest al the base of the tonsillar pillars bilaterally, and the sizing of the support strut (1209) is appropriately wide to ensure that the distal, spherical end is in contact with the mucosal tissue. The distal, spherical ends of the posterior, inferior struts contain orifices suitable for delivering a medicine or substance delivered via a conduit (1205) from an infusion pump or other reservoir attached via a connector (1206). The other clips illustrated secure the device at the level of the tonsillar pillars through direct contact with surrounding mucosal surfaces.

FIG. 13A depicts an exemplary system (1300) for decreasing discomfort and pain from an endotracheal tube (1302). An applicator device (1308), flexible in nature, is shaped in such a contour (1310) to be seated in the vallecula (1303). This facilitates anchoring in a position such that the applicator (1308) is in direct or intermittent contact with key hypopharyngeal mucosal areas in which discomfort from an endotracheal tube (1302) may be perceived and the soft palate (1304). The posterior and lateral surfaces of the applicator (1308) are composed of an electrically conductive material, capable of delivering electrical energy to the mucosal surface. An electrical conduit (1305) is connected to the applicator, which is capable of delivering an electric current of a certain character to achieve the desired effect of reduced sensation and discomfort to key mucosal areas. It is connected to a controller box (1301) via an electric cord (1307), which modulates the delivered electricity.

FIG. 13B depicts the exemplary applicator (1310) in relation to the endotracheal tube (1302). The contour of the applicator (1310) facilitates loose attachment around the endotracheal tube to allow accurate deployment and maintenance of position to obtain the desired clinical effect. The contour of the base (1311) allows for the applicator the rest in the piriform sinuses bilaterally (1311). The posterior and lateral surfaces of the applicator (1308) are composed of an electrically conductive material capable of delivering energy to the mucosal surface. An electrical conduit (1305) is connected to the applicator, which may be connected to a source of electricity via a connector (1306).

FIG. 13C depicts the exemplary applicator (1310), the posterior and lateral surfaces of which are composed of an electrically conductive material (1308). Electricity may be delivered to the applicator via an electrical conduit (1305)

connected to a source of electricity via a connector (1306). The contour of the base (1311) allows the applicator (1310) to rest in the piriform sinuses bilaterally.

Figure 14:
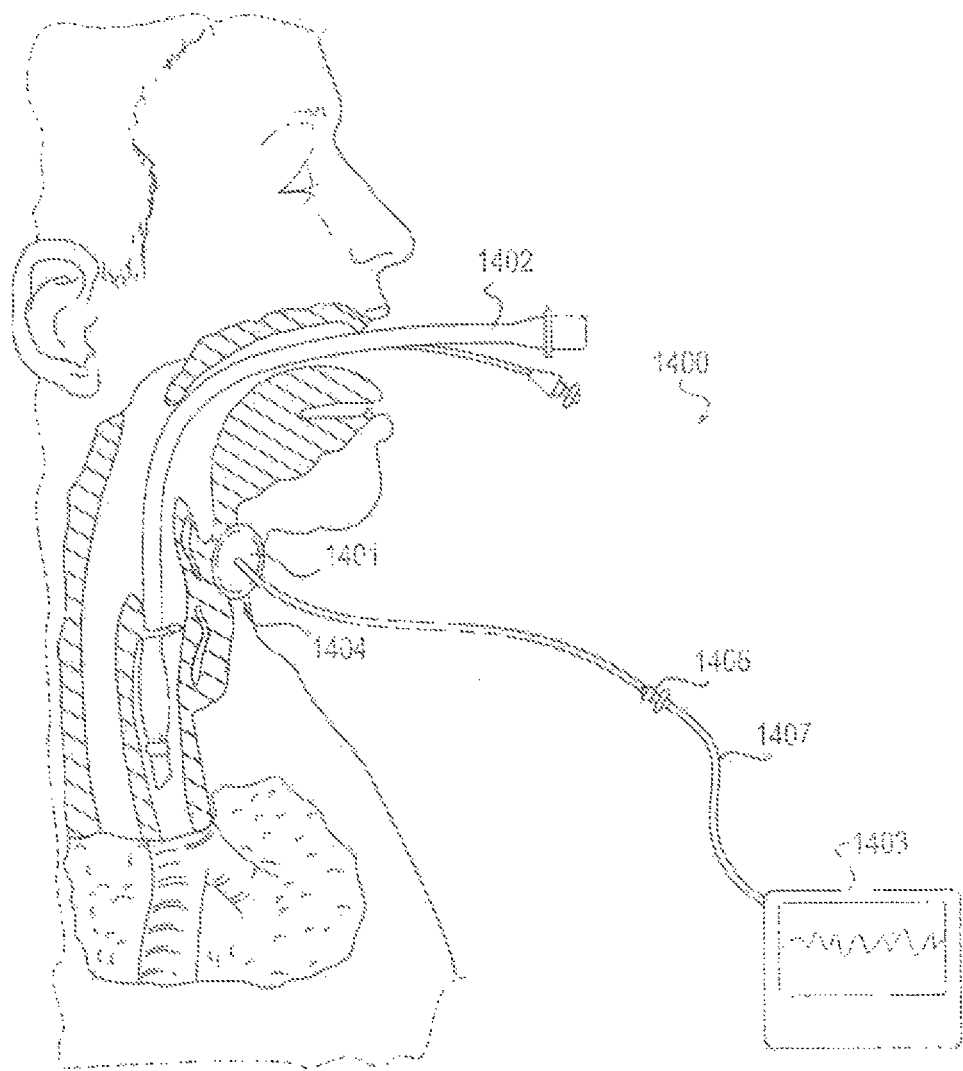
FIG. 14 is a partial cross-sectional view of a patient with an endotracheal tube in place, along with an applicator device for reducing discomfort and pain from the endotracheal tube through externally applied means, according to another alternative embodiment.

FIG. 14 depicts another exemplary system (1400) designed to reduce discomfort associated with an endotracheal tube (1402). Two external electrode assembly pads (one pad drawn, 1401) are attached to the on each side of the neck at the level of the hyoid bone (1404). The electrode pads (1401) are capable of delivering an electric energy to the tissue of the neck, including nervous tissue providing sensory innervation to the mucosal surfaces of the airway. Electricity is supplied by an electrical conduit (1405) terminating in a connector (1406), which can be attached to a control box (1403) via an electric cord (1407).

Figure 15:
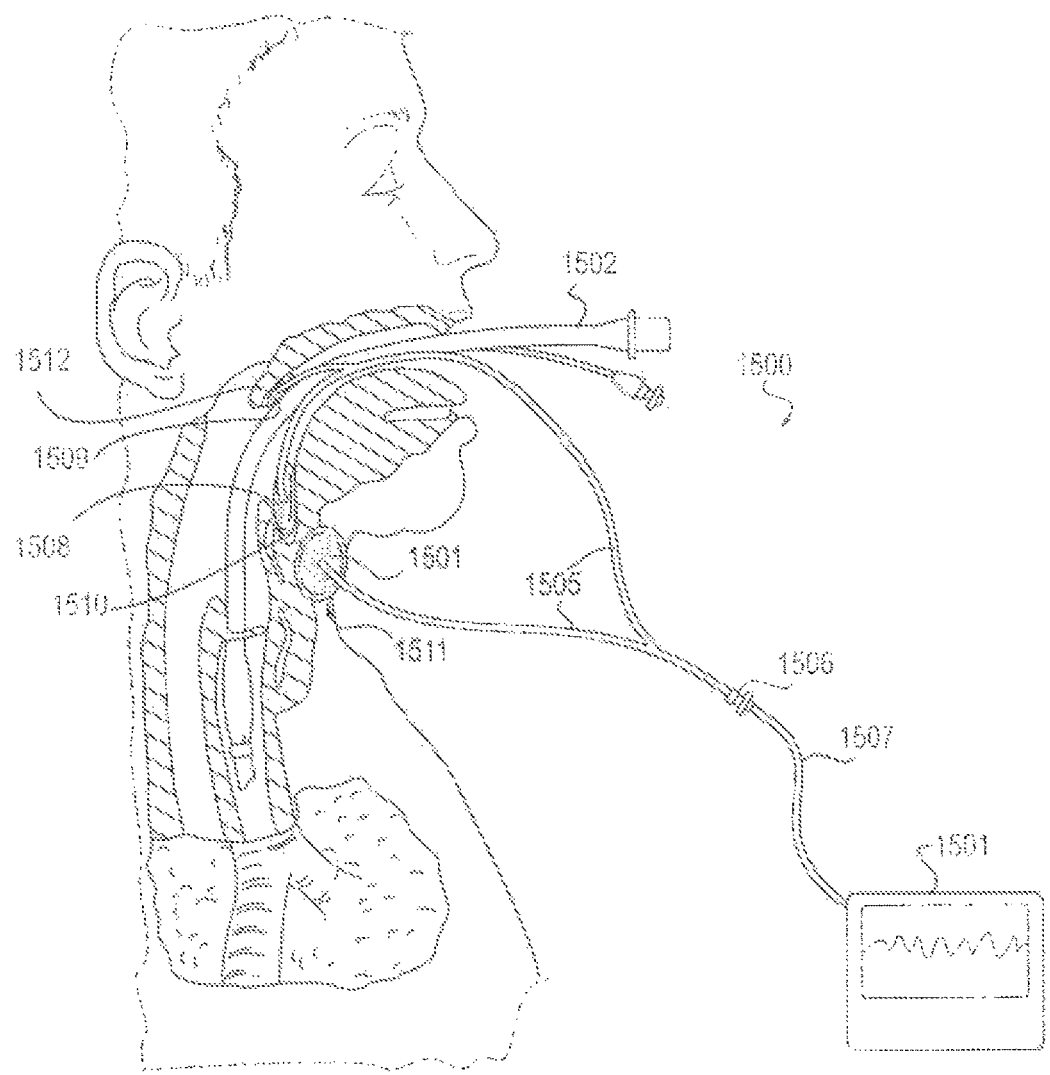
FIG. 15 is a partial cross-sectional view of a patient with an endotracheal tube in place, along with an applicator device for reducing discomfort and pain from the endotracheal tube through internally and externally applied means, according to another alternative embodiment.
Figure 17A:
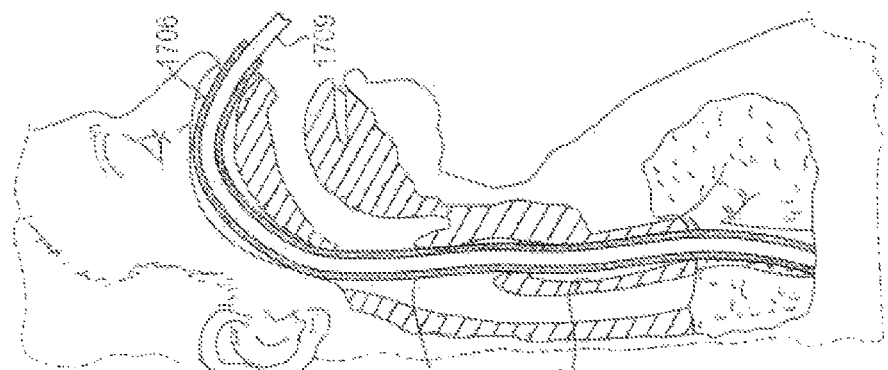
Figure 17A:
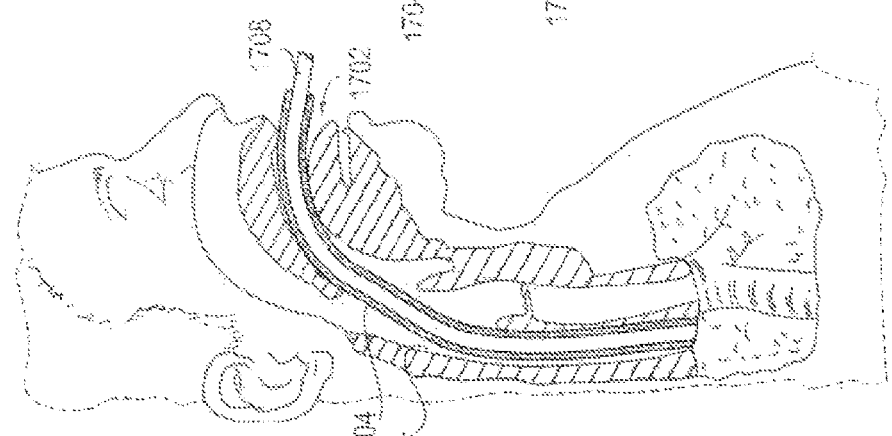
Figure 17A:
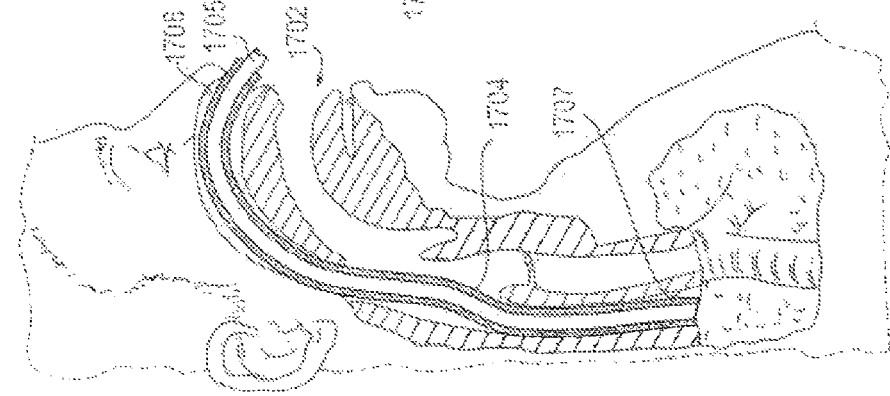
Figure 17A:
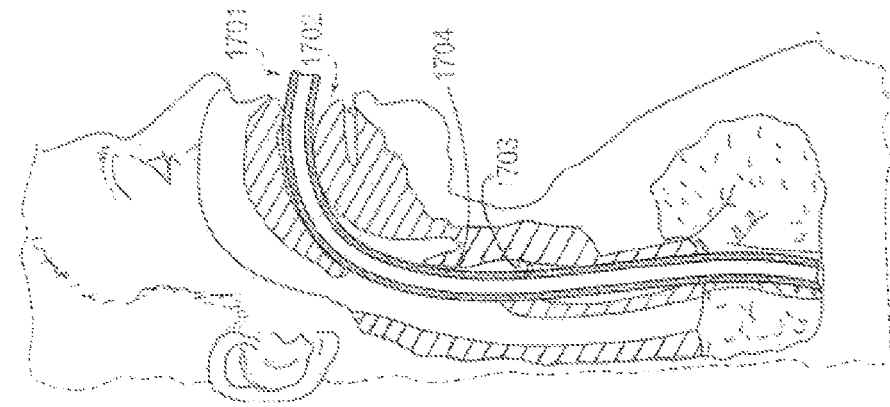

FIG. 15 depicts another exemplary system (1500) designed to reduce discomfort associated with an endotracheal tube (1502). Two external electrode assembly pads (one pad drawn, 1501) are attached to the on each side of the neck at the level of the hyoid bone (1511). An additional electrode (1509) is placed on the soft palate (1512), and an additional electrode (1508) is seated at the vallecula (1510). These are capable of delivering electric energy to the tissue of the neck, internal mucosal surfaces, and nervous tissue providing sensory innervation to the mucosal surfaces of the airway. Electricity is supplied by an electrical conduit (1505) terminating in a connector (1506) which can be attached to a control box (1501) via an electric cord (1507).

FIG. 16A depicts another exemplary system (1600) designed to reduce discomfort associated with an endotracheal tube (1602). Two external electrode assembly pads (one pad drawn, 1604) are attached to the on each side of the neck which is capable of delivering an electric energy to the tissue of the neck, including nervous tissue providing sensory innervation to the mucosal surfaces of the airway (1608). Such electrodes may be placed on the internal mucosal surface of the airway, as in FIG. 15. A conduit is capable of delivering and electric current and additionally has a lumen for delivery of a substance or medicine used to reduce sensation or discomfort, including but not limited to lidocaine. This lumen may be attached to a drug delivery pump or other reservoir via a connector (1606). The electrical component of the conduit may be connected to a control box via a connector (1607).

FIG. 16B depicts an alternate electrode (1604), such as that described in FIG. 15 and FIG. 16, in which electrical current is delivered to the skin or mucosal surface via microneedles (1603), and electricity is supplied via an electrical conduit (1605).

FIG. 16C depicts an alternate electrode (1604), such as that described in FIG. 15 and FIG. 16, in which electrical current is delivered to the skin or mucosal surface via a flat surface, flush with skin or mucosal surface, and electricity is supplied via an electrical conduit (1605).

FIG. 17 depicts a series of alternate exemplary applicator configurations designed to reduce the discomfort, pain, sensation and/or induction of a neurologic reflex associated with a foreign object in the airway and/or gastrointestinal tract, in which the applicator is a sheath applied over all or part of the foreign body. FIG. 17A depicts a foreign object (1701), for example an endotracheal tube, suction catheter, bronchoscope or laryngoscope, entering the mouth (1702), and advancing through the airway (1703). A sheath (1704) encloses all, or a portion of, the foreign object, and is capable of delivery the desired substance, medicine, energy and/or other effect described in the above-mentioned drawings and/or descriptions. FIG. 17B depicts a foreign object (1705), including but not limited to a nasogastric tube or pH monitor entering the airway through the nose (1706) and passing through the airway into the gastrointestinal tract (1707). The abovementioned sheath (1704) is similarly enclosing the foreign object. FIG. 17C depicts a foreign object (1708), including but not limited to a transesophageal echocardiography probe, orogastric tube, pH probe, or endoscope entering the mouth (1702) and passing through the airway into the gastrointestinal tract (1707). The abovementioned sheath (1704) similarly encloses the foreign object. FIG. 17D depicts a foreign object (1709), including but not limited to an endotracheal tube, bronchoscope or laryngoscope, entering the nose (1706) and passing through the airway. The abovementioned sheath (1704) is similarly enclosing the foreign object. The foreign object, in addition to the abovementioned, may be any other diagnostic or therapeutic device. Relevant attaching conduits, connectors, and other ancillary devices are not depicted in these drawings. The sheath may enclose a portion of, or the entire length of, the foreign object. Similarly, the sheath may enclose a portion or all of the entire circumference, or in the case of linear dimensions, the length and/or width of the foreign object. The sheath itself may be of various configurations, including but not limited to, a continuous, needle-lined, wire-lined, smooth, woven, perforated and/or mesh structure(s). The sheath may freely slide over parts or all of the foreign object, or may be attached view glue, adhesive, pins, needles, Velcro, hoods, static charge, pressure generated by any means, springs, inflated balloons, suction, clips, magnetic force, supports touching anatomical structures, or any combination of the above.

Figure 18B:
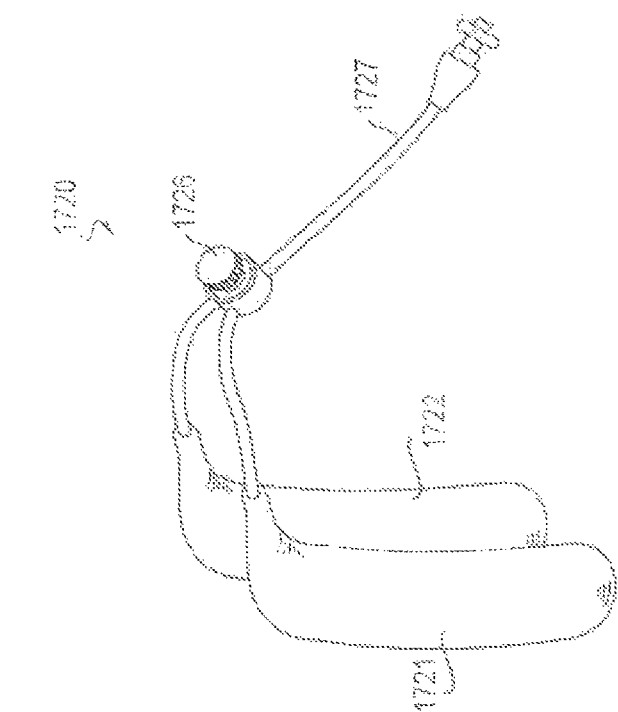
FIGS. 18A and 18B are perspective views of two, alternative embodiments of an applicator device, each including flow-altering capability.
Figure 18A:
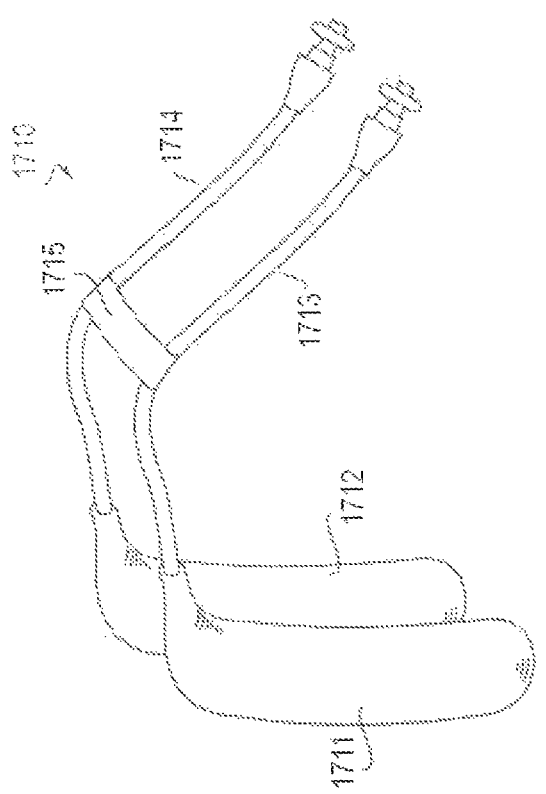

FIG. 18A depicts an alternative embodiment of an applicator device (1710), similar to that depicted in FIGS. 2A and 2B, in which each of two applicators (1711, 1712) has a dedicated conduit (1713, 1714, respectively), through which a substance or medicine may be delivered to achieve the desired effect. The applicator device (1710) may include two or more applicators (1711, 1712) and associated dedicated conduits. One advantage of this embodiment of the applicator device (1710) is that the two separate applicators (1711, 1712) with separate conduits (1713, 1714) help ensure equal delivery of substance or medicine to each applicator (1711, 1712), irrespective of the applicators' position in space and/or provide specific quantities of medicines or substances to each applicator (1711, 1712). A support strut (1715) may optionally be included, connecting the two applicators (1711, 1712).

FIG. 18B depicts an alternative embodiment of an applicator device (1720), similar to that depicted in FIGS. 2A and 2B, in which each of two applicators (1721, 1722) is connected to a valve (1726), designed to equalize or alter flow to each applicator (1721, 1722) from a single delivery conduit (1727). Other types of connectors, delivery tubes, and valves could be used, in various combinations, in various alternative embodiments.

Figure 19B:
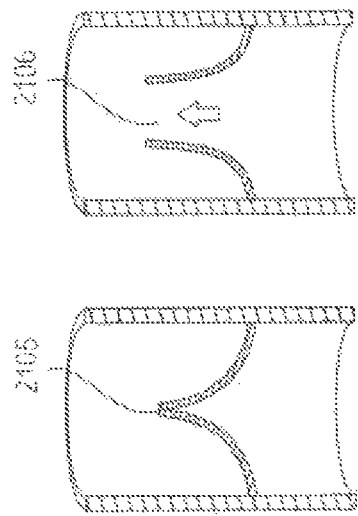
FIGS. 19A-19C are various views of an applicator system with a duck bill valve that facilitates intermittent pulsatile delivery of active substance, according to one embodiment.
Figure 19C:
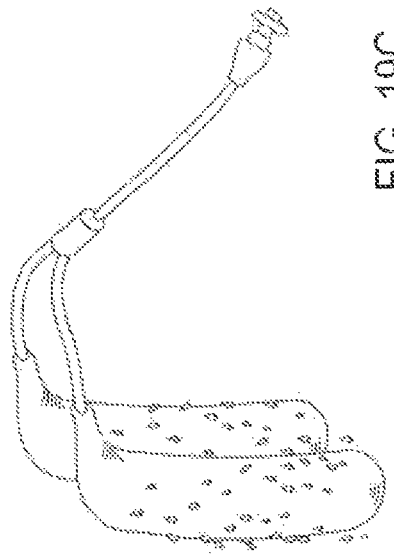
Figure 19A:
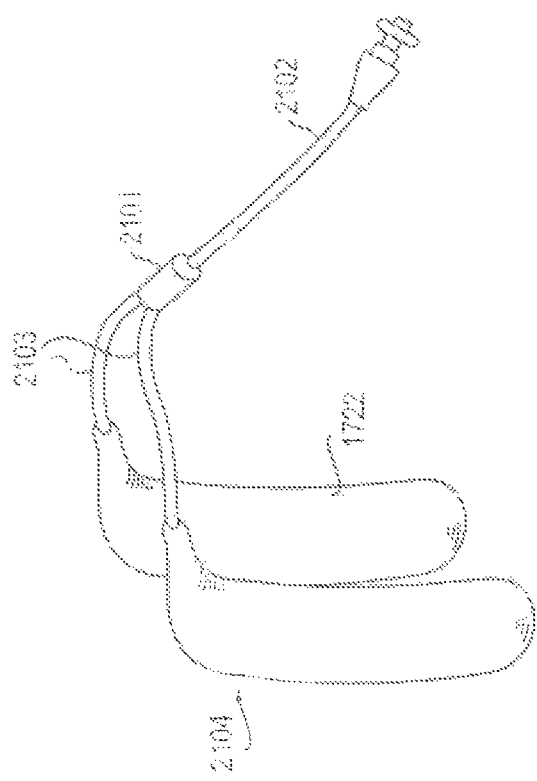

FIG. 19A depicts another alternative embodiment of an applicator system, in which a duck bill valve (2101) connects the primary conduit (2102) to the secondary conduits (2103), which then supply active substance to the applicators (2104). The primary conduit (2102) may be attached to a continuous pump source, to a syringe, or other reservoir.

FIG. 19B shows close-up views of the duck bill valve (2101) in a closed position (2105) and an open position (2106).

FIG. 19C depicts flow of active substance (2107) evenly out of the applicators (2104), which may occur in a continuous, intermittent or one-time fashion.

FIG. 20A depicts an alternative embodiment of an applicator system, in which an alternative embodiment of a valve (2111) connects the primary conduit (2112) to the secondary conduits (2113), which then supply active substance to the applicators (2114). The primary conduit (2112) may be attached to a continuous pump source, to a syringe, or other reservoir.

FIG. 20B shows close-up views of the valve (2111) in a closed position (2115) and an open position (2116).

FIG. 20B depicts flow of active substance (2117) evenly out of the applicators (21114) in a continuous, intermittent or one-time fashion.

Figure 21B:
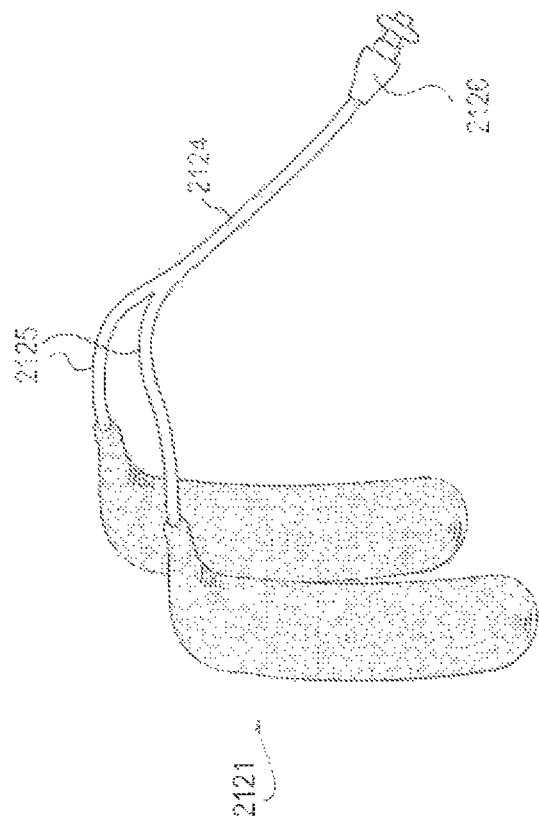
FIGS. 21A and 21B are perspective views of an applicator system whose applicators are constructed of a partially absorbent material, according to one embodiment.
Figure 21A:
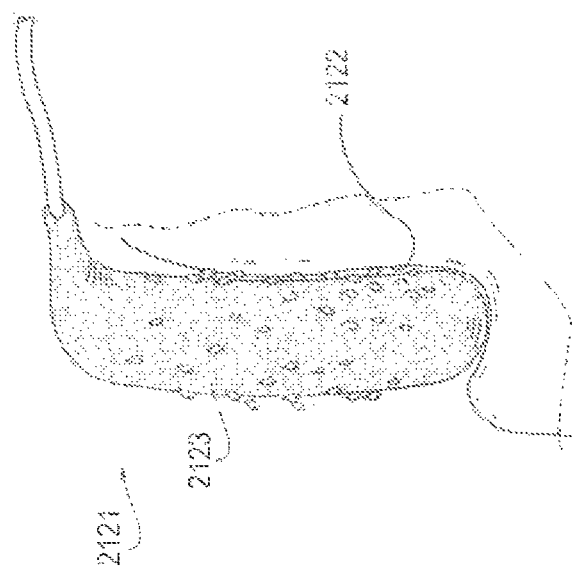

FIG. 21A depicts an exemplary applicator (2121) resting in situ in direct contact with the desired tissue (2122). The applicator is made of a partially absorbent material (2123) to provide sufficient resonance time of the active substance with the mucosal surface of the airway or other surface to achieve the desired effect.

FIG. 21B depicts the exemplary system with Its primary conduit (2124) bifurcating into secondary conduits (2125) supplying active substance to the applicators (2121). The primary conduit may be connected to a continuous or intermittent pump, syringe, or ether reservoir for the active substance via a standard Luer connector (2126).

Figure 22A:
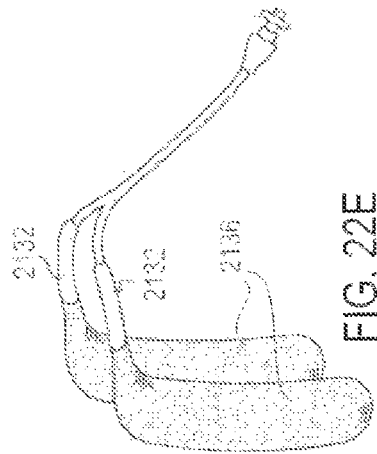
FIGS. 22A-22F are various perspective and intraoral views of an applicator system with replaceable applicators, according to one embodiment.
Figure 22B:
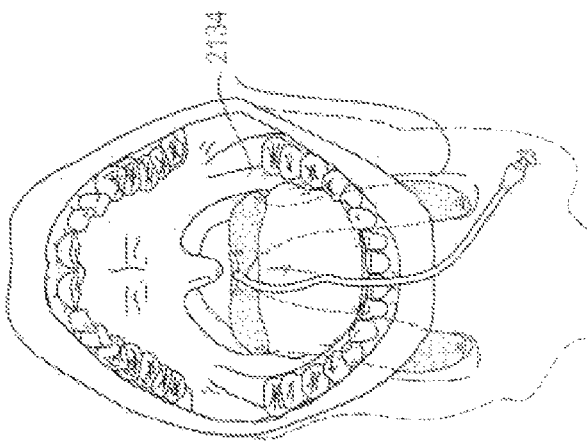

FIGS. 22A and 22B depict an exemplary system in which a primary conduit (2131) connects to secondary conduits (2132). The applicators (2133) are fixed in a detachable way to the secondary conduits, for example by clips, Velcro, buttons, or pre-formed shapes of the applicator (2133) and secondary conduit (2132) facilitating snap-on attachment. The system may rest in situ in the upper airway, with the applicators in direct contact with the mucosal surfaces of the tonsillar pillars and piriform sinuses (2134). The applicators (2133) may have been impregnated with an active substance, or receive such a substance via the conduits (2131, 2132).

Figure 22C:
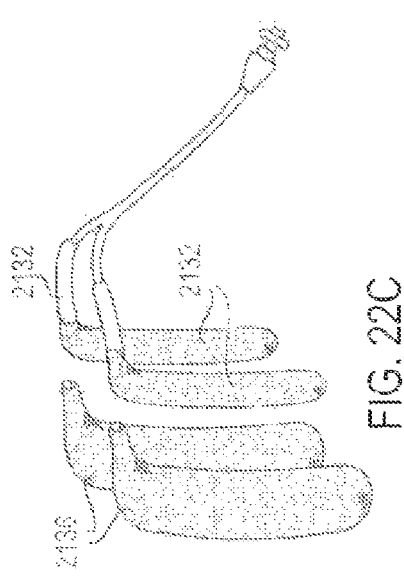
Figure 22D:
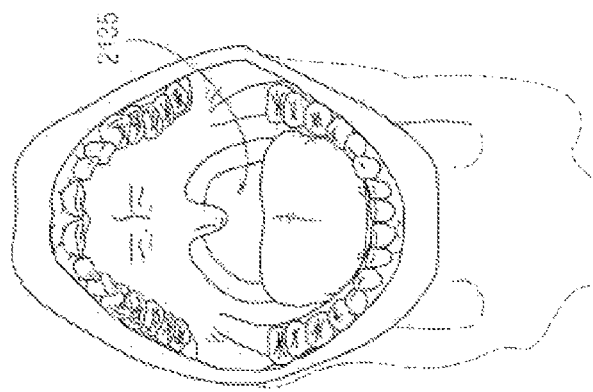

FIGS. 22C and 22D depict the exemplary system of FIGS. 22A and 22B, in which the system is removed from the upper airway (2135) so that new applicators (2136) may be attached to the secondary conduits (2132).

Figure 22E:
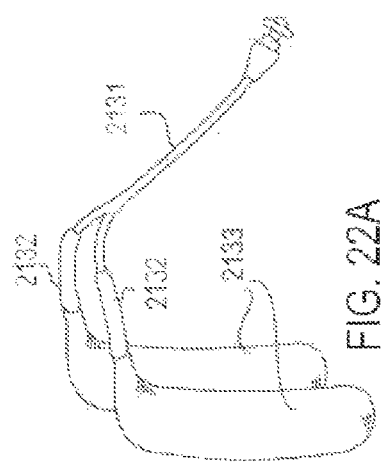
Figure 22F:
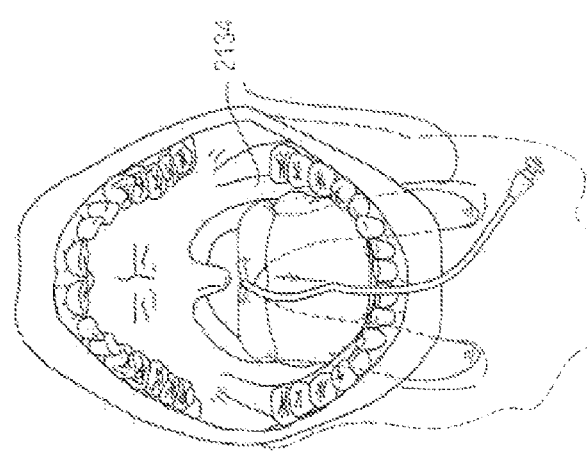

FIGS. 22E and 22F depict the exemplary system of FIGS. 22A-22D, in which the new applicators (2136) have been attached to the secondary conduits (2132), which in turn rest in situ, with applicators (2136) in direct contact with the mucosal surfaces of the tonsillar pillars and piriform sinuses (2134).

Figure 23:
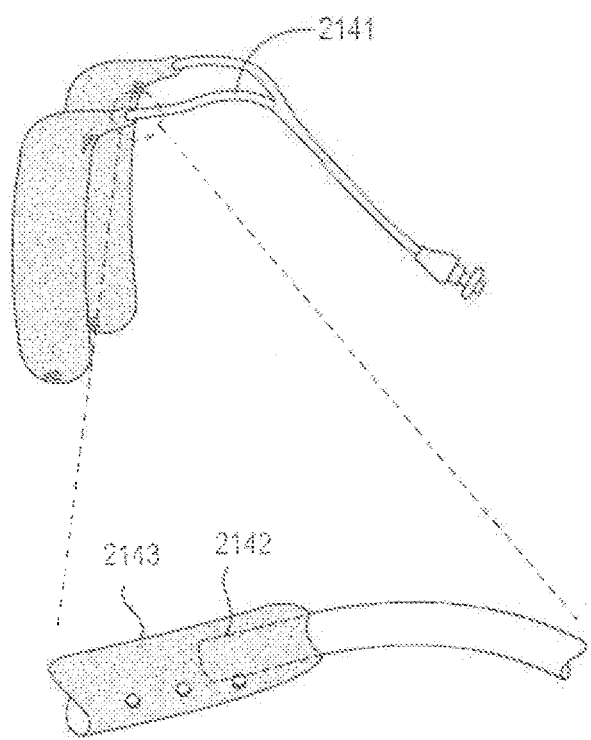
FIG. 23 is a perspective view of an applicator system, according to another embodiment.

FIG. 23 shows an exemplary secondary conduit (2141) whose terminus (2142) connects to the applicator (2143). The applicator (2143) may be of a different durometer material from the secondary conduit (2141), and may be or a compressible material so that the effective length in the long dimension varies to fit different anatomic dimensions among individuals. The applicator has a plurality of holes, for instance laser-drilled holes (2144) so that active substance may be delivered to the desired areas of the upper airway anatomy.

Figure 24:
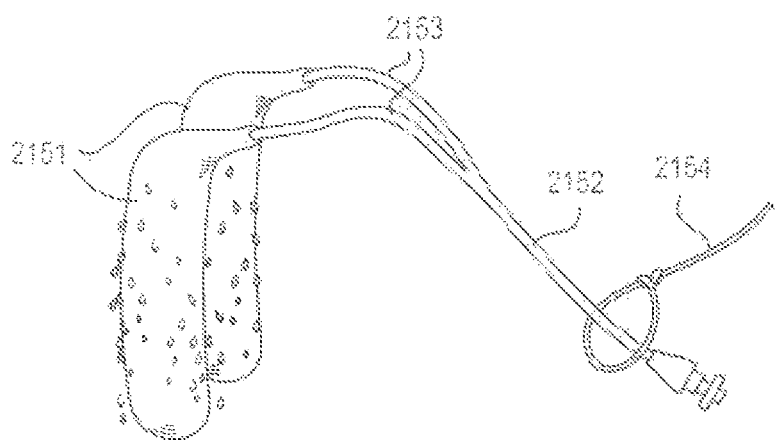
FIG. 24 is a perspective view of an applicator system, in which active substance is impregnated into the applicators, according to another embodiment.

FIG. 24 shows an alternate exemplary system in which the applicators (2151) are impregnated with active substance which elates in a controlled fashion with time, such as impregnated silicone or other polymeric material. In this instance the primary (2152) and secondary (2153) conduits may be hollow or solid, and do not deliver active substance to the applicators. A loop (2154) at the terminus of the primary conduit (2152) facilitates easy retrieval of the system from the upper airway.

Figure 25A:
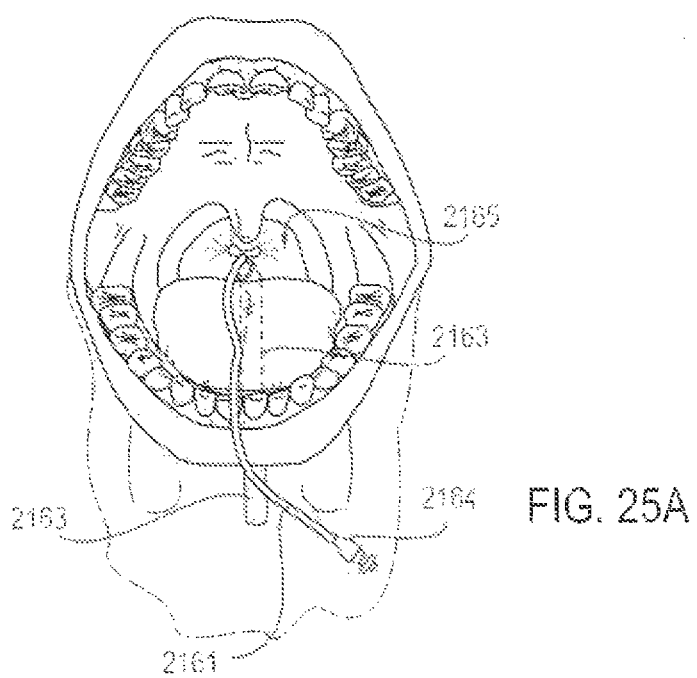
FIGS. 25A and 25B are views of an applicator system, illustrated inside and outside a mouth, respectively, according to another alternative embodiment.
Figure 25B:
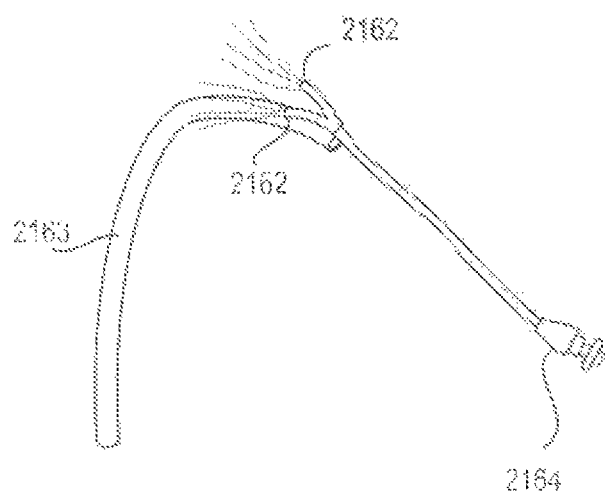

FIGS. 25A and 25B show an alternate exemplary system in which a single conduit (2161) terminates with two spray applicators (2162) for delivery of active substance. The applicators are connected to an L-shaped piece (2163) that facilitates placement of the applicators at the desired anatomic position in the upper airway (2165). The system may be attached to a pump, for example a peristaltic or syringe pump, or other reservoir containing active substance via a standard Luer (2164) or other connection.

Figure 26B:
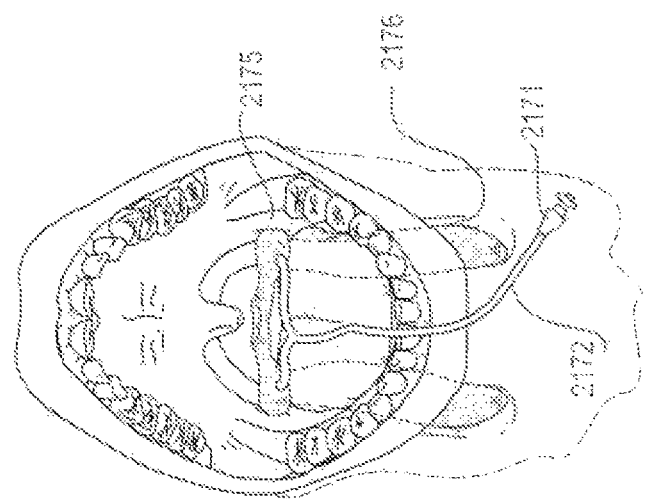
FIGS. 26A and 26B are perspective and intraoral views, respectively, of an applicator system designed to fit the anatomic contours of the upper airway, according to one embodiment.
Figure 26A:
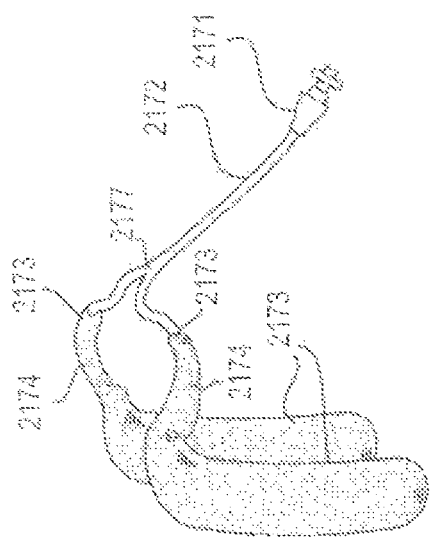

FIG. 26A shows an exemplary system consisting of a Luer connector (2171) attached to the terminus of the primary conduit (2172) bifurcating into secondary conduits (2173). The bifurcation (2177) splays to provide an outward force that facilitates direct contact with the airway mucosa while accounting for anatomic variation in width of the upper airway between individuals. A curve (2174) in the applicator (2173) facilitates direct contact with the anatomic contour of the tonsillar pillars.

FIG. 26B shows the exemplary system in situ in the upper airway, with the curve of the applicator adjacent to the tonsillar pillar (2175), while the terminus of the applicator rests in the piriform sinus (2176).

Figure 27B:
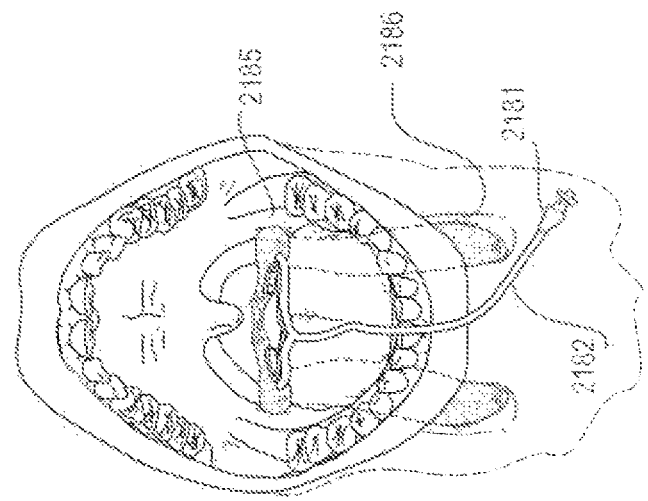
FIGS. 27A and 27B are perspective and intraoral views, respectively, of an applicator system designed to fit the anatomic contours of the upper airway, according to one embodiment.
Figure 27A:
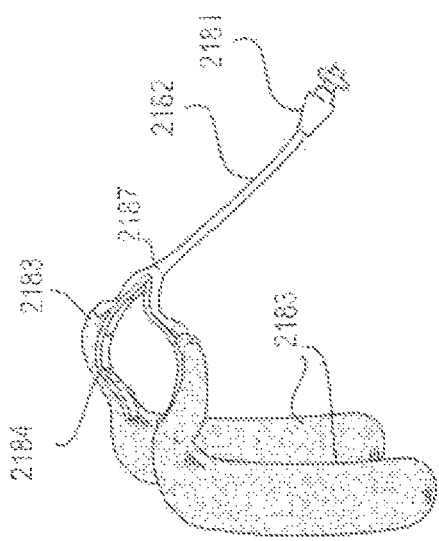

FIG. 27A shows an exemplary system consisting of a Luer connector (2181) attached to the terminus of the primary conduit (2182) bifurcating into secondary conduits (2183). The bifurcation (2187) splays to provide an outward force that facilitates direct contact with the airway mucosa while accounting for anatomic variation in width of the upper airway between individuals. The upper part of the applicator contains a curve with an extruding clip structure (2184) to ensure maximum contact with the tonsillar pillars.

FIG. 27B shows the exemplary system in situ in the upper airway, with the curve of the applicator adjacent to the tonsillar pillar (2185), while the terminus of the applicator rests in the piriform sinus (2186).

Figure 28B:
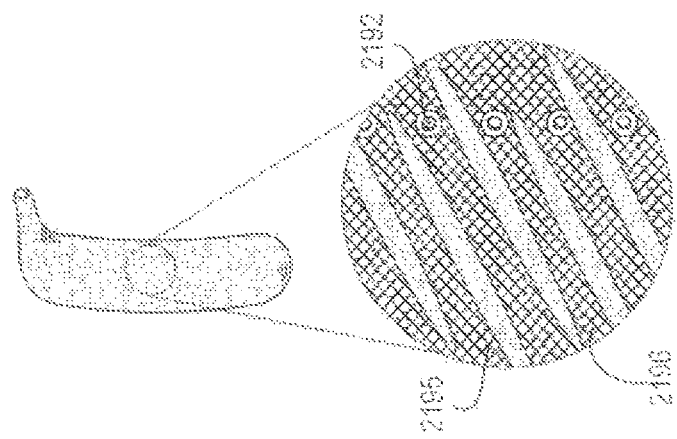
FIGS. 28A and 28B are perspective views of two different embodiments of applicators, illustrating alternative surface contour and material properties, according to various alternative embodiments.
Figure 28A:
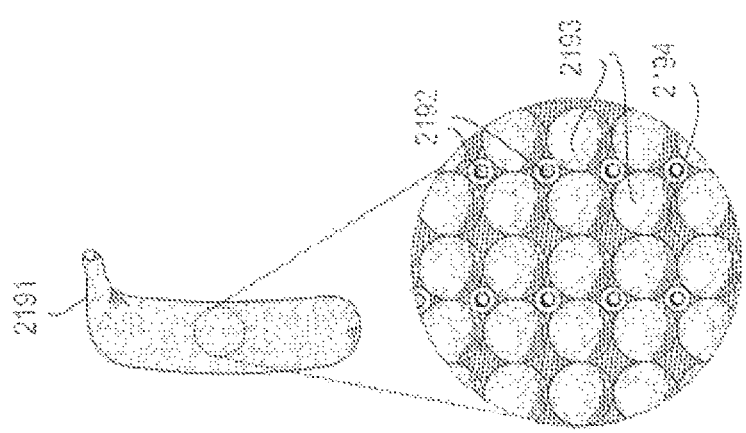

FIGS. 28A-28C show exemplary surface textures, contours and structures of an applicator (2191). Such applicators (2191) may be used to deliver local anesthetic to the upper airway in a continuous, intermittent or one-time fashion.

FIG. 28A shows an applicator with a plurality of holes (2192) through which active substance may be delivered. The surface is contoured with bumps or dimples (2193), with intervening ridges (2194). Such surface may be partially or entirely coated with hydrophilic or hydrophobic materials, or intrinsically hydrophilic or hydrophobic. Hydrophobic portions may be used to prevent abrasive injury to the mucosal tissue; hydrophilic surfaces may be used to draw active substance along the ridges via capillary or surface tension forces.

FIG. 28B shows an applicator with linear ridge structures (2195) and a plurality of holes (2192) to deliver active substance to the applicator. The ridge structure serves to draw active substance along the entire surface area of the applicator. In this embodiment, the ridge structures (2195) are hydrophobic in nature, whereas the remainder of the surface is hydrophilic (2190).

In either of the embodiments illustrated in FIGS. 28A and 28B, the entire surface of an applicator may be made hydrophilic or hydrophobic.

Figure 29B:
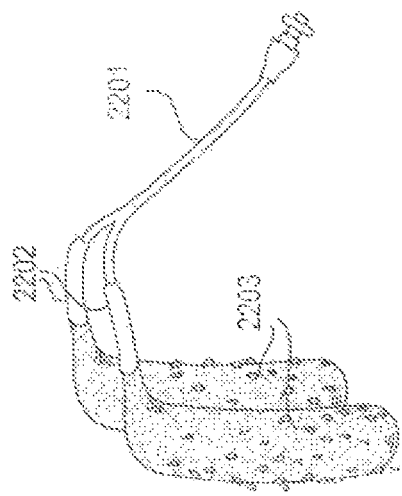
FIGS. 29A and 29B are perspective views of an applicator system in which the applicators are balloon structures, according to one embodiment.
Figure 29A:
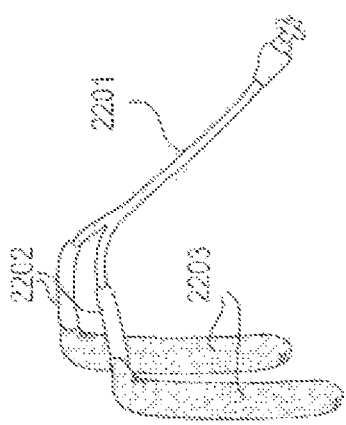

FIG. 29A shows an exemplary system in winch a rigid primary conduit (2201) connects to two secondary conduits (2202) which in turn are connected to applicators (2203). Both the secondary conduits (2202) and applicators (2203) are inflatable balloons, and the applicators are perforated such that they can weep active substance. Such structures are inflated with active substance, air or a combination thereof.

FIG. 29B shows the exemplary system in its inflated configuration. Inflation is performed once the system has been placed in the upper airway in order to ensure maximal apposition with the relevant mucosal tissue.

Figure 30D:
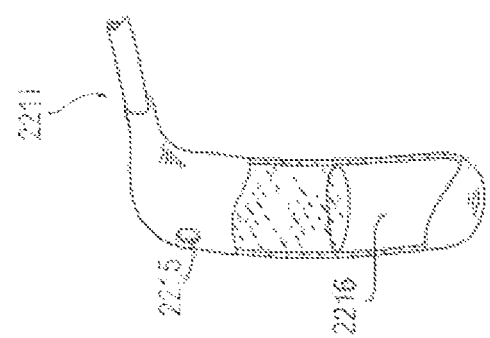
FIGS. 30A-30D are perspective views of four embodiments of applicators with one or more holes, according to various alternative embodiments.
Figure 30C:
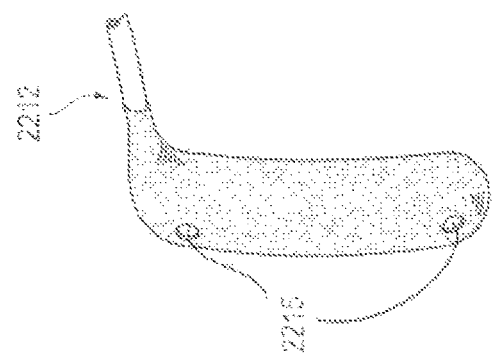
Figure 30B:
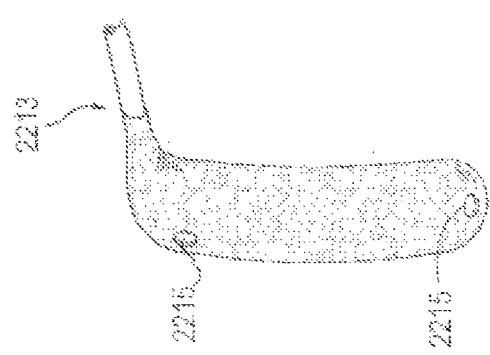
Figure 30A:
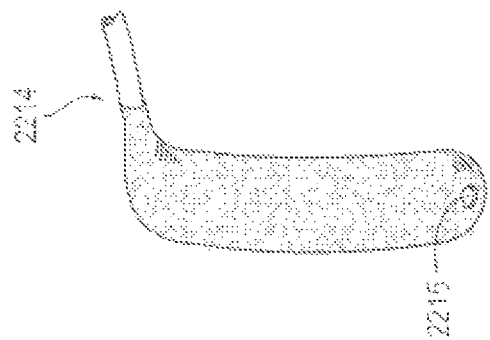

FIG. 30A shows an exemplary applicator and/or secondary conduit (2211) having a single hole (2215) just below the major curve. An air pocket (2216) is formed when the applicator is filled with active substance from above, which serves to equalize pressure and/or flow between interconnected applicators.

FIG. 30B shows an alternate exemplary applicator and/or secondary conduit (2212) in which two holes are made (2215) at points that facilitate delivery of active substance to the region of the tonsillar pillars and piriform sinuses, the lower hole being made on the lateral aspect of the applicator.

FIG. 30C shows an alternate exemplary applicator and/or secondary conduit (2213) in which two holes are made (2213) at points that facilitate delivery of active substance to the region of the tonsillar pillars and piriform sinuses, the lower hole being made on the inferior aspect of the applicator. The sizing office holes can be tailored to achieve the desired flow rate through the applicator.

FIG. 30D shows an alternate exemplary applicator and/or secondary conduit (2214) in which a single hole (2215) is present inferiorly, which delivers active substance to the desired part of the upper airway. The diameter of the hole can be tailored to achieve the desired flow rate by controlling back pressure in the applicator, when the active substance is applied.

FIG. 31 shows an alternate exemplary system (2220) with applicators (2223 and 2224). This system comprises a connector (2226) to attach a drug delivery conduit (2225) to a flow channel that is delivering pharmaceutical compounds from a delivery system like a syringe and/or infusion pump. This drug delivery conduit (2225) bifurcates into a left and right drug delivery conduit (2221) that curves around to fit a contour of the back of the throat to yield a vertical or near vertical segment (2222) that is at least partially adjacent to the tonsillar pillars. After the bifurcation the drug delivery conduits (2221) have at least two pores on them that allow for weeping or dripping of pharmaceutical solution into applicators (2223) that are at the top of the vertical segment (2222) such that those applicators (2223) would contact the mucosal surface at or near the top of the tonsillar pillar. Similarly, at the base of the vertical segment of the drug delivery conduit (2222) there are at least two pores or holes that allow for weeping or dripping of pharmaceutical solution into two applicators (2224) at the base, which allow for contact against the mucosa and/or dripping onto the mucosa to the piriform sinus area and/or the adjacent or surrounding tissues.

Figure 32B:
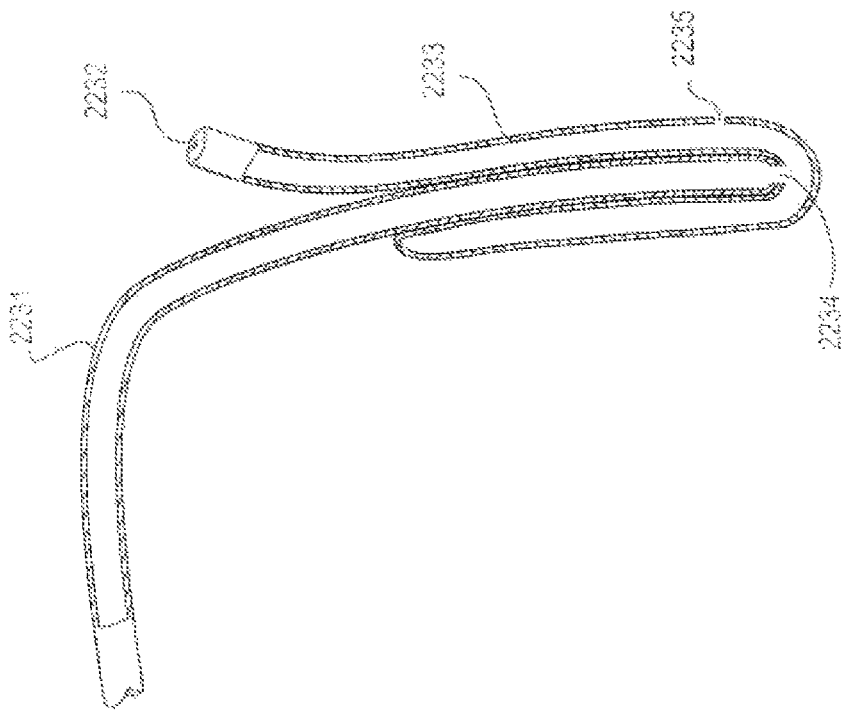
FIGS. 32A and 32B are perspective views of two embodiments of applicators that are directional and curved against gravity with single or multi exit holes, according to various alternative embodiments.
Figure 32A:
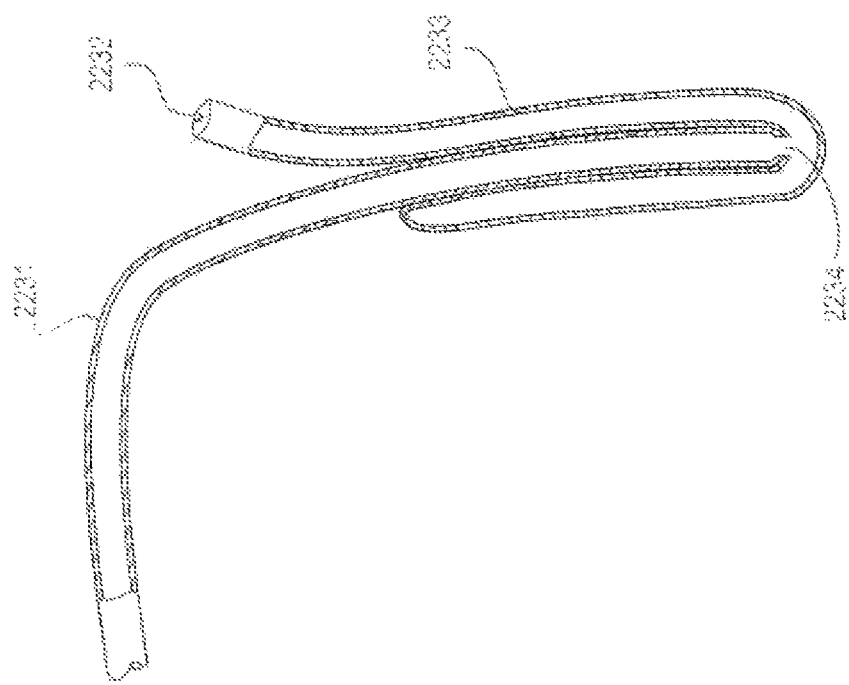

FIG. 32A shows an alternative exemplary applicator setup where a drug delivery tube (2231) is curved and is in fluid communication with another curved segment (2233), and where a hole is located at the base (2234). This connection allows for a reservoir to form in the drug delivery segments until it reaches a high enough level to spray, drip, or be pushed out of a higher port or hole (2232).

FIG. 32B shows an alternative exemplary applicator setup where a drug delivery tube (2231) is curved and/or connected to another curved segment (2233) by a hole at the base of the main tube (2234) or by direct curve without connecting through separate tubing. There is also a hole at the base (2235) which may be smaller than a higher hole (2232) in order to modulate the flows to be somewhat uniform with a height difference. The ascending conduit (2233) reaches the higher hole (2232) to allow for drug to flow out of this hole.

Figure 33C:
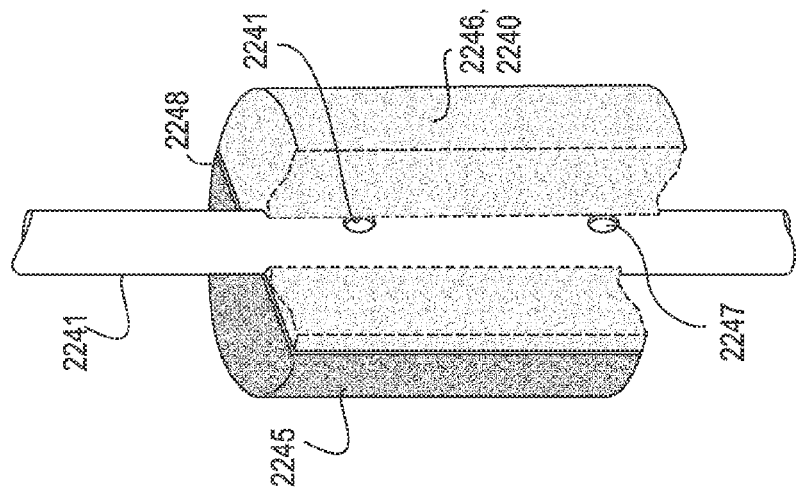
FIGS. 33A-33C are various views of alternative embodiments of applicators with separated application segments, according to various alternative embodiments.
Figure 33B:
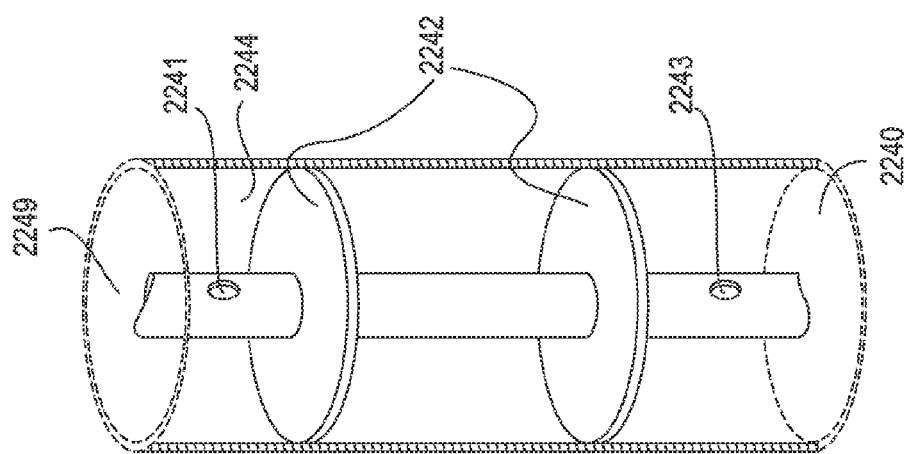
Figure 33A:
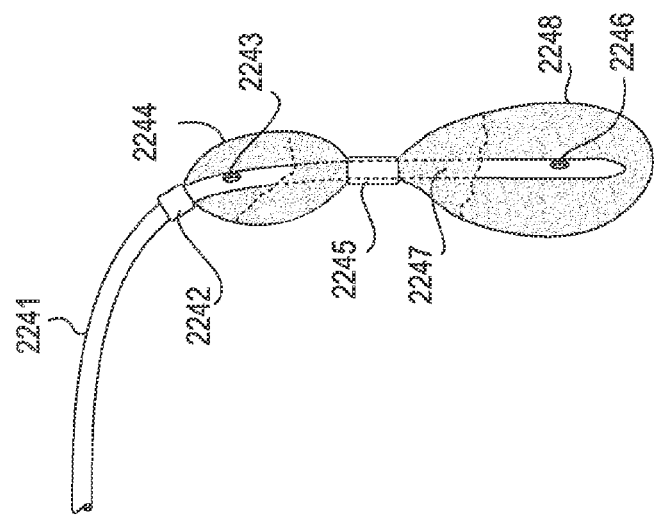

FIG. 33A shows an alternative exemplary applicator setup where a sponge with upper (2244) and lower (2248) segments are divided by a separator (2245). The sponge is held on the drug delivery conduit (2241) by a connection (2242) that may be glue, thermo sealing, or shrink wrapping. At least one upper hole (2243) and one lower hole (2246) are used to supply pharmaceutical solution to the upper (2244) and lower (2248) applicator sponge segments. The vertical segment of the drug conduit tube (2247) may have multiple exit ports at different sides. Additionally the sponge segments (2244 and 2248) may weakly hold material as a sponge reservoir until application to a tissue or area by contact or dripping from saturation are achieved.

FIG. 33B shows an alternative exemplary applicator with a drug delivery conduit (2249) with upper (2241) and lower (2243) hole segments to deliver pharmaceutical solution to upper (2244) and lower (2240) drug reservoir material. This drug reservoir applicator material may be sponge or similar resonance material but it is separated by liquid blocking seals (2242) to help flow and resonance be more equal in the top and bottom of the applicator.

FIG. 33C shows an alternative exemplary applicator cross sectional view with a drug delivery conduit (2241) that has a drug outlet pore or hole (2249 and 2247). This outlet pore or hole (2249 and 2247) may represent one or more outlets from the drug delivery conduit (2241) and it serves as a means to deliver a pharmaceutical solution to the application portion of the applicator. The application portion (2246 and 2240) is on only a partial segment of the circumference of the drug delivery tube. This is to ensure that less reservoir is needed since application to the mucosa is only done on one side of the tube. This can be accomplished by sealing half of the surface with a surface sealing material (2245) that is at least partially impermeable to the pharmaceutical solution. This sealed surface could also be separated laterally by a lateral sealing component (2248) to at least partially prevent material from flowing into the sealed off segment and/or connect a non-reservoir segment to the half that is the reservoir (2246). Alternatively, this can be accomplished by only have a wedge or partial segment (2240) applicator portion instead of a fully circumferential applicator.

Figure 34C:
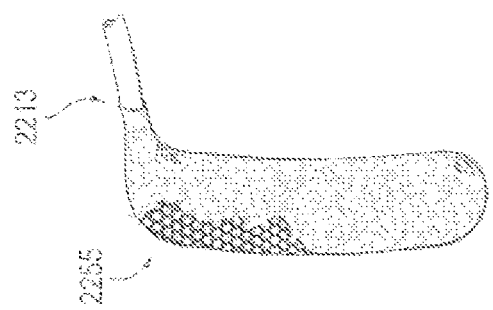
FIGS. 34A-34C are perspective views of the embodiments of applicators that are multi-layered, according to various alternative embodiments.
Figure 34B:
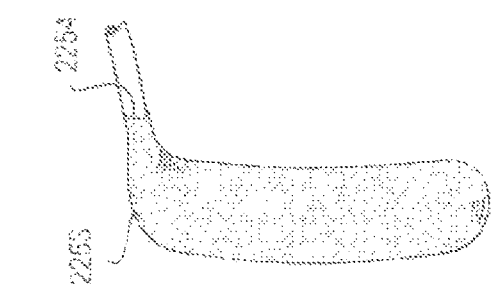
Figure 34A:
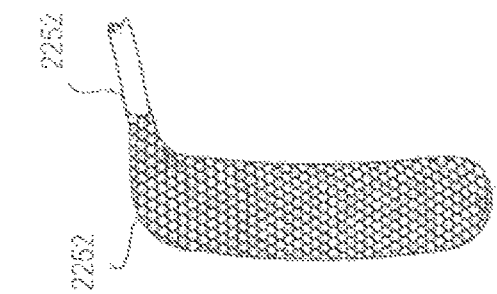

FIGS. 34A-34C show another exemplary applicator configuration where the system is a multi-layered applicator. The applicator is comprised of at least two layers. One layer has large open cell sponge like characteristics (2251) that enables it to receive pharmaceutical fluid from an inlet port (2252) and store a lot of that material. In order to control the diffusion of that fluid to the surrounding tissue an outer small opening membrane author sponge like covering (2253) is connected to and covering over the large pore inner layer (2251). This outer covering also has an opening for drug flow into the applicator (2254). Combining them together forms a multi layered applicator system (2255) with variable storage resonance and/or diffusion characteristics depending on what materials are used and their respective pore sizes.

Figure 35:
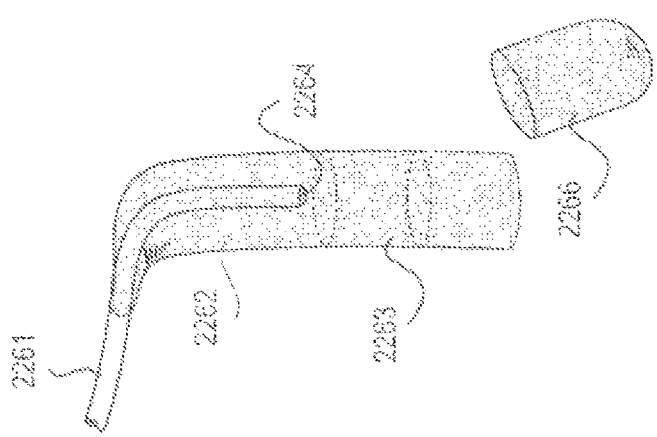
FIG. 35 is a perspective view of an applicator that includes break-away portion(s) and is adjustable to variable anatomical positioning, according to one alternative embodiment.

FIGS. 35A-35C show another exemplary applicator with a drug delivery conduit (2261). This drug delivery conduit empties via one or more ports (2264 and 2265) into a reservoir material like a sponge (2262). This reservoir material also serves to deliver drug through dripping and/or direct apposition to tissue. In order to adjust for a one size fits all length the reservoir material (2262) has several segments (2263) that can be broken or torn off easily (2266) in order to adjust the height for specific patients easily. Additionally, FIG. 35A shows that the drug delivery conduit (2261) could be configured to only extend partially down the segment of the applicator (2262 and 2263). In the event that the removable segment (2263) are not removable but instead part of the top applicator sponge reservoir (2262) then the lower part of the sponge reservoir (2263) would be squishy such that it would retract, depress, or spring against the tissue at the bottom of the piriform sinus as a much more malleable or pliable material than that of the harder drug delivery conduit (2261) that only extended through a portion of the applicator to allow for this springy squishiness upon contact at the base of the piriform sinus in short airways.

FIGS. 36A and 36B show another exemplary system for delivery of pharmaceutical compounds via a drug delivery conduit (2272). The conduit has a connector (2271) that connects it to a drug reservoir and corresponding delivery device such as a manual syringe, infusion pump, and/or syringe pump. The drug delivery conduit (2272) has one initial bifurcation (2273) and then at least one more additional minor bifurcation (2274). These bifurcations (2273 and 2274) create two or more applicator segments that are directly focused through minor drug delivery conduits to key anatomical areas. These minor drug delivery conduits after the bifurcations could be composed of multi or single layers and/or composed of spongy high resonance materials (2275). They could also be made of simple delivery conduit material such as PEEK or PEBAX and end in single or multiple delivery ports (2276).

Figure 37:
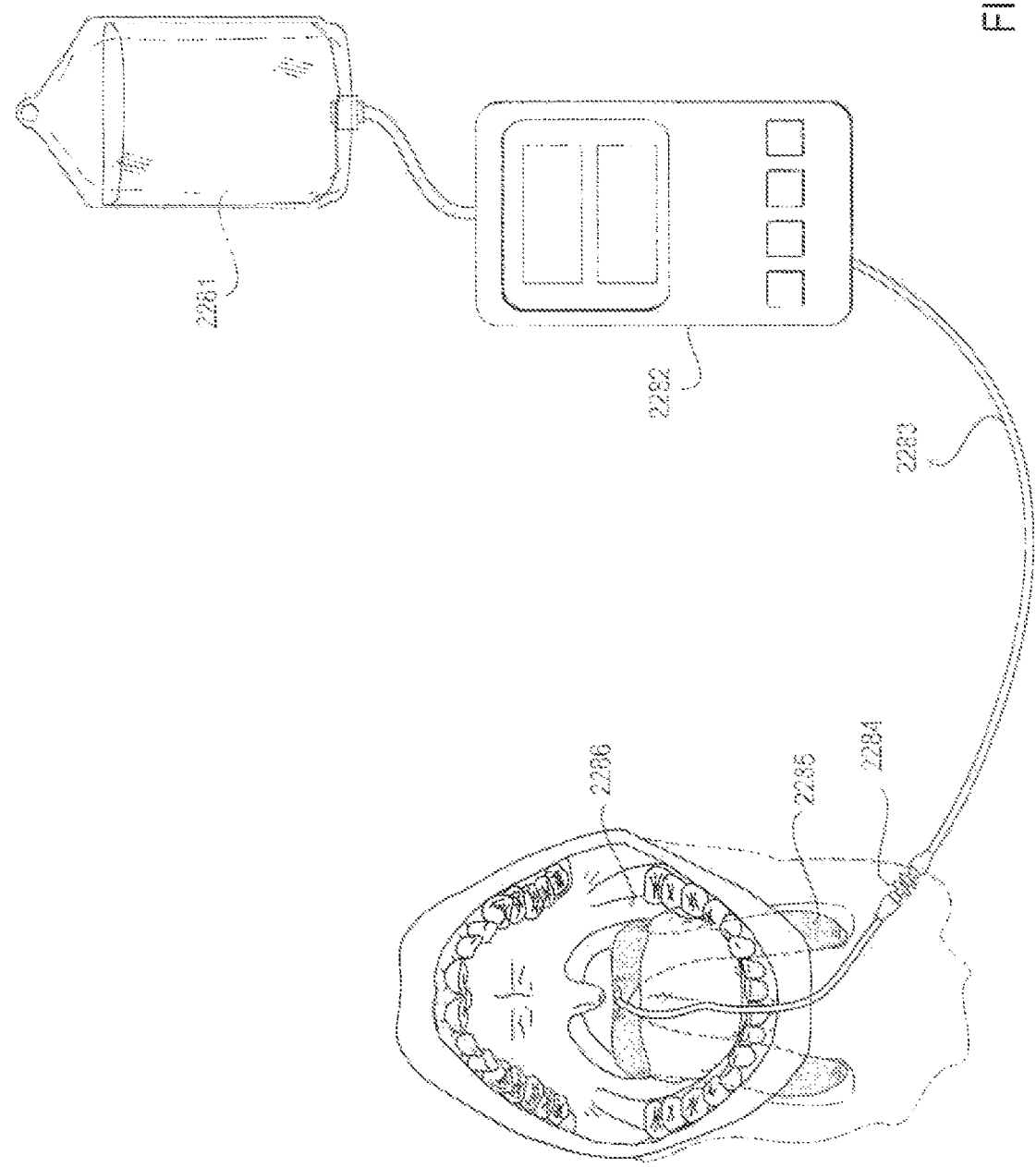
FIG. 37 is a perspective view of an applicator system with an infusion drug pump with IV bag reservoir, according to one embodiment.

FIG. 37 shows another exemplary system for delivery of pharmaceutical compounds that comprises applicators of a pharmaceutical compound (2285) that are in place behind the tonsillar pillars (2286) and/or hooked around them while descending around the contour of the throat into the piriform sinus. The drug delivery conduit is connected (2284) to a second drug delivery conduit (2283) that is fed by an infusion pump (2282) pumping fluid from an infusion bag (2281).

Figure 38:
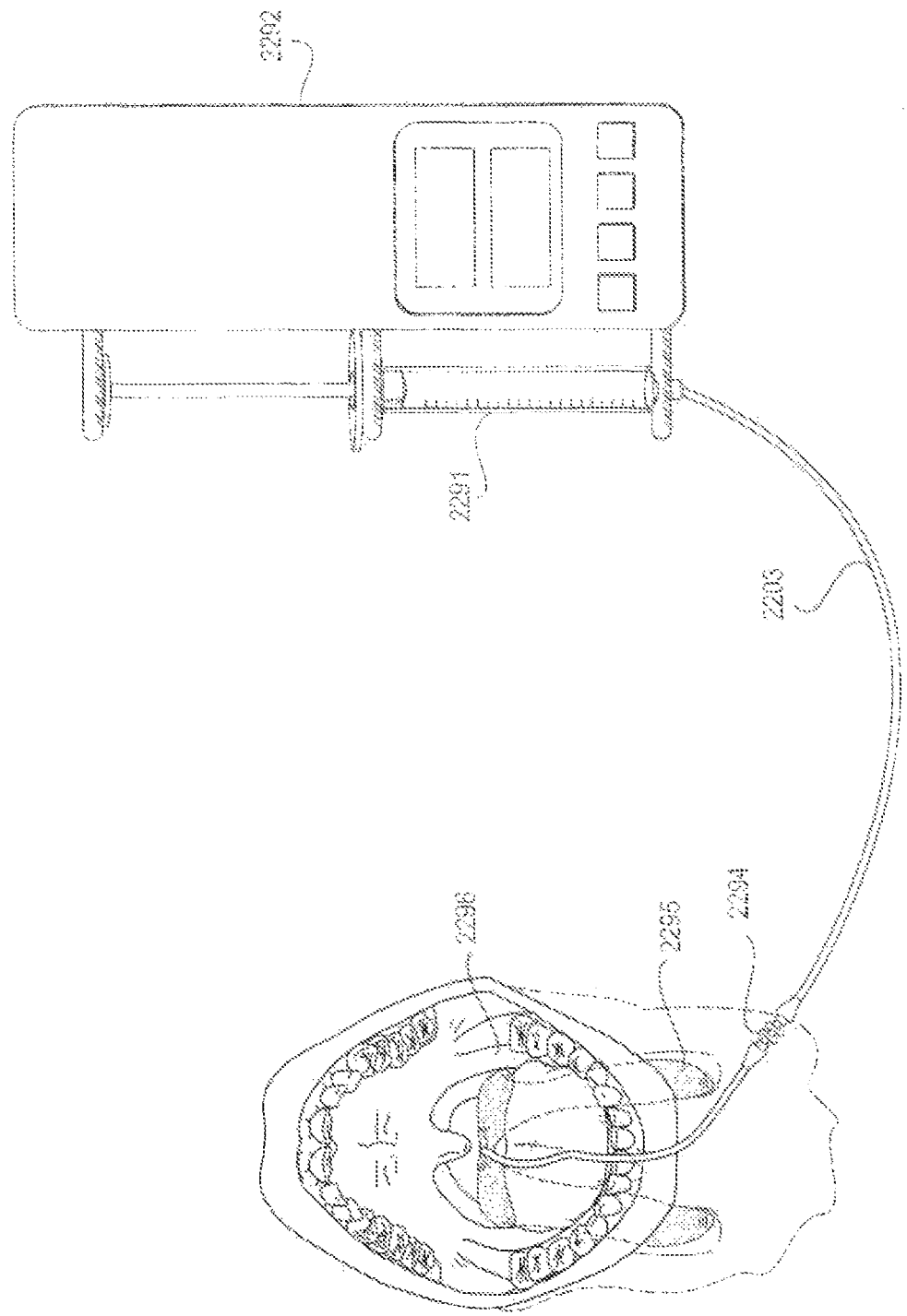
FIG. 38 is a perspective view of an applicator system with a syringe drug pump with syringe reservoir, according to an alternative embodiment.

FIG. 38 shows another exemplary system for delivery of pharmaceutical compounds that comprises applicators of a pharmaceutical compound (2205) that are in place behind the tonsillar pillars (2296) and/or hooked around them while descending around the contour of the throat into the piriform sinus. The drug delivery conduit is connected (2294) to a second drug delivery conduit (2293) that is fed by a syringe pump (2292) pumping fluid from a loaded syringe (2291).

Figure 39:
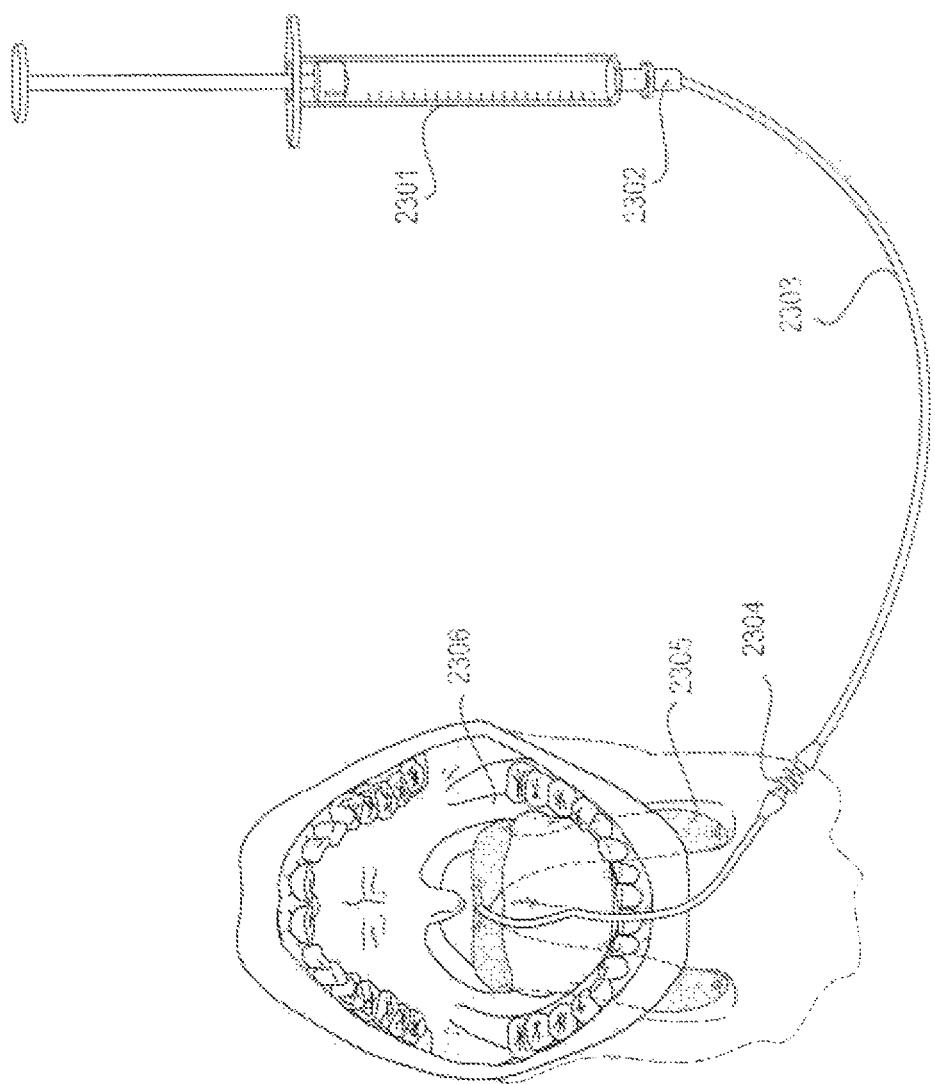
FIG. 39 is a perspective view of an applicator system with a manual syringe for delivery and reservoir, according to an alternative embodiment.

FIG. 39 shows another exemplary system for delivery of pharmaceutical compounds that comprises applicators of a pharmaceutical compound (2305) that are in place behind the tonsillar pillars (2306) and/or hooked around them while descending around the contour of the throat into the piriform sinus. The drug delivery conduit is connected (2304) to a second drug delivery conduit (2303) that is fed by a manually activated syringe (2301) pumping fluid from itself via a connector (2302) to the drug delivery conduit (2303).

Figure 40:
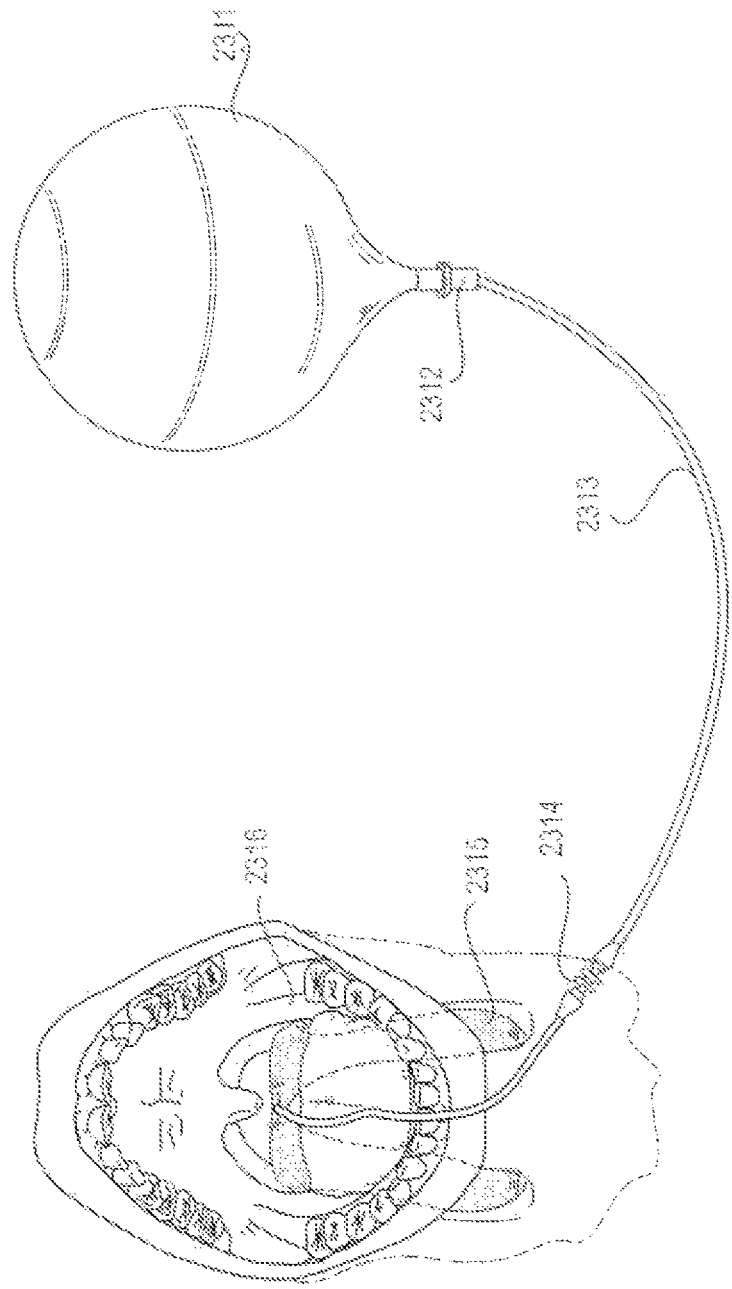
FIG. 40 is a perspective view of an applicator system with a balloon drug pump with reservoir, according to another alternative embodiment.

FIG. 40 shows another exemplary system, for delivery of pharmaceutical compounds that comprises applicators of a pharmaceutical compound (2315) that are in place behind the tonsillar pillars (2316) and/or hooked around them while descending around the contour of the throat into the piriform sinus. The drug delivery conduit is connected (2314) to a second drug delivery conduit (2313) that is fed by a balloon pump (2311) pumping fluid from itself via a connector (2312) to the drug delivery conduit (2313).

FIG. 41 shows another exemplary applicator for delivery of pharmaceutical compounds with a spiraled flow channel (2325). This spiraled flow channel (2325) allows for flow and retention of fluid exiting from the delivery conduit (2331) by openings in it (2336 and 2334). This spiraled guiding effect could be due to a groove cut in the side of the tub and/or a groove created by adding a spiraled strip to the outside of the tube. This groove could work to retain fluid and/or distribute it by capillary action and/or areas of hydrophobic and/or hydrophilic coating. The grooves don't necessarily need to be spiraled but could be zig-zag, notched, right angled or curved, or any variety or combination of other grooves or shapes which encompass the same mechanism of action to retain and deliver liquid material to adjacent mucosal surface. The thickness could also be variable, and the pore could allow material to spiral from a central pore through a spiral or other geometric mesh network to an outlet or exit for application.

FIG. 42 shows an exemplary system for delivering a pharmaceutical liquid to a mucosal surface by applicators (2331). The drug delivery conduit (2335) supplying those applicators (2331) is connected to a drug reservoir and/or pumping means by a connector (2336). The drug delivery conduit bifurcates (2334) into two drug delivery conduits (2332) which could be smaller than the main drug delivery conduit in diameter and/or relatively uniform in shape, diameter, and size to each other. The secondary drug delivery conduits (2332) are springy such that they splay outward to contact the mucosal surface of the upper airway near the perform sinus and tonsillar pillars. To adjust the springiness and diameter to help optimize contact of the pharmaceutical applicators (2331) with the mucosal wall, a sliding adjustment tool (2333) that squeezes and/or clamps onto the tube is used. This tool (2333) can be easily adjusted by compression to release a spring which is holding the sliding tool (2333) in place and adjusting the distance between the two applicators (2331) depending on its position along the drug conduits (2332).

FIGS. 43A and 43B are perspective views of the system of FIG. 42, illustrating the sliding adjustment tool (2333) in a forward position (FIG. 43A) and a retracted position (FIG. 43B) As described above, the secondary drug delivery conduits (2332) are springy, such that they splay outward to contact the mucosal surface of the upper airway near the perform sinus and tonsillar pillars. To adjust the springiness and diameter of the device and thus help optimize contact of the pharmaceutical applicators (2331) with the mucosal wall, the sliding adjustment tool (2333) can slide back to help spread the applicator conduits (2332) outward and forward to help bring the conduits (2332) closer together Sliding the sliding adjustment tool (2333) forward may also serve to retract the curvature of the applicators (2331), as demonstrated in 43A.

Figure 44:
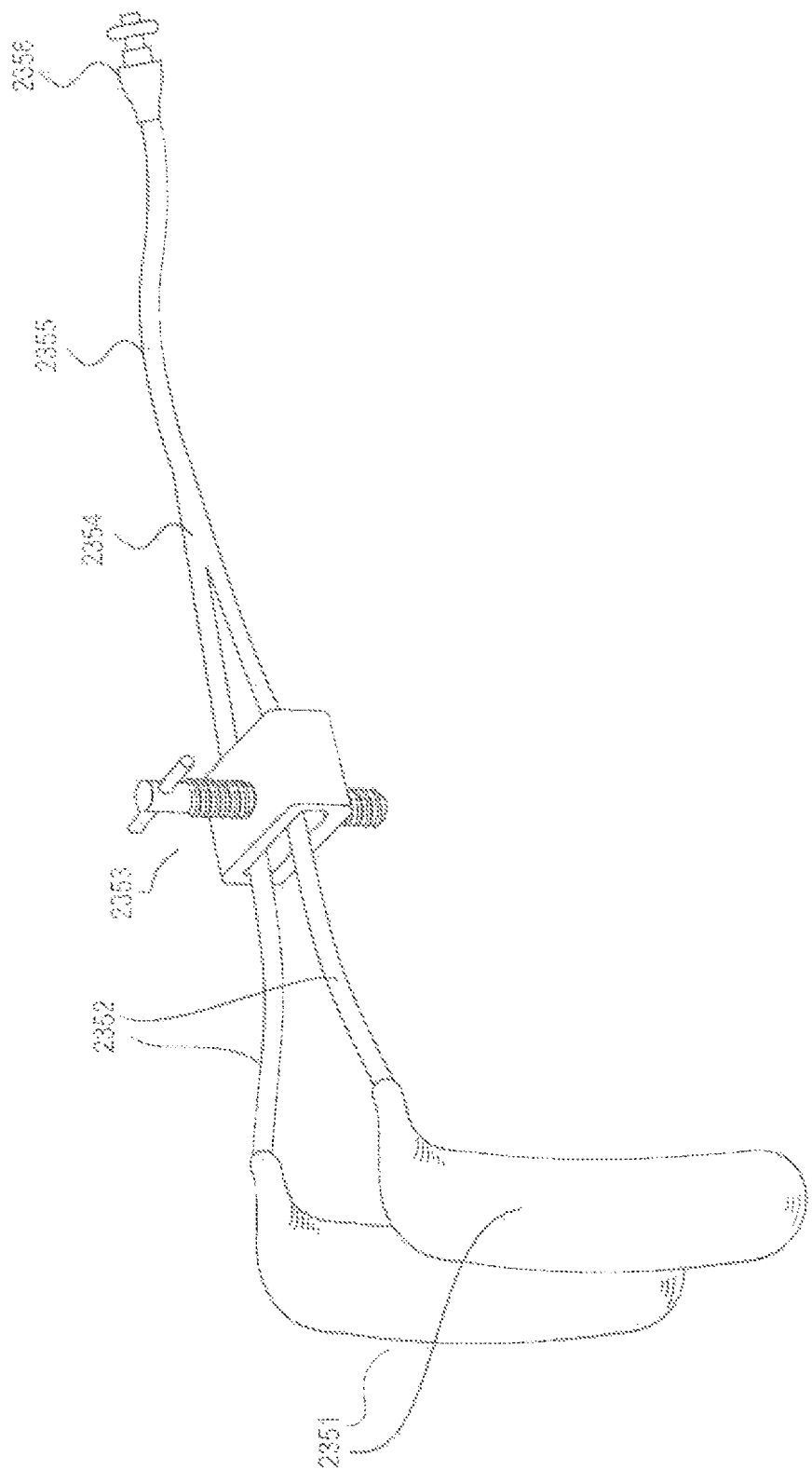
FIG. 44 is a perspective view of an applicator system with an adjustable feature that adjusts wider and narrower as adjusted by screw thread system, according to one embodiment.

FIG. 44 shows an exemplary system for delivery of a pharmaceutical liquid to a mucosal surface by applicators (2351). A drug delivery conduit (2355) connects via a connector (2356) to a drug delivery device like a syringe pump, manual syringe, infusion pump, or other device. The drug delivery conduit (2355) then bifurcates (2354) to branch into two drug delivery conduits (2352) that connect to the applicators (2351). There is a tool (2353) that is threaded that screws outward and inward to adjust the spread of the minor drug delivery conduits (2352) relative to each other. This tool (2353) has connector ports, holes, clips, or direct connections with which it communicates the physical force of threading apart or together when it's being acted upon. This mechanism allows the applicators (2351) to move farther away or closer to each other to better fit and/or hook into place in the upper airway.

Figure 45B:
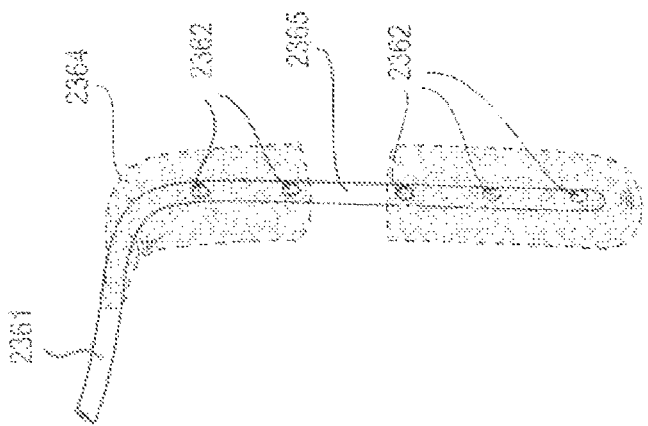
FIGS. 45A and 45B are perspective views of an applicator with a sponge applicator over a conduit with holes in it, according to one embodiment.
Figure 45A:
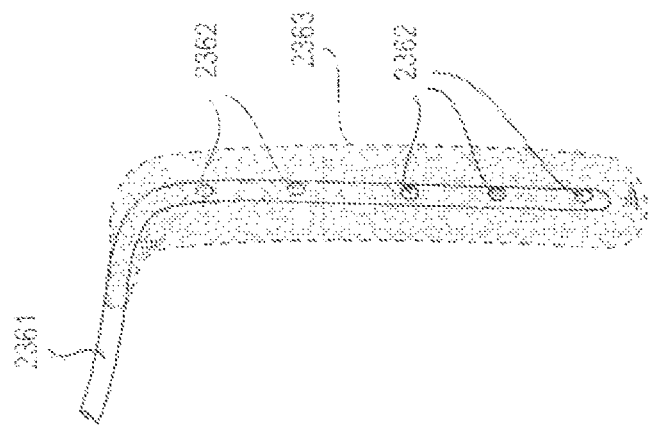

FIGS. 45A and 45B show an exemplary applicator for pharmaceutical drug components. This curved applicator has a contoured drug delivery conduit (2361) that has one or more outlet pores for flow (2362). These outlet pores (2362) can be separated into two separate sponge segments that fit over the conduit (2364 and 2366) or it can comprise one continuous sponge type segment (2363) that fits over the length of a single portion of delivery conduit (2361). The sponge applicator segments (2363, 2364, 2366) are able to hold or retain at least a small portion of fluid in a meshwork such that it leaches out to the contact surface area of tissue anchor chops when the system is at least partially saturated.

Figure 46:
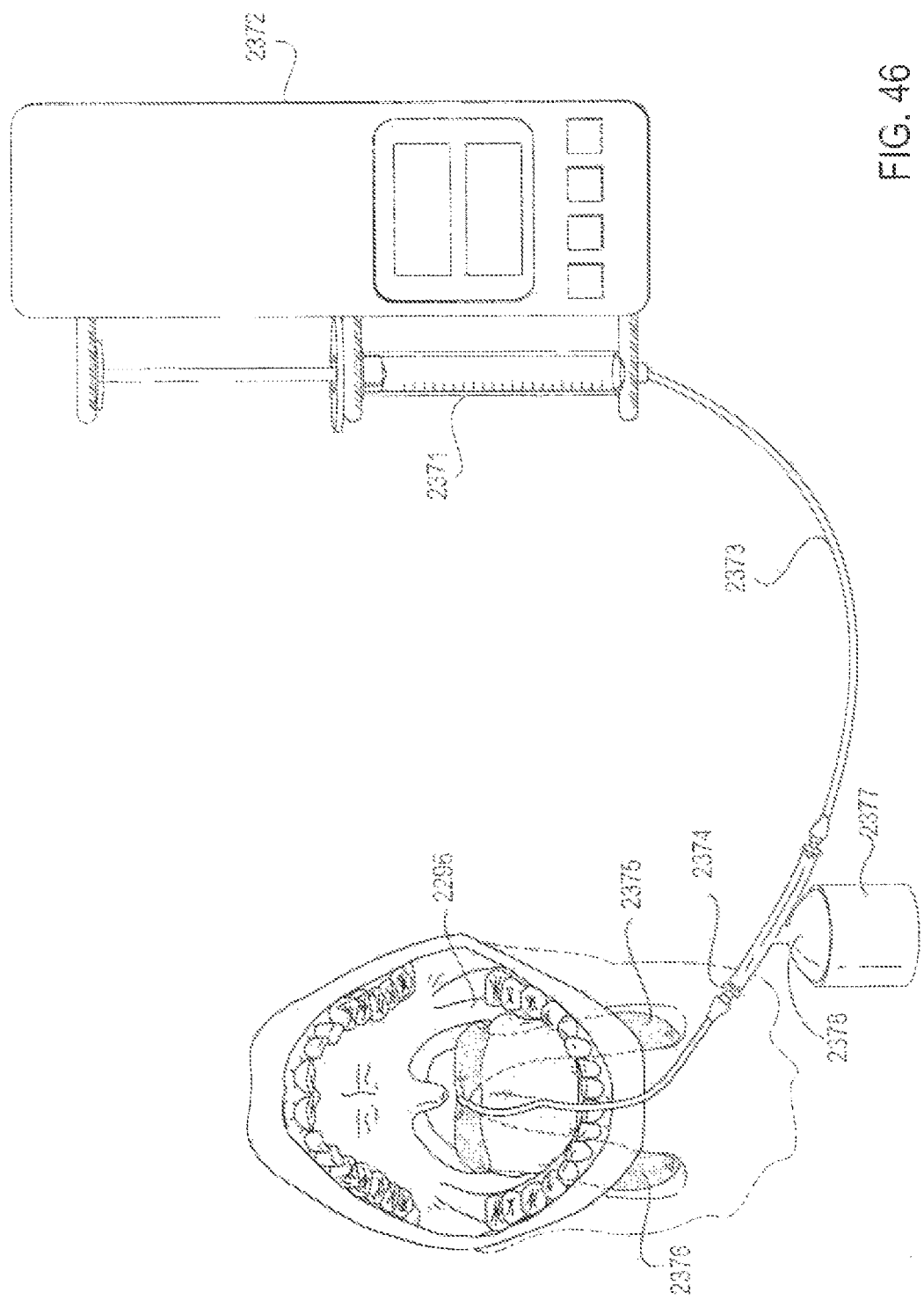
FIG. 46 is a perspective view of an applicator system with a pressure relief and high flow bypass valve and holding container, according to one embodiment.

FIG. 46 shows another exemplary system with applicators (2375 and 2376) connected via a connector (2374) to a flow relief valve (2378), with a flow relief reservoir (2377). This flow relief valve (2378) is also connected via a conduit (2373) to a pump or delivery device (2372) with a reservoir (2371). This flow relief valve (2378) allows for flow until a high flow condition is met, which is a safety feature to prevent improper use that may deliver too much fluid to the throat in too short of a period of time. The reservoir (2371) is there to capture excess flow material and/or alert an operator to the presence of excess material indicating high flow.

FIG. 47A shows another exemplary system with a bifurcated flow conduit (2381) and a pressure relief valve (2382) that may or may not have a relief reservoir (2383). That relief reservoir (2383) and/or flow valve (2382) may or may not also have an indicator such as a light or a whistle (2388) that indicates that pressurized flow is occurring into the bypass compartment (2383). This whistle (2388) may be internal to the bypass chamber (2383) or may be external or partially external. The whistle (2388) may also be configured to signal with air or liquid. A connector connecting to the pumping and/or delivery means (2384) may also be configured to contain a pressure relief capability and/or a high flow condition capability as a fail-safe mechanism.

FIGS. 47B and 47C show another exemplary high-flow relief valve (2382) (or alternatively a three-way pressure valve). This relief valve (2382) contains a spring and/or compressible sponge or rubber material valve (2385, 2386). The compressible valve (2385, 2386) will retract under high flow and high pressure to allow for fluid to flow through bypass opening (2387).

Figure 48A:
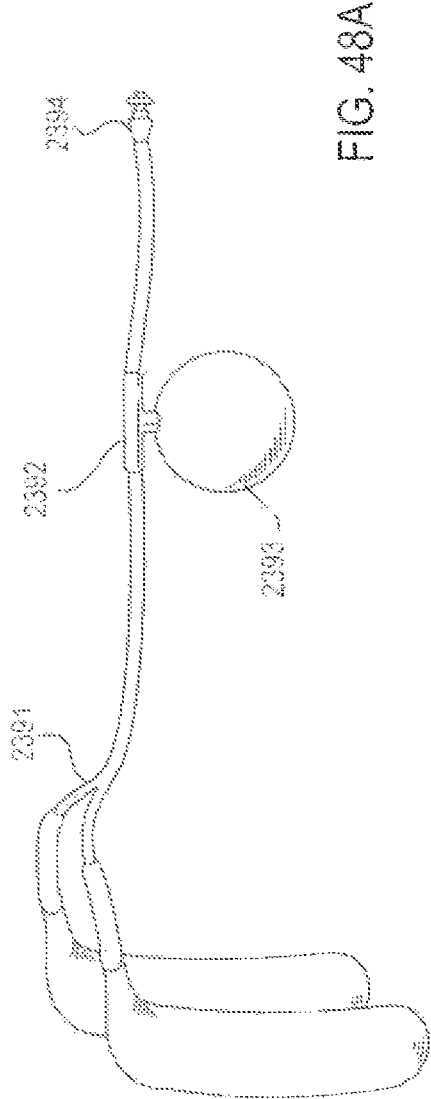
FIGS. 48A and 48B are perspective views of an applicator system with a pressure relief and high flow bypass valve with balloon bypass storage container, according to an alternative embodiment.

FIG. 48A shows another exemplary system with a bifurcated flow conduit (2391) and a pressure relief valve (2392) that may or may not have a relief reservoir (2293). That relief reservoir (2393) and/or flow valve (2392) may or may not also have an indicator such as a light or a visual expansion of the balloon (2393) that indicates that pressurized flow is occurring into the bypass compartment (2393). A connector connecting to the pumping and/or delivery means (2394) may or may not also be configured to contain a pressure relief capability and/or a high flow condition capability as a fail-safe mechanism.

Figure 48B:
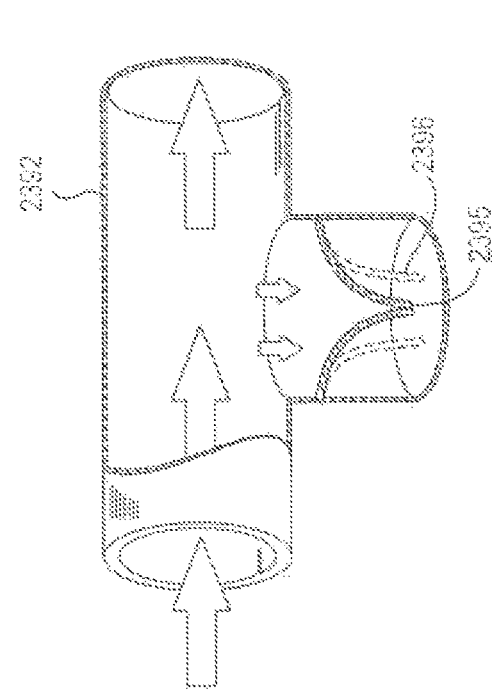

FIG. 48B shows another exemplary device and cross section for a two or more way pressure and/or high flow relief valve (2392). This relief valve contains a duckbill or flapping valve (2395, 2396). The compressible valve will retract under high flow and high pressure (2396) to allow for fluid to flow through the opening.

Figure 49C:
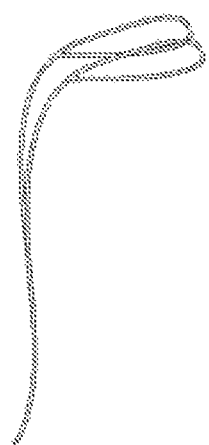
FIGS. 49A-49C are perspective views of an applicator with a curved segment of the drug delivery conduit that allows for manual compression together during application and removal, according to one embodiment.
Figure 49B:
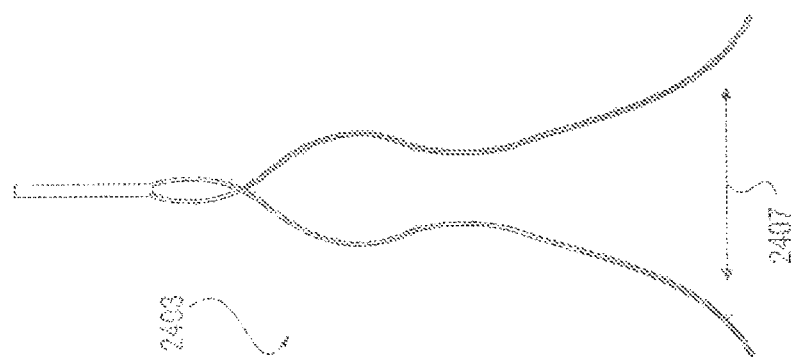
Figure 49A:
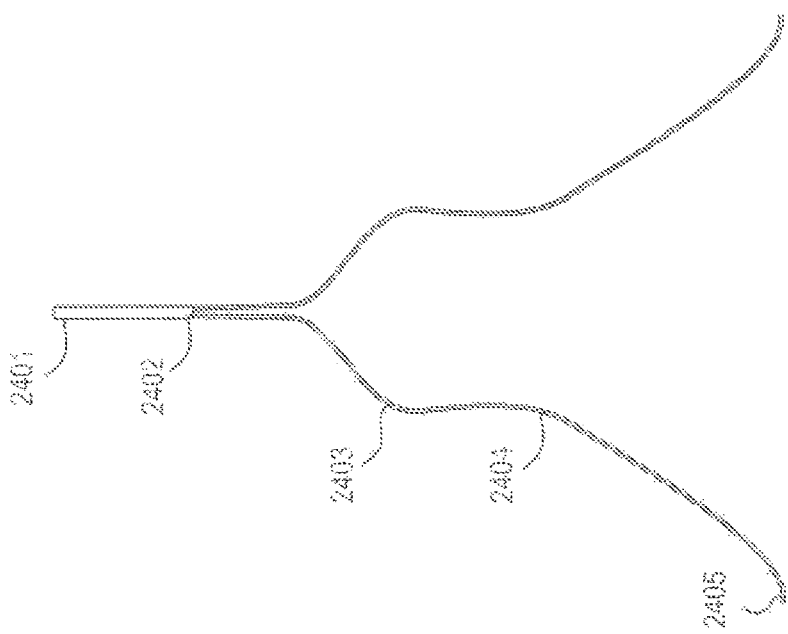
Figure 51A:
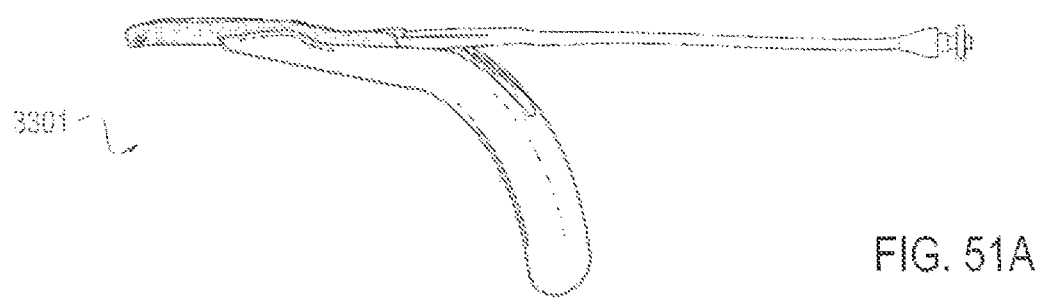
FIGS. 51A-51D are perspective, diagrammatic views, illustrating a process of utilizing an introducer means to insert an applicator device, according to one embodiment.
Figure 51B:
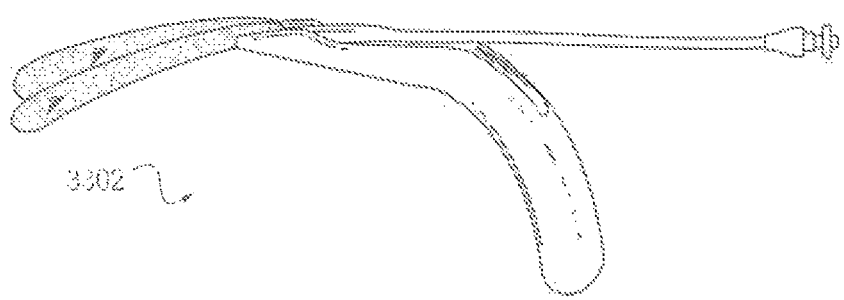
Figure 51C:
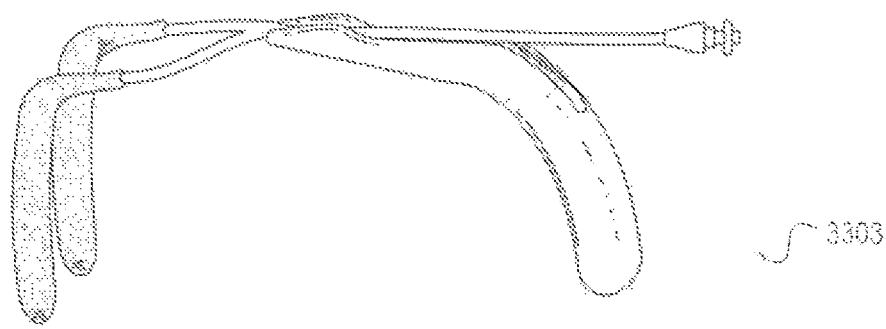
Figure 51D:
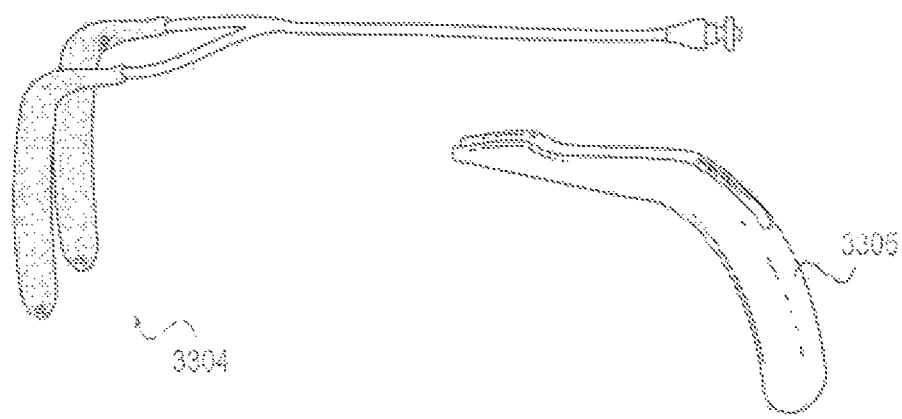

FIGS. 49A and 49B show another exemplary device from a bird's eye view, and FIG. 49C shows a lateral view. These are partial views that are missing at least a portion of the main drug delivery conduit (2401) that is connecting to a drug reservoir and/or a delivery device such as a pump. This drug delivery conduit bifurcates (2402) into two or more conduits. These conduits have a curved shape such that they are able to be placed within the airway to contact at least a portion of tonsillar pillar and/or the piriform sinus. These curved conduits have a section in the lateral section that is curved (2403 and 2404). A first curve (2403) allows for compression with fingers or a device to make the applicator portions move together (2407) for placement into the correct anatomical location. A second curved portion (2404) re-directs the conduits to direct the applicators into contact with the wall of the mucosa and a third segment (2405) curves downward to direct the applicators into the piriforms sinus area vertically as opposed to the lateral movement of the other curves. This lateral downward movement can be seen in FIG. 49C and the compression of the applicators is seen from a top view in FIG. 49B.

FIGS. 50A and 50B show another exemplary embodiment of a device (3201) and applicator (3208) with an introducer device (3204). The introducer device (3204) is used by the person inserting the device (3201) and applicator (3208), in order to slide it into the correct location without the applicators prematurely curving. This guiding mechanism of the curvature (3202) allows the applicators to be in a more straightened configuration than in their native curved applicator state (3207). The advancement of the device and applicator (3208) by threading or guiding forward the drug delivery conduit (3206) causes the applicators to splay outward into their native or applied state (3207) from the constricted and/or straightened insertion state (3202). Once the advancing of the device (3208) has been done such that the bifurcation segment is past the end or apex of the introducer device (3203) then the drug delivery conduit (3206) can be removed from the introducer device (3204) through a slit or open conduit (3209) in the wall of the introducer device.

FIGS. 51A-51D show an exemplary embodiment during the advancement and activation of the curvature of the applicator segments. In the loaded state (3301) the applicators are relatively compact and may be straighter than normal to allow for easy insertion into the back of the throat. Then during the initial advancement (3302) the curvature starts to turn back to the native state for the applicators since they have been held in by the introducer device's shape and/or wall contour. Then once the applicator curvature is fully extended (3303) further advancement will allow them to expand into place and/or curve into place. Finally, when advancement is past the point of a bifurcation (3304) then the introducer device can slide off and/or slide away from the applicator device and drug delivery conduit.

Figure 52:
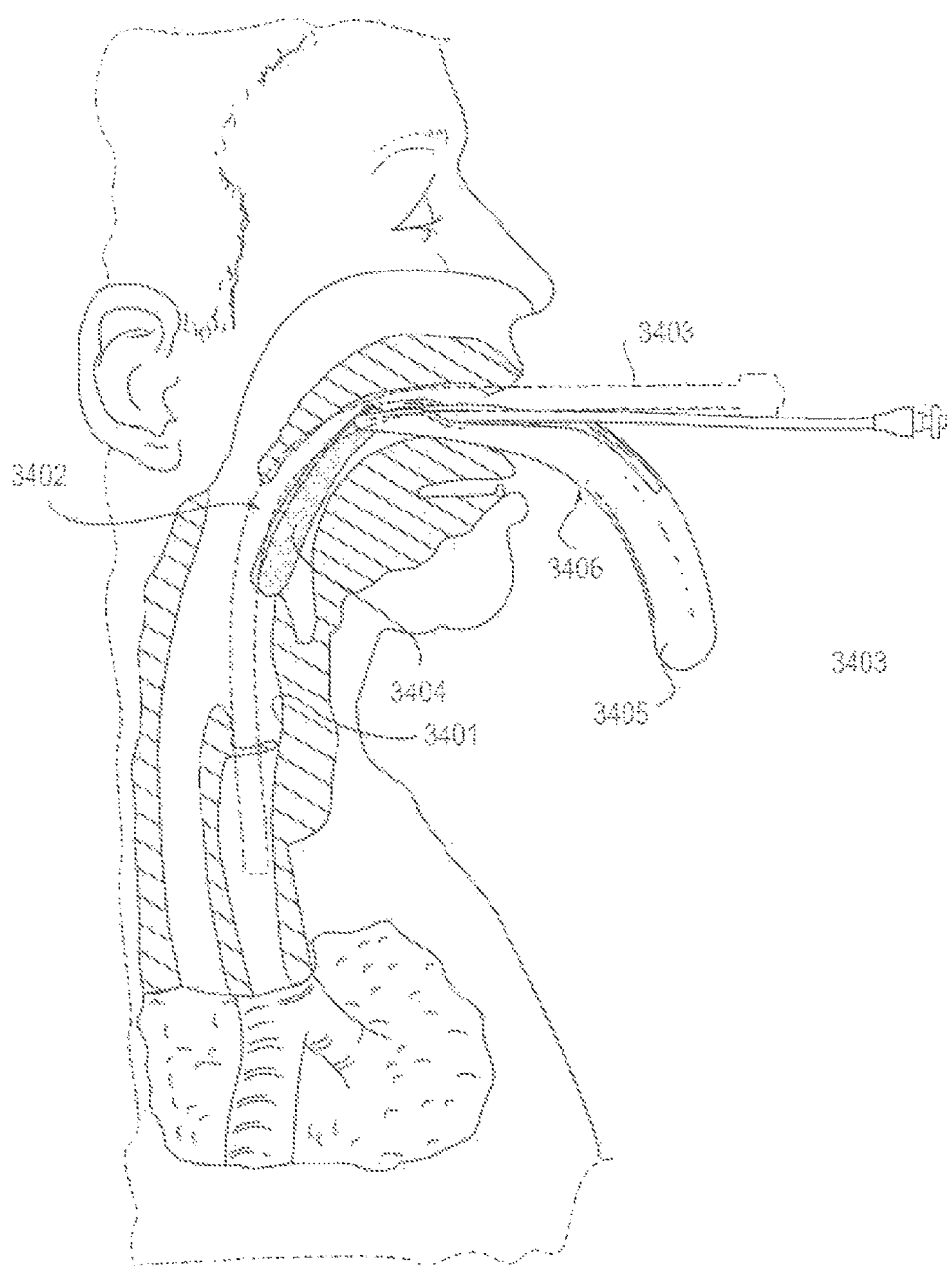
FIG. 52 is a cross-sectional view, diagrammatic view of a head, illustrating insertion of an applicator device using a guide of the endotracheal tube in situ, according to one embodiment.

FIG. 52 is an exemplary cross sectional view of the applicator device (3402) being applied into the airway (3401) by inserting the introducer device (3406) and advancing the drug delivery conduit and/or applicator device (3404) forward to insert the device into the airway (3401). The introducer device may have a handle (3405) to guide the insertion and it may or may not have a curvature or couture (3406) to guide the advancement along an endotracheal tube (3403).

Figure 53:
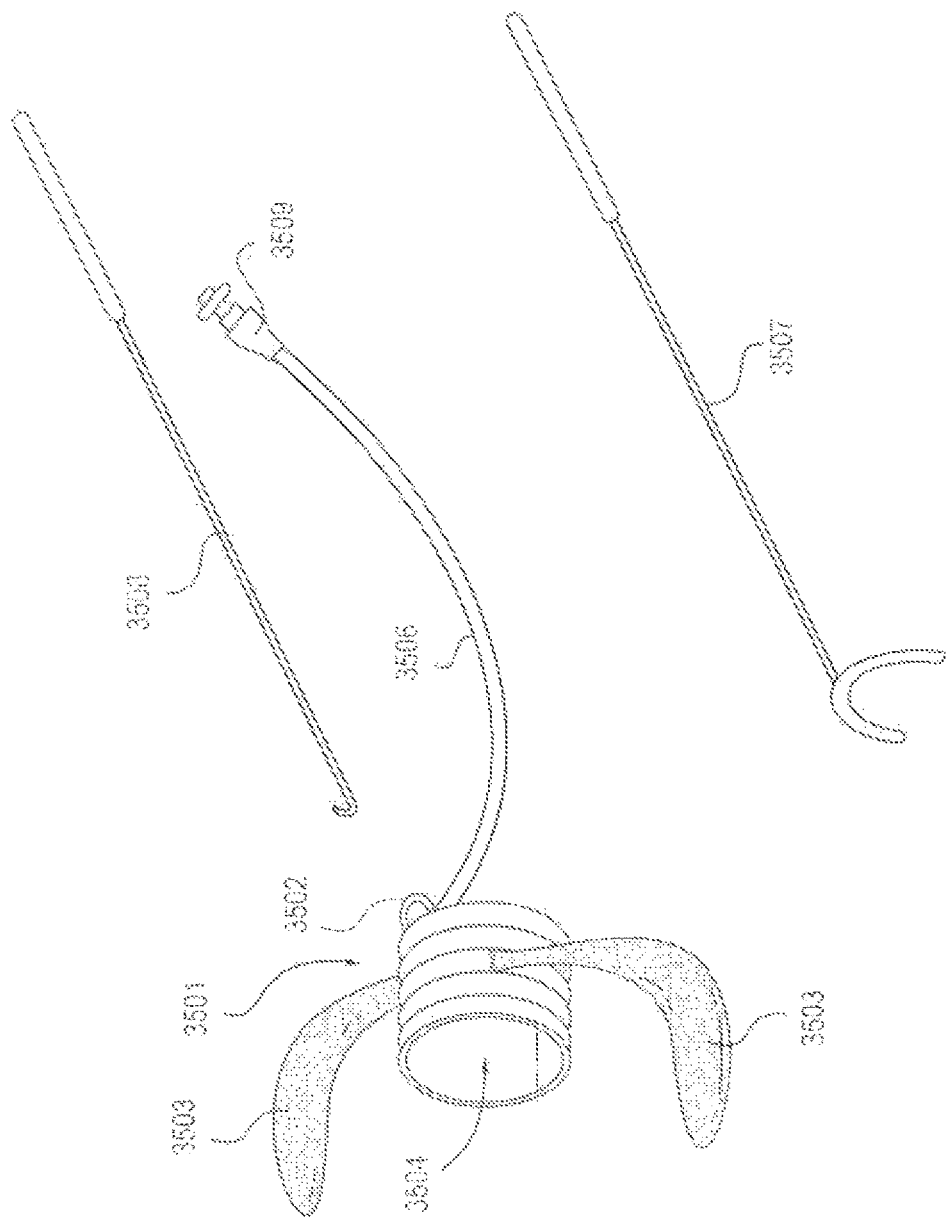
FIG. 53 is a perspective view of an applicator device and introducer tools to advance and/or withdraw the device in the upper airway, according to one embodiment.

FIG. 53 is an exemplary embodiment of a device and system for administering topical anesthetic to the upper airway. The applicator sections (3503) are configured to contact specific anatomical areas such as but not limited to the piriform sinus and/or tonsillar pillars or other area in the airway. The applicator device (3501) may have a guide channel (3504) to slide down the endotracheal tube and a loop (3502). Additionally, a drug or energy delivery conduit (3506) has a connector (3509) that supplies a numbing or desensitizing pharmacological and/or energy to the device (3501) and/or the applicators (3503). Introducer components (3508 and 3507) may be used to hook onto or push against specific areas to insert and/or withdraw the device from the airway of a patient. Additionally the drug or energy delivery conduit (3506) could serve as a means to withdraw the device.

Figure 54:
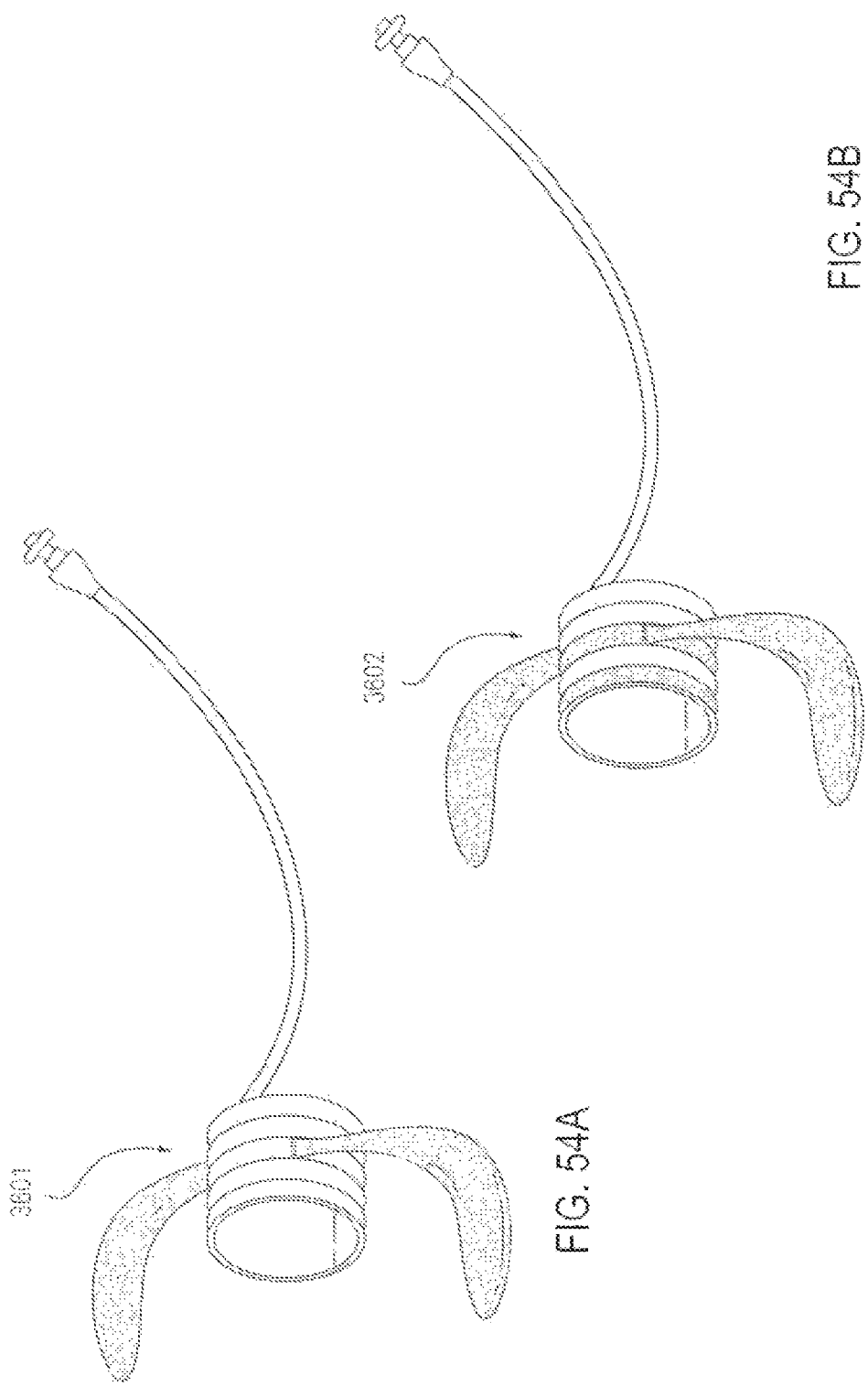
FIGS. 54A and 54B are perspective views of two embodiments of an applicator device with specific targeted applicator segments and a body which can be at least partially made to be a general area applicator, according to various alternative embodiments.

FIGS. 54A and 54B demonstrate exemplary embodiments of a device and system for administering topical anesthetic to the upper airway. The device body may be configured to have some applicator rings or segments and some non-applicator areas (3602) in addition to the applicator pludgets to deliver the anesthetic effect or it may have no ability to deliver an effect outside the applicator sections themselves (3601).

Figure 55:
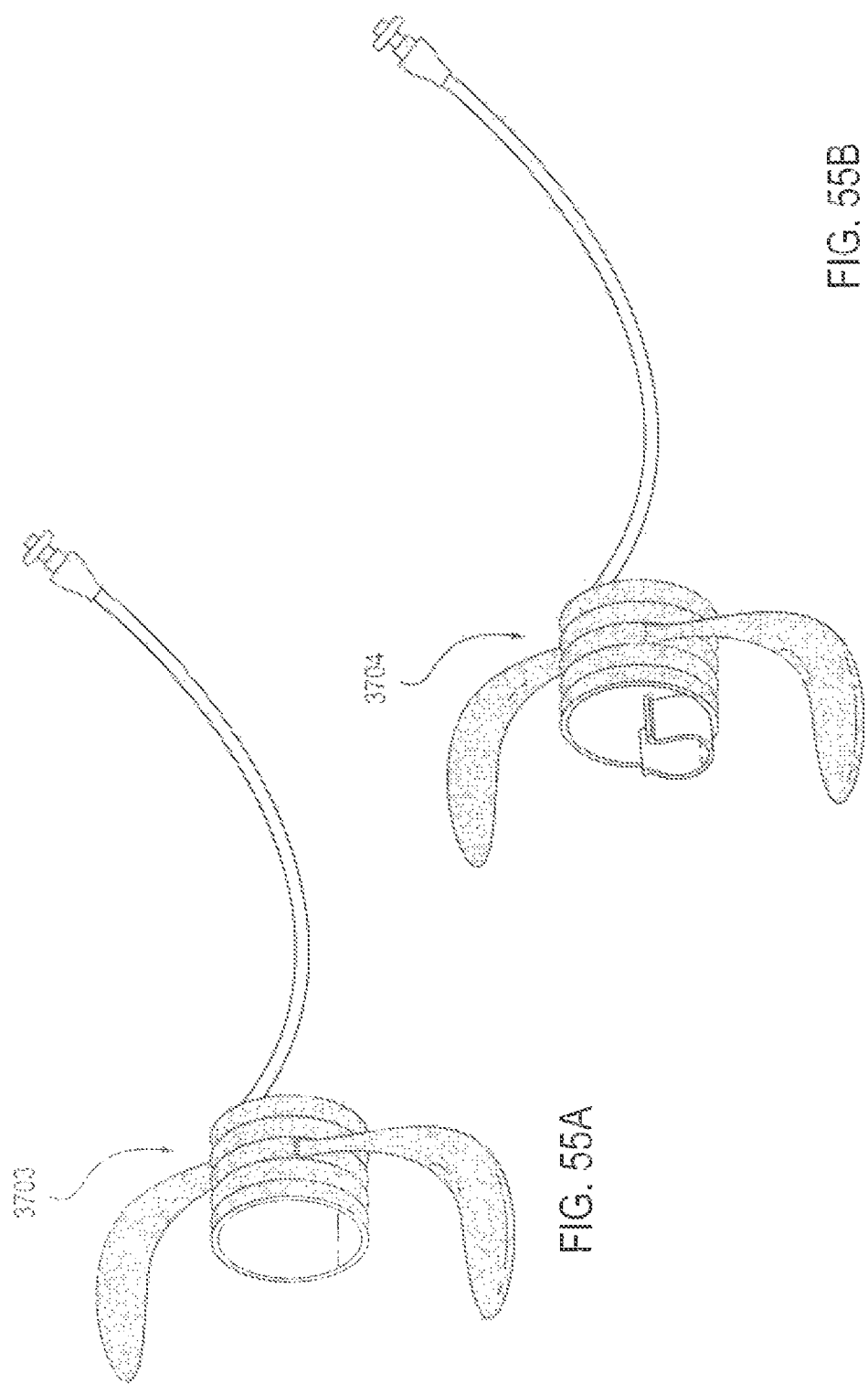
FIGS. 55A and 55B are perspective views of two embodiments of an applicator device with specific targeted applicator segments and a body region that can be made to, or not to be a general applicator as well as demonstrating an open ring attachment means to the endotracheal lube, according to various alternative embodiments.

FIGS. 55A and 55B demonstrate exemplary embodiments of a device for administering topical anesthetic to the upper airway. In FIG. 55A the entire elongated device body is allowed to serve as an applicator (3703) in addition to the applicator segments for specific targeted areas of the piriform sinus and tonsillar pillar. In FIG. 55B the device body has an open section that allows for it to be clipped, or slid onto an endotracheal tube without having to disconnect the tube from the ventilator to slide it down the front. This open section (3704) allows the device body to be pulled apart to get it around the diameter of the tube and then it may return to its native circumferential shape to provide adherence or friction on the tube to allow for adequate positioning where desired.

Figure 56:
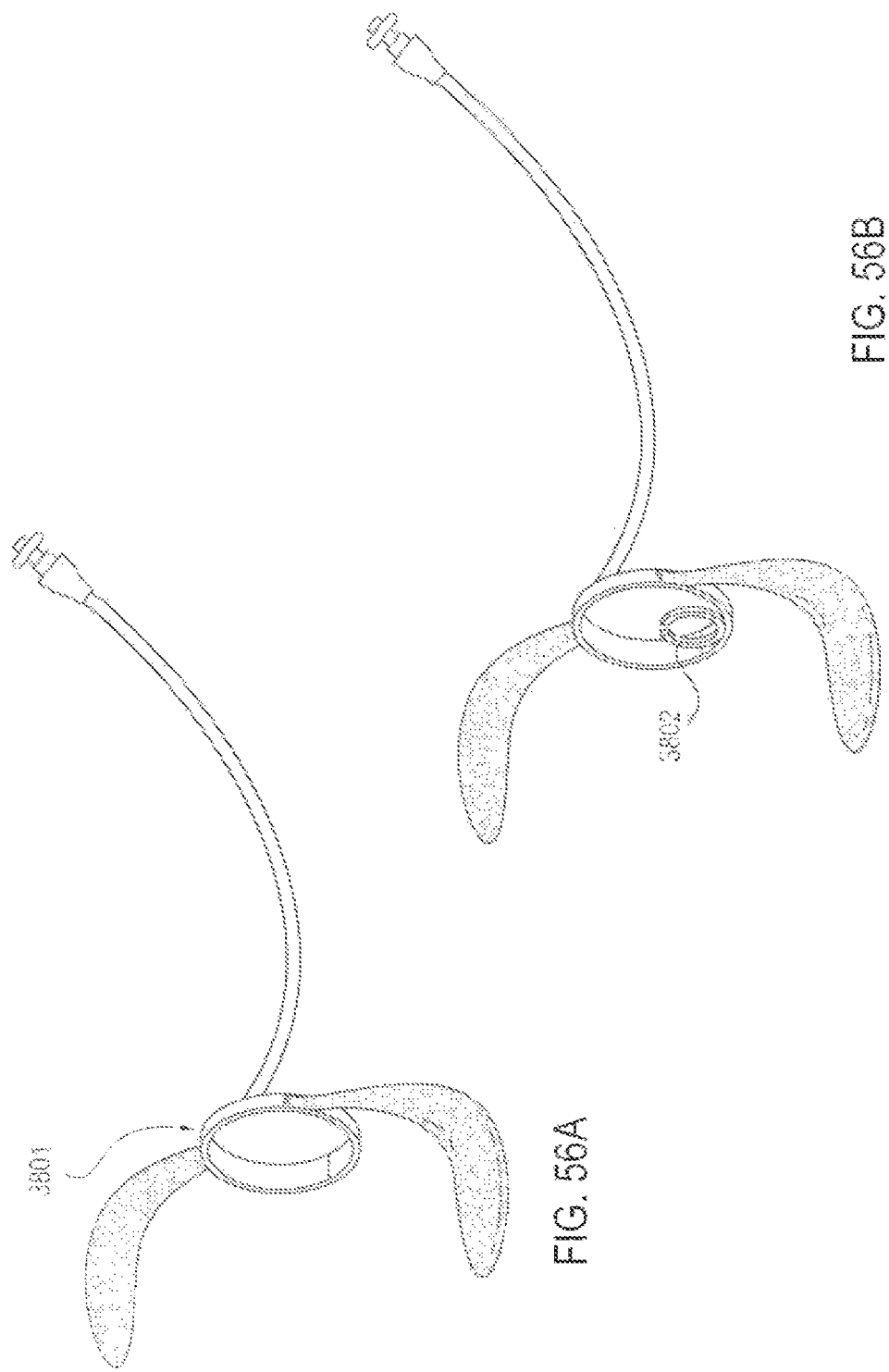
FIGS. 56A and 56B are perspective views of two embodiments of an applicator device with specific targeted applicator segments that have a narrow body segment ring that is closed and/or open to facilitate placement and/or attachment by guiding down the endotracheal tube, according to various alternative embodiments.

FIGS. 56A and 56B demonstrate additional exemplary embodiments with a narrow body section to serve as a guide ring (3801) or open ring clip (3802) onto the endotracheal tube. This narrowed section may be useful to provide a low profile of material within the airway compared to an elongated body segment that may or may not have drug delivery capability.

Figure 57:
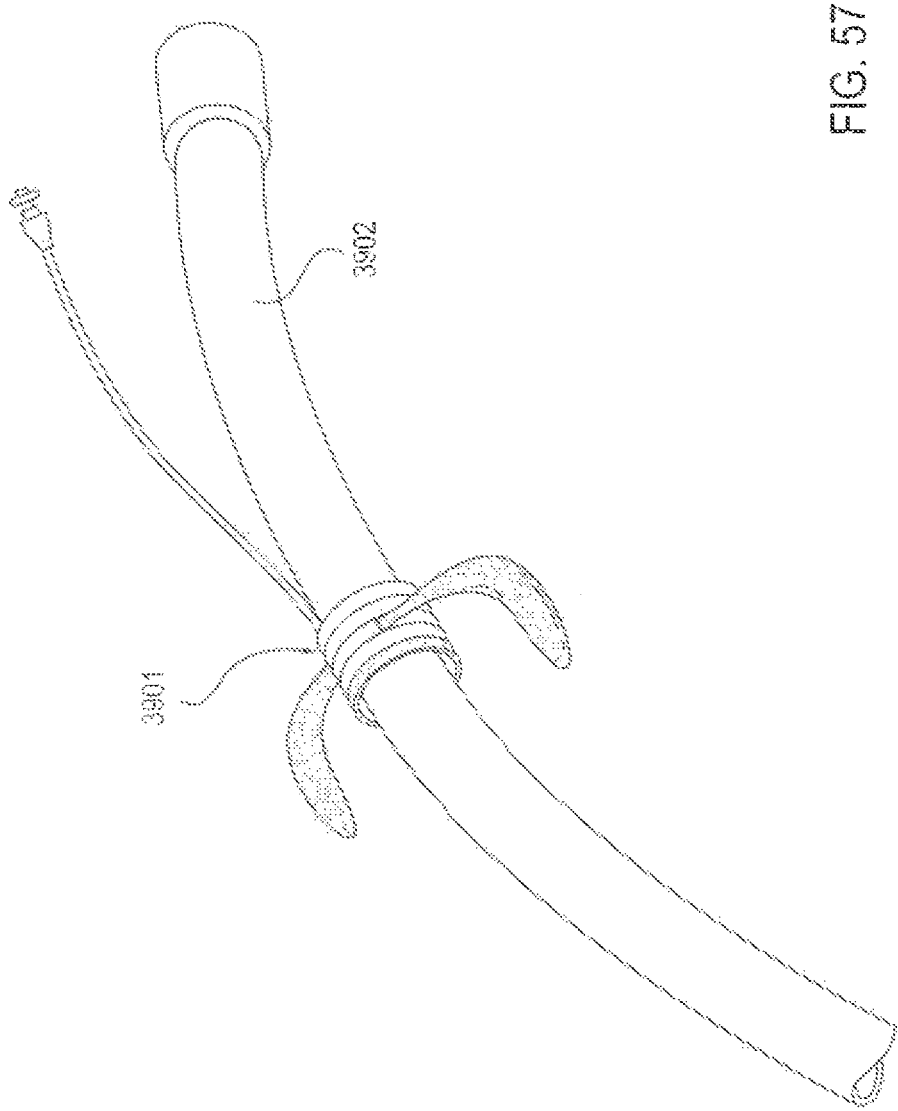
FIG. 57 is a perspective view of an applicator device with specific targeted applicators guided into placement by moving down the endotracheal tube, according to one embodiment.

FIG. 57 is an exemplary view of an embodiment of a drug delivery device and applicator (3901) inserted such that it is at least partially guided by an endotracheal tube (3902).

Figure 58B:
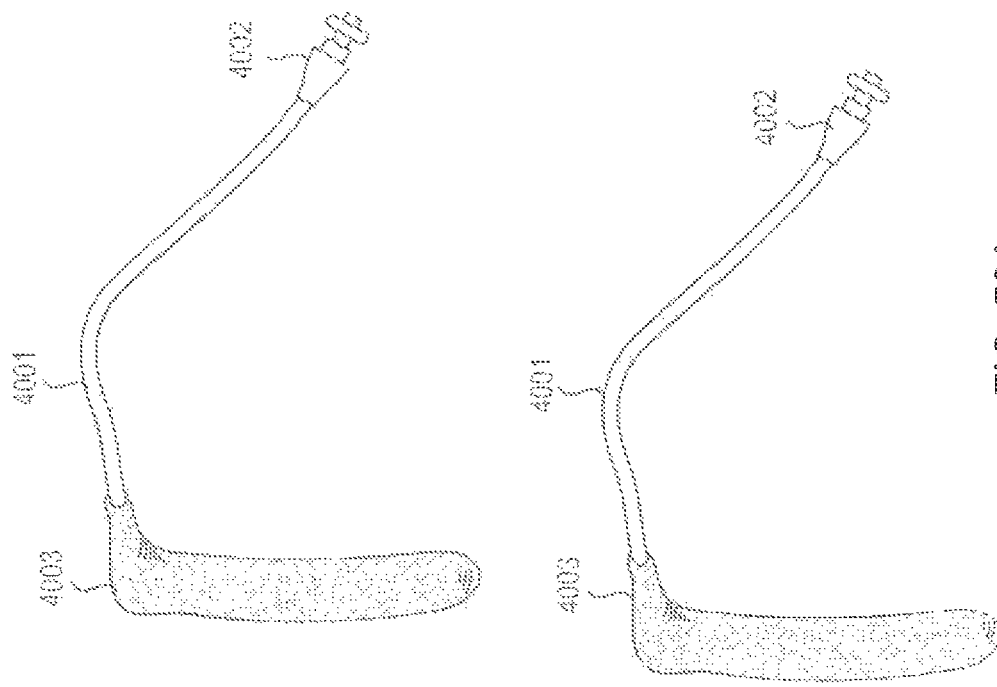
FIGS. 58A and 58B are perspective and intraoral views, respectively, of an applicator system in which the applicators are separate from each other, according to one embodiment.
Figure 58A:
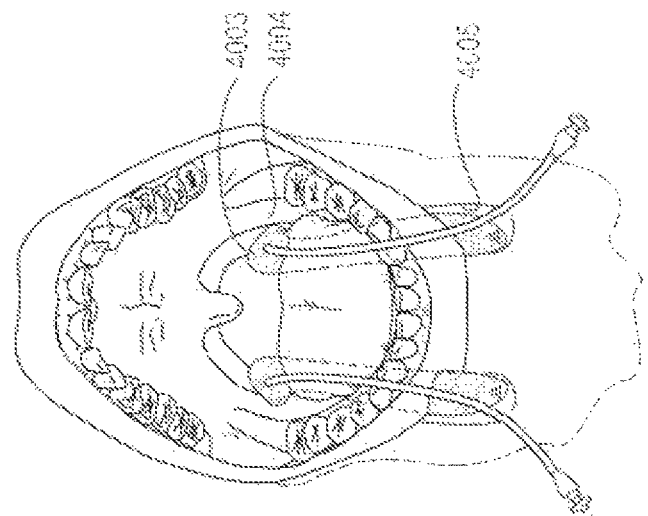

FIG. 58A illustrates another embodiment of an applicator device, in which the applicators (4003) are completely separate from each other. In this embodiment, there are two applicators (4003). Each of the two parts of the device includes an applicator (4003) and a delivery conduit (4001) attached to said applicator. There may be a multitude of applicator-conduit assemblies, arranged in such a way as to target specific anatomic locations to achieve the desired effect. The applicator-conduit assemblies may each be supplied by individual pumps via a standard Luer connector (4002) or other connector, or alternatively by other devices designed to supply the desired effecting mechanism. Alternatively, a manifold may be used to supply the desired substance, energy or other effecting mechanism from a single source.

FIG. 58B depicts the device of FIG. 58A deployed in an upper airway. The applicators (4003) are in direct contact with the tonsillar pillars (4004) near the glossopharyngeal nerve and the piriform sinuses (4005) near the superior laryngeal nerve, on each side.

Figure 59B:
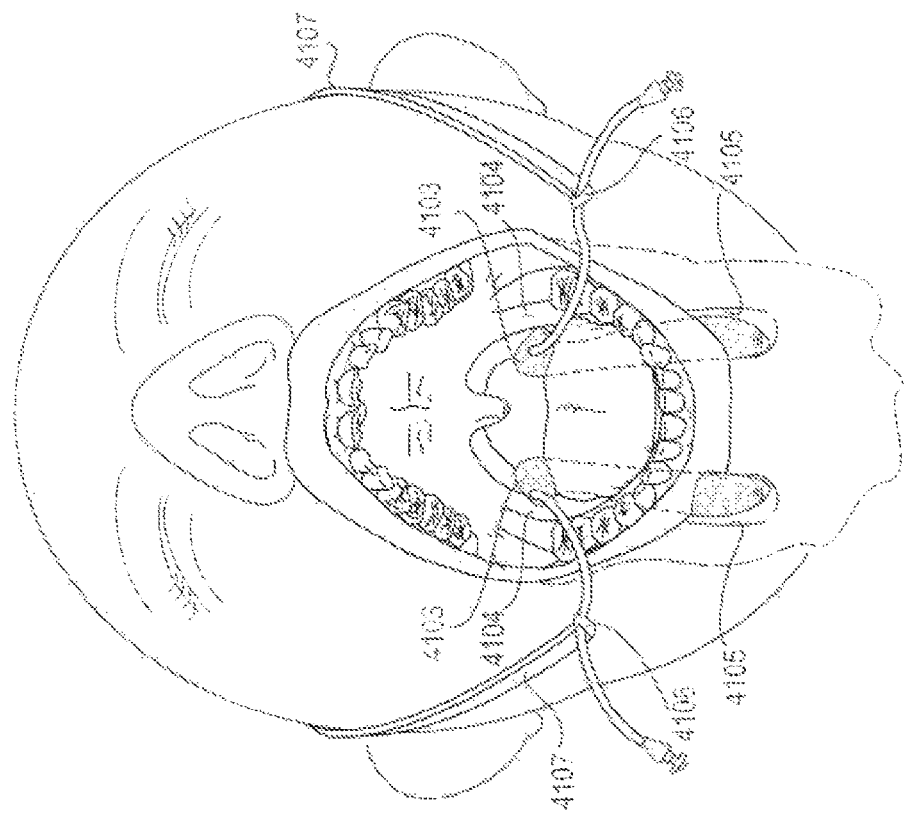
FIGS. 59A and 59B are perspective and intraoral views, respectively, of the applicator system of FIGS. 58A and 58B, illustrating additional, optional features, according to one embodiment.
Figure 59A:
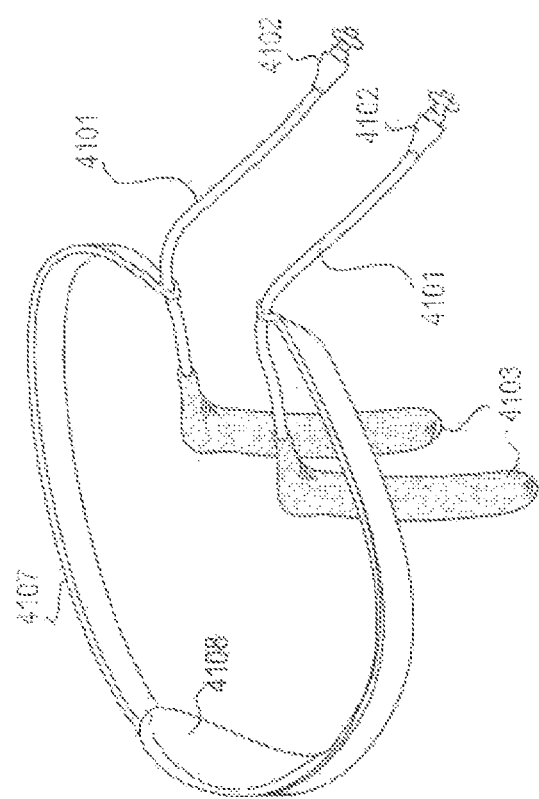

FIG. 59A depicts another embodiment of an applicator device that includes independent applicators (4103) and respective conduits (4101), which may be connected to external pumps via a later connector (4102). In this embodiment, a headband (4107) with support pad (4108) is used to ensure the applicators remain in place.

FIG. 59B depicts the device of FIG. 59A deployed in an upper airway. The applicators are in direct contact with the tonsillar pillars (4104) near the glossopharyngeal nerve and the piriform sinuses (4105) near the superior laryngeal nerve, on each side. The headband (4107) connects to each of the conduits via a simple loop on each side (4106) or other connection.

Figure 60B:
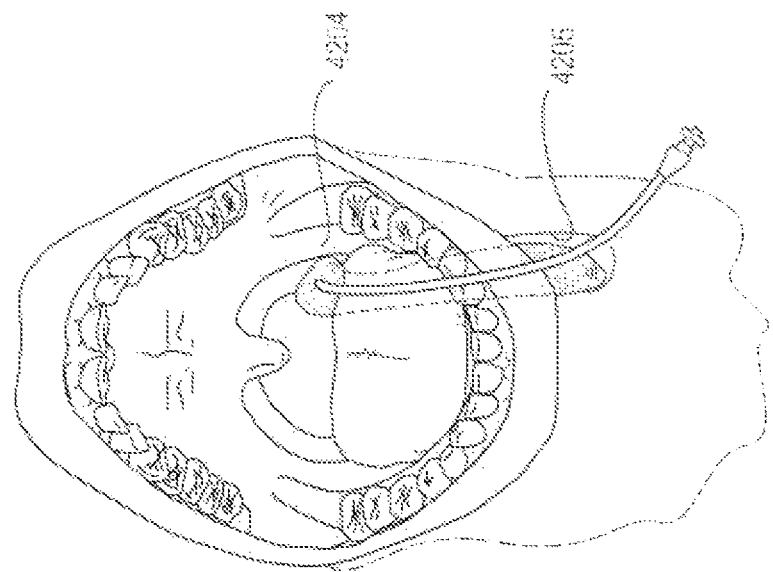
FIGS. 60A and 60B are perspective and intraoral views, respectively, of an applicator system that includes only one applicator, according to one embodiment.
Figure 60A:
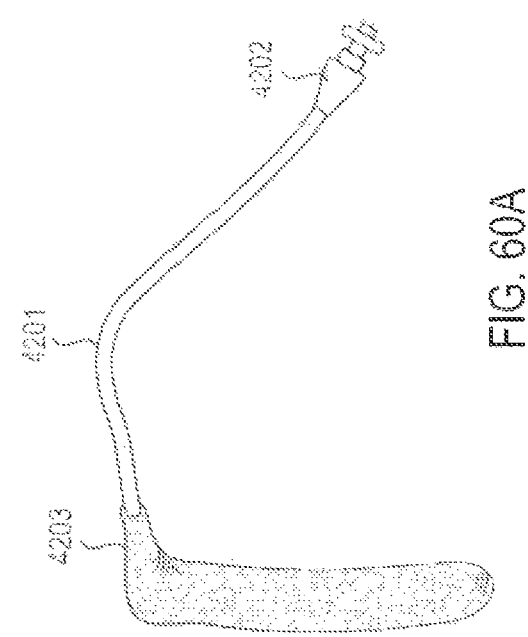

FIG. 60A depicts an exemplary device in which a single applicator (4203) is attached to a single delivery conduit (4201). The device is designed to apply the desired effect to a specific area of the anatomy.

FIG. 60B depicts the device of FIG. 60A in situ, in direct contact with the tonsillar pillars proximally (4204) and piriform sinus distally (4205).

Although this detailed description has set forth certain embodiments and examples, the present invention extends beyond the specifically disclosed embodiments to other alternative embodiments and/or uses of the invention and modifications and equivalents thereof. Thus, it is intended that the scope of the present invention herein disclosed should not be limited by the particular disclosed embodiments described above, but should be determined only by a fair reading of the claims that follow.

The invention claimed is:

1. A device for targeted delivery of a substance to an airway, the device comprising:
   a conduit comprising a proximal end and a bifurcated distal portion having two separate distal ends, wherein the proximal end is configured to be coupled with a source of the substance; and
   at least two applicators made at least partially of a material configured to allow the substance to weep out of the applicators, wherein one of the at least two applicators is coupled with one of the distal ends of the conduit, and another of the at least two applicators is coupled with another of the distal ends of the conduit, wherein each applicator is configured to direct the substance out of the applicator toward one of two sides of an airway, and
   wherein the distal portion of the conduit is configured to apply laterally directed, opposing force to the at least two applicators to cause them to move apart from one another to contact the two sides of the airway.

2. A device as in claim 1, wherein at least the distal portion of the conduit comprises a shape memory material that applies the force by returning to an unconstrained configuration from a constrained configuration.

3. A device as in claim 1, further comprising a sliding adjustment tool coupled with the bifurcated distal portion of the conduit for separating the distal ends of the conduit and the applicators to cause the applicators to apply the laterally directed force against the airway.

4. A device as in claim 3, wherein the sliding adjustment tool is further configured to bring the distal ends of the conduit and the applicators toward one another for removal of the device from the airway.

5. A device as in claim 1, wherein the device is configured to be advanced into the airway and used for substance delivery without requiring attachment to any other airway device.

6. A device as claim 1, wherein the applicators have a curved configuration to conform to a curved portion of the airway such that each applicator, when positioned in the airway, contacts the airway near at least one of a glossopharyngeal nerve or a superior laryngeal nerve on each of the two sides of the airway.

7. A device as in claim 6, wherein each applicator, when positioned in the airway, contacts the airway at or near at least one of a posterior tonsillar pillar or a piriform sinus.

8. A device as in claim 1, further comprising a guide channel attached to the conduit for attaching the device to an endotracheal tube.

9. A device as in claim 1, wherein the applicators are configured to remain within the airway over a period of time during which an endotracheal tube remains within the airway.

10. A device as in claim 1, wherein the proximal end of the conduit is configured to attach to a mechanically driven source of the substance selected from the group consisting of an IV syringe pump, an IV pump, a balloon pump, an IV bag, and other mechanically driven substance reservoirs.

11. A device as in claim 10, wherein at least one of the applicators or the source of substance is configured to control at least one of a rate or an amount of substance delivered.

12. A method for targeted delivery of a substance to an airway, the method comprising:
   advancing a substance delivery device into the airway;
   contacting two sides of the airway with at least two applicators of the substance delivery device, such that each applicator contacts the airway near at least one of a glossopharyngeal nerve or a superior laryngeal nerve on one of the two sides of the airway; and
   delivering the substance through the applicators to contact the airway along the two sides.

13. A method as in claim 12, wherein contacting the airway with the applicators comprises applying lateral, oppositely directed force to the two sides of the airway with the applicators.

14. A method as in claim 13, wherein contacting the airway comprises releasing the applicators from a constrained configuration to assume an unconstrained configuration.

15. A method as in claim 13, wherein contacting the airway comprises separating the applicators apart using a sliding adjustment tool coupled with a bifurcated distal portion of the substance delivery device.

16. A method as in claim 15, further comprising:
using the sliding adjustment tool to bring the applicators closer together; and
removing the device from the airway with the applicators closer together.

17. A method as in claim 13, wherein the substance comprises an anesthetic agent.

18. A method as in claim 17, wherein the anesthetic agent comprises lidocaine.

19. A method as in claim 13, wherein the substance is delivered in a manner such that the substance has a continuous effect during a period of time lasting at least a few minutes and as long as multiple days.

20. A method as in claim 19, wherein the substance is delivered intermittently during at least part of the period of time to provide the continuous effect.

21. A method as in claim 19, wherein the substance is delivered continuously during at least part of the period of time to provide the continuous effect.

22. A method as in claim 13, wherein the substance is delivered at least in part while an additional airway device is in place within the airway.

23. A method as in claim 13, wherein advancing the substance delivery device comprises advancing the device before, during or after advancing an additional airway device into the airway.

24. A method as in claim 13, further comprising allowing the substance delivery device to remain in the airway during a period of time of at least a few minutes and as long as multiple days.

25. A method as in claim 24, wherein an additional airway device is positioned in the airway during at least part of the period of time.

26. A method as in claim 13, further comprising, before the delivering step, attaching a conduit of the substance delivery device to a mechanically driven substance delivery reservoir, wherein delivering the substance comprises automatically delivering the substance from the reservoir through the conduit to the applicators.

27. A device for delivering a substance to an airway, the device comprising:
a conduit comprising a proximal end and a bifurcated distal portion having two separate distal ends, wherein the proximal end is configured to be coupled with a source of the substance;
two applicators, wherein one of the two applicators is coupled with one of the distal ends, and another of the two applicators is coupled with another of the distal ends, and wherein the two applicators are configured to direct the substance out of the applicators toward two different sides of the airway; and
a guide channel attached to the conduit for attaching the device to an endotracheal tube.

* * * * *